US012774318B2

(12) United States Patent
Santamaria

(10) Patent No.: US 12,774,318 B2
(45) Date of Patent: Oct. 27, 2026

(54) METHODS OF TREATING LIVER DISEASE

(71) Applicant: UTI Limited Partnership, Calgary (CA)

(72) Inventor: Pedro Santamaria, Calgary (CA)

(73) Assignee: UTI Limited Partnership, Calgary (CA)

( * ) Notice: Subject to any disclaimer, the term of this patent is extended or adjusted under 35 U.S.C. 154(b) by 1041 days.

(21) Appl. No.: 17/532,584

(22) Filed: Nov. 22, 2021

(65) Prior Publication Data

US 2022/0089682 A1 Mar. 24, 2022

Related U.S. Application Data

(63) Continuation of application No. PCT/US2020/034239, filed on May 22, 2020.

(60) Provisional application No. 62/852,194, filed on May 23, 2019.

(51) Int. Cl.

| | |
|---|---|
| ***C07K 14/74*** | (2006.01) |
| ***A61K 9/51*** | (2006.01) |
| ***A61K 38/10*** | (2006.01) |
| ***A61K 38/17*** | (2006.01) |
| ***A61K 47/69*** | (2017.01) |
| ***A61P 1/16*** | (2006.01) |
| ***C07K 7/04*** | (2006.01) |
| ***C07K 14/705*** | (2006.01) |
| *A61K 38/00* | (2006.01) |
| *B82Y 5/00* | (2011.01) |

(52) U.S. Cl.

CPC ...... *C07K 14/70539* (2013.01); *A61K 9/5115* (2013.01); *A61K 38/10* (2013.01); *A61K 38/1774* (2013.01); *A61K 47/6929* (2017.08); *A61P 1/16* (2018.01); *C07K 7/04* (2013.01); *A61K 38/00* (2013.01); *B82Y 5/00* (2013.01)

(58) Field of Classification Search

CPC .... C07K 7/04; C07K 14/70539; A61K 38/10; A61K 47/6929

See application file for complete search history.

(56) References Cited

U.S. PATENT DOCUMENTS

| | | | |
|---|---|---|---|
| 4,589,330 A | 5/1986 | Teron | |
| 4,818,542 A | 4/1989 | Deluca | |
| 5,731,168 A | 3/1998 | Carter | |
| 5,807,706 A | 9/1998 | Carter | |
| 5,821,333 A | 10/1998 | Carter | |
| 6,712,997 B2 | 3/2004 | Won | |
| 7,642,228 B2 | 1/2010 | Carter | |
| 7,695,936 B2 | 4/2010 | Carter | |
| 8,216,805 B2 | 7/2012 | Carter | |
| 8,354,110 B2 | 1/2013 | Santamaria | |
| 8,679,785 B2 | 3/2014 | Carter | |
| 9,511,151 B2 | 12/2016 | Santamaria | |
| 9,603,948 B2 | 3/2017 | Santamaria | |
| 10,080,808 B2 | 9/2018 | Santamaria | |
| 10,124,045 B2 | 11/2018 | Santamaria | |
| 10,172,955 B2 | 1/2019 | Santamaria | |
| 10,485,882 B2 | 11/2019 | Santamaria | |
| 10,905,773 B2 | 2/2021 | Santamaria | |
| 10,988,516 B2 | 4/2021 | Santamaria | |
| 11,000,596 B2 | 5/2021 | Santamaria | |
| 11,338,024 B2 | 5/2022 | Santamaria | |
| 12,011,480 B2 | 6/2024 | Santamaria | |
| 12,397,038 B2 | 8/2025 | Santamaria | |
| 12,448,419 B2 | 10/2025 | Santamaria | |
| 2003/0068363 A1 | 4/2003 | Clark | |
| 2005/0003431 A1 | 1/2005 | Wucherpfennig | |
| 2005/0208120 A1 | 9/2005 | Albani | |
| 2007/0154953 A1 | 7/2007 | Brunner | |
| 2009/0155292 A1 | 6/2009 | Santamaria | |
| 2011/0059121 A1 | 3/2011 | Santamaria | |
| 2011/0250146 A1 | 10/2011 | Zhang | |
| 2012/0093934 A1 | 4/2012 | Santamaria | |
| 2012/0121649 A1 | 5/2012 | Santamaria | |
| 2013/0089553 A1 | 4/2013 | Carter | |
| 2013/0171179 A1 | 7/2013 | Burrows | |
| 2013/0302421 A1 | 11/2013 | Santamaria | |
| 2013/0330414 A1 | 12/2013 | Santamaria | |
| 2014/0105980 A1 | 4/2014 | Santamaria | |
| 2014/0294982 A1 | 10/2014 | Freund | |
| 2015/0209446 A1 | 7/2015 | Santamaria | |
| 2015/0250871 A1 | 9/2015 | Santamaria | |
| 2017/0095544 A1* | 4/2017 | Santamaria | A61P 37/06 |
| 2017/0274096 A1 | 9/2017 | Santamaria | |

(Continued)

FOREIGN PATENT DOCUMENTS

| | | |
|---|---|---|
| WO | 1992018150 | 10/1992 |
| WO | 2008109852 | 9/2008 |

(Continued)

OTHER PUBLICATIONS

Li et al., Front. Immunol., 2022, vol. 13, Article 968432.*
Riedhammer et al., Front. Immunol., 2015, vol. 6, Article 322.*
Weiler-Normann et al., Dig. Dis. Sci., 2016, vol. 61:2462-2464.*
Singha, S. et al., "Peptide-MHC-based Nanomedicines for Autoimmunity Function as T-cell Receptor Microclustering Devices", Nat Nanotechnol., 12(7):701-10, (2017).

(Continued)

*Primary Examiner* — Xiaozhen Xie

(74) *Attorney, Agent, or Firm* — Global Patent Group Inc.; Cynthia Hathaway

(57) ABSTRACT

Described herein are compositions and methods useful for treating hepatic inflammatory disorders. The compositions and methods utilize ubiquitous, non-tissue specific antigens associated with major histocompatibility complexes (MHCs) and coupled to a nanoparticle core to induce regulatory T cells and regulatory B cells.

10 Claims, 46 Drawing Sheets

Specification includes a Sequence Listing.

(56) References Cited

U.S. PATENT DOCUMENTS

| | | | |
|---|---|---|---|
| 2017/0312348 | A1 | 11/2017 | Santamaria |
| 2017/0333540 | A1 | 11/2017 | Santamaria |
| 2018/0127481 | A1 | 5/2018 | Santamaria |
| 2019/0076545 | A1 | 3/2019 | Santamaria |
| 2019/0134171 | A1 | 5/2019 | Santamaria |
| 2020/0009265 | A1 | 1/2020 | Santamaria |
| 2020/0057048 | A1 | 2/2020 | Santamaria |
| 2021/0145949 | A1 | 5/2021 | Santamaria |
| 2021/0205470 | A1 | 7/2021 | Santamaria |
| 2022/0401534 | A1 | 12/2022 | Santamaria |
| 2023/0355730 | A1 | 11/2023 | Santamaria |
| 2024/0201171 | A1 | 6/2024 | Santamaria |
| 2024/0299536 | A1 | 9/2024 | Santamaria |
| 2025/0051420 | A1 | 2/2025 | Santamaria |
| 2025/0121043 | A1 | 4/2025 | Santamaria |

FOREIGN PATENT DOCUMENTS

| | | |
|---|---|---|
| WO | 2013144811 | 10/2013 |
| WO | 2014080286 | 5/2014 |
| WO | 2015063616 | 5/2015 |
| WO | 2016198932 | 12/2016 |
| WO | 2018087597 | 5/2018 |
| WO | 2019106435 | 6/2019 |
| WO | 2020237160 | 11/2020 |

OTHER PUBLICATIONS

International Application No. PCT/US2020/034233; International Preliminary Report on Patentability, date of issuance Dec. 2, 2021; 5 pages.

International Application No. PCT/US2020/034239; International Search Report and Written Opinion of the International Searching Authority, date of mailing Sep. 30, 2020; 9 pages.

Umeshappa, C. et al., "Suppression of A Broad Spectrum of Liver Autoimmune Pathologies by Single Peptide-MHC-Based Nanomedicines", Nat Commun., 10(1):2150, (2019).

Charatcharoenwitthaya, P. et al., "Long-Term Survival and Impact of Ursodeoxycholic Acid Treatment for Recurrent Primary Biliary Cirrhosis After Liver Transplantation", Liver Transpl., 13:1236-1245, (2007).

Fickert, P. et al., "Characterization of Animal Models for Primary Sclerosing Cholangitis (PSC)", J. Hepatol., 60:1290-1303, (2014).

Hardtke-Wolenski, M. et al., "Genetic Predisposition and Environmental Danger Signals Initiate Chronic Autoimmune Hepatitis Driven by CD4+ T Cells", Hepatology, 58:718-728, (2013).

Kita, H. et al., "Quantitative and Functional Analysis of PDC-E2-specific Autoreactive Cytotoxic T Lymphocytes in Primary Biliary Cirrhosis", J Clin Invest., 109(9):1231-40, (2002).

Longhi, M.S. et al., "Aetiopathogenesis of Autoimmune Hepatitis", J. Autoimmun., 34:7-14, (2010).

Perrault, S. et al., "Mediating Tumor Targeting Efficiency of Nanoparticles Through Design", Nano Lett, 9(5):1909-15, (2009).

Pollheimer, M. et al., "Animal Models in Primary Biliary Cirrhosis and Primary Sclerosing Cholangitis", Clin. Rev. Allergy Immunol., 48:207-217, doi: 10.1007/s12016-014-8442-y, (2015).

Scott, R. et al., "Synthesis, Characterization, and Applications of Dendrimer-Encapsulated Nanoparticles", J Phys Chem B., 109(2):692-704, (2005).

Xie, J. et al., "Controlled PEGylation of Monodisperse Fe3O4 Nanoparticles for Reduced Non-Specific Uptake by Macrophage Cells", Adv. Mater., 19:3163-3166, (2007).

Xie, J. et al., "One-Pot Synthesis of Monodisperse Iron Oxide Nanoparticles for Potential Biomedical Applications", Pure Appl. Chem., 78(5):1003-1014, (2006).

Xu, C. et al., "Monodisperse Magnetic Nanoparticles for Biomedical Applications", Polymer Int., 56(7):821-6, (2007).

Chang, J. et al., "Design, Engineering, and Production of Human Recombinant T Cell Receptor Ligands Derived From Human Leukocyte Antigen DR2", J Biol Chem., 276(26):24170-6, (2001).

Clemente-Casares, J., "pMHC-Class II Nanovaccine to Treat Autoimmune Diseases", Doctor of Philosophy Thesis, Calgary University, Alberta, Canada, 391 pages, retrieved from: http://theses.ucalgary.ca/handle/11023/1589; (2014).

Clemente-Casares, X. et al., "Expanding Antigen-Specific Regulatory Networks to Treat Autoimmunity", Nature, 530(7591):434-40, (2016).

Clemente-Casares, X. et al., "Peptide-MHC-based Nanovaccines for the Treatment of Autoimmunity: A "One Size Fits All" Approach? ", J Mol Med., 89(8):733-42, (2011).

Cochran, J. et al., "The relationship of MHC-peptide binding and T cell activation probed using chemically defined MHC class II oligomers", Immunity, 12(3):241-50, (2000).

Diwan, M. et al., "Biodegradable Nanoparticle Mediated Antigen Delivery to Human Cord Blood Derived Dendritic Cells for Induction of Primary T Cell Responses", J Drug Target, 11(8-10):495-507, (2003).

Getts, D. et al., "Microparticles Bearing Encephalitogenic Peptides Induce T-cell Tolerance and Ameliorate Experimental Autoimmune Encephalomyelitis", Nat Biotechnol., 30(12):1217-24, (2012).

Ha, J. et al., "Immunoglobulin Fc Heterodimer Platform Technology: From Design to Applications in Therapeutic Antibodies and Proteins", Front Immunol., 7(394):1-16, (2016).

Kalandadze, A. et al., "Replacement of the Hydrophopic Transmembrane Region by a Leucine Zipper Dimerization Motif Allows the Assembly and Secretion of Soluble DR αß Heterodimers", J Biol Chem., 271(33):20156-20162, (1996).

Kozono, H. et al., "Production of Soluble MHC Class II Proteins With Covalently Bound Single Peptides", 369(6476):151-4, (1994).

Lee, Y. et al., "Biodegradable Nanoparticles Containing TLR3 or TLR9 Agonists Together With Antigen Enhance MHC-restricted Presentation of the Antigen", Arch Pharm Res., 33(11):1859-66, (2010).

Longhi, M. et al., "Autoantigen-specific Regulatory T Cells, a Potential Tool for Immune-Tolerance Reconstitution in type-2 Autoimmune Hepatitis", Hepatology, 53(2):536-47, (2011).

Saengruengrit, C. et al., "The Combined Magnetic Field and Iron oxide-PLGA Composite Particles: Effective Protein Antigen Delivery and Immune Stimulation in Dendritic Cells", J Colloid Interface Sci., 520:101-11, (2018).

Schaefer, W. et al., "Heavy and light chain pairing of bivalent quadroma and knobs-into-holes antibodies analyzed by UHR-ESI-QTOF mass spectrometry", MAbs., 8(1):49-55, (2016).

Serra, P. et al., "Increased Yields and Biological Potency of Knob-Into-Hole-Based Soluble MHC Class II Molecules", Nat Commun., 10(1):4917, (2019).

Serra, P. et al., "Nanoparticle-based Approaches to Immune Tolerance for the Treatment of Autoimmune Diseases", Eur J Immunol., 48(5):751-6, (2018).

Serra, P. et al., "Peptide-MHC-Based Nanomedicines for the Treatment of Autoimmunity: Engineering, Mechanisms, and Diseases", Front Immunol., 11:621774, (2021).

Vandenbark, A. et al., "Recombinant TCR Ligand Induces Tolerance to Myelin Oligodendrocyte Glycoprotein 35-55 Peptide and Reverses Clinical and Histological Signs of Chronic Experimental Autoimmune Encephalomyelitis in HLA-DR2 Transgenic Mice", J Immunol., 171(1):127-33, (2003).

Yang, Y. et al., "Antigen-specific nanomedicines for the treatment of autoimmune disease: target cell types, mechanisms and outcomes", Curr Opin Biotechnol., 74: 285-92, (2022).

Yeste, A. et al., "Nanoparticle-mediated Codelivery of Myelin Antigen and a Tolerogenic Small Molecule Suppresses Experimental Autoimmune Encephalomyelitis", Proc Natl Acad Sci USA, 109(28):11270-5, (2012).

* cited by examiner left bar, CD4+ cells from untreated; middle bar, CD4+ cells from pMHC-NP treated
right bar, CD4+ cells from pMHC-NP treated + $PDC_{166}/IA^{g7}$ -NPs

METHODS OF TREATING LIVER DISEASE

CROSS-REFERENCE

This application is a bypass continuation of International Application No. PCT/US2020/034239, filed May 22, 2020, which claims the benefit of U.S. Provisional Application 62/852,194, filed on May 23, 2019, the disclosures of which are incorporated by reference herein in their entireties.

INCORPORATION OF SEQUENCE LISTING

The sequence listing that is contained in the file named "PTI0017-201BC1-US_ST25.txt," which was created on Jan. 30, 2026, and which has a file size of 34,700 bytes bytes as measured in Microsoft Windows operating system, is filed electronically herewith and incorporated herein by reference.

SUMMARY

Provided herein are compositions comprising a plurality of antigen-major histocompatibility complexes coupled to a nanoparticle core. The compositions are useful for treating hepatic inflammatory diseases. Many hepatic inflammatory diseases are associated with general inflammation in the liver. Exemplary hepatic inflammatory diseases include: hepatitis, non-alcoholic fatty liver disease (NAFLD), non-alcoholic steatohepatitis (NASH), cirrhosis, or pyogenic liver abscesses. Often, nonspecific immune inhibitors can be used to treat these diseases, but such inhibitors are associated with significant systemic side-effects. Described herein are compositions comprising ubiquitous autoantigen-MHC complexes coupled to nanoparticles (uaMHC-NP), that are useful for treating hepatic inflammatory diseases or expanding populations of T regulatory cells in the liver that suppress autoreactive (i.e., autoimmune or inflammatory) T cells.

Primarily, the treatments described herein are multi-purpose in that a single composition can treat multiple hepatic inflammatory diseases disorders that are not mechanistically or pathologically linked. Many treatments, for example, corticosteroids or antibodies against general inflammatory mediators, that are multi-purpose in this way result in systemic immunosuppression, thus, increasing a treated patients' risk for developing secondary infections and systemic immunological complications. The compositions described herein, while being multi-purpose, also spare systemic immunity leaving intact the ability of a patient to fight off viral, bacterial, fungal infection, or tumors.

In one aspect described herein is a composition for use in treating a hepatic inflammatory disease, the composition comprising: (a) a plurality of antigen-major histocompatibility complexes (antigen-MHCs), each antigen-MHC of the plurality comprising a ubiquitous autoantigen associated with a binding groove of an MHC molecule, wherein the ubiquitous autoantigen is not a liver specific antigen; and (b) a nanoparticle core possessing a diameter of between 1 and about 100 nanometers; wherein the antigen-MHCs are coupled to the nanoparticle core or a biocompatible layer surrounding the nanoparticle core. In certain embodiments, the MHC molecule is an MHC class II molecule. In certain embodiments, the nanoparticle core is a metal or metal oxide. In certain embodiments, the metal is iron. In certain embodiments, the metal oxide is iron oxide. In certain embodiments the diameter is greater than 15 nanometers and no more than about 30 nanometers. In certain embodiments, the diameter is between about 5 nanometers and about 50 nanometers. In certain embodiments, the diameter is between about 5 nanometers and about 25 nanometers. In certain embodiments, the plurality of antigen-MHCs is coupled to the nanoparticle core at an antigen-MHC to nanoparticle core ratio of at least 10:1. In certain embodiments, the plurality of antigen-MHCs is coupled to the nanoparticle core at an antigen-MHC to nanoparticle core ratio of no more than about 150:1. In certain embodiments, the plurality of antigen-MHCs is coupled to the nanoparticle core at a density from about 0.4 to about 13 antigen-MHCs per 100 $nm^2$ of nanoparticle core surface area. In certain embodiments, the antigen-MHCs are covalently coupled to the nanoparticle core. In certain embodiments, the antigen-MHCs are coupled to the nanoparticle core by a polyethylene glycol (PEG) linker having a mass of less than about 5 kilodaltons. In certain embodiments, the nanoparticle core further comprises a biocompatible coating. In certain embodiments, the ubiquitous autoantigen comprises a polypeptide derived from a protein that at steady-state exists in or on an intracellular compartment. In certain embodiments, the intracellular compartment is cytosol, mitochondria, Golgi apparatus, endoplasmic reticulum, nucleus, or plasma membrane. In certain embodiments, the intracellular compartment is a mitochondrion. In certain embodiments, the ubiquitous autoantigen comprises a polypeptide derived from any one or more of: Mdh1; Actg1; Vim; Ldha; Gapdh; Ywhaz; Fabp3; Atox1; Prdx1; Txndc17; Nel; Hnrnpf; Cops9; Lsm5; Pena; Hnrnpa2b1; Tkt; Rbbp4; Rbbp7; Nme1; Rack1; Tfrc; Gab1; Lifr; Egfr; Tfrc; S100a6; Fadd; Cnrip1; Eps1511; Nptp; Hspe1; Bax; Hspa9; Gstp1; Ndufab1; Mdh2; Hspd1; Atp5f1a; Hspd1; Atp5f1e; Arf3; Arf4; Arf5; Dpy30; Pitpnb; Ap1b1; Arl1; Prre1; Copz1; Sar1b; Pgrmc1; Cyp2f2; Atp2a2; Fkbp2; Cyb5a; Erp44; Canx; Hsp90b1; Vcp; and I.man1. In certain embodiments, the ubiquitous autoantigen is pyruvate dehydrogenase complex-E2 component (PDC-E2) or a polypeptide derived therefrom. In certain embodiments, the ubiquitous autoantigen is Cytochrome P450 2D6 (CYP2D6) or a polypeptide derived therefrom. In certain embodiments, the ubiquitous autoantigen is actin (ACTB) or a polypeptide derived therefrom. In certain embodiments, the ubiquitous autoantigen is soluble liver antigen (SLA) or a polypeptide derived therefrom. In certain embodiments, the ubiquitous autoantigen is formimidoyltransferase-cyclodeaminase (FTCD) or a polypeptide derived therefrom. In certain embodiments, the ubiquitous autoantigen is myeloperoxidase (MPO). In certain embodiments, the ubiquitous autoantigen is selected from the group consisting of: PDC-$E2_{353-367}$; PDC-$E2_{72-86}$; PDC-$E2_{422-436}$; PDC-$E2_{353-367}$; PDC-$E2_{80-94}$; PDC-$E2_{535-549}$; PDC-$E2_{629-648}$; PDC-$E2_{122-135}$ PDC-$E2_{249-263}$; PDC-$E2_{249-263}$; and any combination thereof. In certain embodiments, the ubiquitous autoantigen is selected from the group consisting of: PDC-$E2_{422-436}$, PDC-$E2_{80-94}$, and the combination of PDC-$E2_{422-436}$ and PDC-$E2_{80-94}$. In certain embodiments, the ubiquitous autoantigen is selected from the group consisting of: $CYP2D6_{284-298}$; $CYP2D6_{289-303}$; $CYP2D6_{318-332}$; $CYP2D6_{313-332}$; $CYP2D6_{393-412}$; $CYP2D6_{192-206}$; $CYP2D6_{5-19}$; $CYP2D6_{293-307}$; $CYP2D6_{219-233}$; $CYP2D6_{237-251}$; $CYP2D6_{15-29}$; $CYP2D6_{235-249}$; $CYP2D6_{317-331}$; $CYP2D6_{293-307}$; $CYP2D6_{428-442}$; $CYP2D6_{237-251}$; $CYP2D6_{14-28}$: $CYP2D6_{199-213}$; $CYP2D6_{450-464}$; $CYP2D6_{301-315}$; $CYP2D6_{452-466}$; $CYP2D6_{59-73}$; $CYP2D6_{130-144}$; $CYP2D6_{193-212}$; $CYP2D6_{305-324}$; $CYP2D6_{15-29}$; and any combination thereof. In certain embodiments, the ubiquitous autoantigen is selected from the group consisting of: ACTB$_{202-216}$; ACTB$_{170-184}$; ACTB$_{245-259}$; ACTB$_{187-201}$; ACTB$_{172-186}$; ACTB$_{131-145}$; ACTB$_{131-145}$; ACTB$_{171-185}$; ACTB$_{129-143}$; ACTB$_{164-178}$; ACTB$_{25-39}$; ACTB$_{323-337}$; and any combination thereof. In certain embodiments, the ubiquitous autoantigen is selected from the group consisting of: ACTB$_{146-160}$; ACTB$_{18-32}$; ACTB$_{171-185}$; and any combination thereof. In certain embodiments, the ubiquitous autoantigen is selected from the group consisting of: SLA$_{334-348}$; SLA$_{196-210}$; SLA$_{115-129}$; SLA$_{373-386}$; SLA$_{186-197}$; SLA$_{342-256}$; SLA$_{110-124}$; SLA$_{299-313}$; SLA$_{49-63}$; SLA$_{260-274}$; SLA$_{119-133}$; SLA$_{86-100}$; SLA$_{26-40}$; SLA$_{331-345}$; SLA$_{317-331}$; SLA$_{171-185}$; SLA$_{417-431}$; SLA$_{359-373}$; SLA$_{215-229}$; SLA$_{111-125}$; and any combination thereof. In certain embodiments, the ubiquitous autoantigen is selected from the group consisting of: FTCD$_{439-453}$; FTCD$_{381-395}$; FTCD$_{297-311}$; FTCD$_{525-539}$; FTCD$_{218-232}$; FTCD$_{495-509}$: FTCD$_{262-276}$; FTCD$_{300-314}$; FTCD$_{259-273}$; FTCD$_{490-504}$; FTCD$_{389-403}$; FTCD$_{295-309}$; and any combination thereof. In certain embodiments, the ubiquitous autoantigen is selected from the group consisting of: FTCD$_{271-285}$; FTCD$_{498-512}$; FTCD$_{301-315}$; and any combination thereof. In certain embodiments, the ubiquitous autoantigen is selected from the group consisting of: MPO$_{322-336}$; MPO$_{714-728}$; MPO$_{617-631}$; MPO$_{504-518}$; MPO$_{462-476}$; MPO$_{617-631}$; MPO$_{444-458}$; MPO$_{689-703}$; MPO$_{248-262}$; MPO$_{511-525}$; MPO$_{97-111}$; MPO$_{616-630}$; and any combination thereof. In certain embodiments, described herein, is a composition comprising the uaMHC of the uaMHC-NP and a pharmaceutically acceptable stabilizer, excipient, diluent, or combination thereof. In certain embodiments, the composition is formulated for intravenous administration. In certain embodiments, the hepatic inflammatory disease is selected from the group consisting of hepatitis, non-alcoholic fatty liver disease (NAFLD), non-alcoholic steatohepatitis (NASH), cirrhosis, and pyogenic liver abscesses.

In another aspect described herein is a method of treating a hepatic inflammatory disease in an individual comprising administering to an individual a composition comprising: (a) a plurality of antigen-major histocompatibility complexes (antigen-MHCs), each antigen-MHC of the plurality comprising a ubiquitous autoantigen associated with a binding groove of an MHC molecule, wherein the ubiquitous autoantigen is not a tissue specific antigen; and (b) a nanoparticle core possessing a diameter of between 1 and about 100 nanometers; wherein the antigen-MHCs are coupled to the nanoparticle core or a biocompatible layer surrounding the nanoparticle core. In certain embodiments, the MHC molecule is an MHC class II molecule. In certain embodiments, the nanoparticle core is a metal or metal oxide. In certain embodiments, the metal is iron. In certain embodiments, the metal oxide is iron oxide. In certain embodiments the diameter is greater than 15 nanometers and no more than about 30 nanometers. In certain embodiments, the diameter is between about 5 nanometers and about 50 nanometers. In certain embodiments, the diameter is between about 5 nanometers and about 25 nanometers. In certain embodiments, the antigen-MHCs are coupled to the nanoparticle core at an antigen-MHC to nanoparticle core ratio of at least 10:1. In certain embodiments, the antigen-MHCs are coupled to the nanoparticle core at an antigen-MHC to nanoparticle core ratio of no more than about 150:1. In certain embodiments, the antigen-MHCs are coupled to the nanoparticle core at a density from about 0.4 to about 13 antigen-MHCs per 100 nm$^2$ of nanoparticle core surface area. In certain embodiments, the antigen-MHCs are covalently coupled to the nanoparticle core. In certain embodiments, the antigen-MHCs are coupled to the nanoparticle core by a polyethylene glycol (PEG) linker having a mass of less than about 5 kilodaltons. In certain embodiments, the nanoparticle core further comprises a biocompatible coating. In certain embodiments, the ubiquitous autoantigen comprises a polypeptide derived from a protein that at steady-state exists in or on an intracellular compartment. In certain embodiments, the intracellular compartment is cytosol, mitochondria, Golgi apparatus, endoplasmic reticulum, nucleus, or plasma membrane. In certain embodiments, the intracellular compartment is a mitochondrion. In certain embodiments, the ubiquitous autoantigen is pyruvate dehydrogenase complex-E2 component (PDC-E2) or a polypeptide derived therefrom. In certain embodiments, the ubiquitous autoantigen is Cytochrome P450 2D6 (CYP2D6) or a polypeptide derived therefrom. In certain embodiments, the ubiquitous autoantigen is actin (ACTB) or a polypeptide derived therefrom. In certain embodiments, the ubiquitous autoantigen is soluble liver antigen (SLA) or a polypeptide derived therefrom. In certain embodiments, the ubiquitous autoantigen is formimidoyltransferase-cyclodeaminase (FTCD) or a polypeptide derived therefrom. In certain embodiments, the ubiquitous autoantigen is myeloperoxidase (MPO) or a polypeptide derived therefrom. In certain embodiments, the ubiquitous autoantigen is selected from the group consisting of: PDC-E2$_{353-367}$; PDC-E2$_{72-86}$; PDC-E2$_{422-436}$; PDC-E2$_{353-367}$; PDC-E2$_{80-94}$; PDC-E2$_{535-549}$; PDC-E2$_{629-648}$; PDC-E2$_{122-135}$ PDC-E2$_{249-263}$; PDC-E2$_{249-263}$; and any combination thereof. In certain embodiments, the ubiquitous autoantigen is selected from the group consisting of: PDC-E2$_{422-436}$; PDC-E2$_{80-94}$, and the combination of PDC-E2$_{422-436}$ and PDC-E2$_{80-94}$. In certain embodiments, the ubiquitous autoantigen is selected from the group consisting of: CYP2D6$_{284-298}$; CYP2D6$_{289-303}$; CYP2D6$_{318-332}$; CYP2D6$_{313-332}$; CYP2D6$_{393-412}$; CYP2D6$_{192-206}$; CYP2D6$_{5-19}$CYP2D6$_{519}$; CYP2D6$_{293-307}$; CYP2D6$_{219-233}$; CYP2D6$_{237-251}$; CYP2D6$_{15-29}$; CYP2D6$_{235-249}$; CYP2D6$_{317-331}$; CYP2D6$_{293-307}$: CYP2D6$_{428-442}$; CYP2D6$_{237-251}$; CYP2D6$_{14-28}$; CYP2D6$_{199-213}$; CYP2D6$_{450-464}$; CYP2D6$_{301-315}$; CYP2D6$_{452-466}$; CYP2D6$_{59-73}$; CYP2D6$_{130-144}$; CYP2D6$_{193-212}$; CYP2D6$_{305-324}$; CYP2D6$_{15-29}$; and any combination thereof. In certain embodiments, the ubiquitous autoantigen is selected from the group consisting of: ACTB$_{202-216}$; ACTB$_{170-184}$; ACTB$_{245-259}$; ACTB$_{187-201}$; ACTB$_{172-186}$; ACTB$_{131-145}$; ACTB$_{131-145}$; ACTB$_{171-185}$; ACTB$_{129-143}$; ACTB$_{164-178}$; ACTB$_{25-39}$; ACTB$_{323-337}$; and any combination thereof. In certain embodiments, the ubiquitous autoantigen is selected from the group consisting of: ACTB$_{146-160}$; ACTB$_{18-32}$; ACTB$_{171-185}$; and any combination thereof. In certain embodiments, the ubiquitous autoantigen is selected from the group consisting of: SLA$_{334-348}$; SLA$_{196-210}$; SLA$_{115-129}$; SLA$_{373}$-386; SLA$_{186-197}$; SLA$_{342-256}$; SLA$_{110-124}$; SLA$_{299-313}$; SLA$_{49-63}$; SLA$_{260-274}$; SLA$_{119-133}$; SLA$_{86-100}$; SLA$_{26-40}$; SLA$_{331-345}$; SLA$_{317-331}$; SLA$_{171-185}$; SLA$_{417-431}$; SLA$_{359-373}$; SLA$_{215-229}$; SLA$_{111-125}$; and any combination thereof. In certain embodiments, the ubiquitous autoantigen is selected from the group consisting of: FTCD$_{439-453}$; FTCD$_{381-395}$; FTCD$_{297-311}$; FTCD$_{525-539}$; FTCD$_{218-232}$; FTCD$_{495-509}$: FTCD$_{262-276}$; FTCD$_{300-314}$; FTCD$_{259-273}$; FTCD$_{490-504}$; FTCD$_{389-403}$; and FTCD$_{295-309}$. In certain embodiments, the ubiquitous autoantigen is selected from the group consisting of: FTCD$_{271-285}$; FTCD$_{498-512}$; and FTCD$_{301-315}$; and any combination thereof. In certain embodiments, the ubiquitous autoantigen is selected from the group consisting of: MPO$_{322-336}$;

$MPO_{714-728}$; $MPO_{617-631}$; $MPO_{504-518}$; $MPO_{462-476}$; $MPO_{617-631}$; $MPO_{444-458}$; $MPO_{689-703}$; $MPO_{248-262}$; $MPO_{511-525}$; $MPO_{97-111}$; $MPO_{616-630}$; and any combination thereof. In certain embodiments, the composition further comprises a pharmaceutically acceptable stabilizer, excipient, diluent, or any combination thereof. In certain embodiments, the composition is formulated for intravenous administration. In certain embodiments, the hepatic inflammatory disease is selected from the group consisting of hepatitis, non-alcoholic fatty liver disease (NAFLD), non-alcoholic steatohepatitis (NASH), cirrhosis, and pyogenic liver abscesses.

BRIEF DESCRIPTION OF THE DRAWINGS

The novel features described herein are set forth with particularity in the appended claims. A better understanding of the features and advantages of the features described herein will be obtained by reference to the following detailed description that sets forth illustrative examples, in which the principles of the features described herein are utilized, and the accompanying drawings of which:

FIG. 1A shows percentage of tetramer+CD4+ T-cells in blood of NOD vs. NOD.c3c4 mice as a function of age. FIG. 1B shows percentage of tetramer+CD4+ T-cells in peripheral blood of pMHC-NP-treated NOD.c3c4 mice as compared to untreated NOD or NOD.c3c4 mice or NOD.c3c4 mice treated with control Cys-NPs. FIG. 1C shows percentages of tetramer+CD4+ T-cells in mice from panel B in various organs at the end of pMHC-NP therapy. FIG. 1D shows percentages of tetramer+CD4+ T-cells in NOD.c3c4 mice treated with type 1 diabetes-relevant pMHC-NPs. FIG. 1E shows percentages of tetramer+CD4+ T-cells in various lymphoid organs and liver of NOD.c3c4 mice treated with NPs coated with one of two different PBC-relevant pMHCs. FIG. 1F shows expression of TR1-like cell surface markers by the tetramer+CD4+ T-cells expanded in NOD.c3c4 mice by pMHC-NP therapy. FIG. 1G shows cytokine secretion profile of sorted tetramer+CD4+TR1-like cells vs. tetramer-negative CD4+ T-cells ex vivo upon stimulation with peptide-pulsed DCs.

(FIGS. 2A-B) Upregulation of TR1-like markers on tetramer+CD4+ T-cells expanded in vivo in response to $PDC_{166}/IA^{g7}$- or $PDC_{82}/IA^{g7}$-NP therapy. FIG. 2A is a representative FACS profiles. FIG. 2B shows average mean fluorescence intensity values. FIG. 2C shows average mean fluorescence intensity values for TR1 cell surface markers on tetramer+CD4+ T-cells arising in 38-44 week-old NOD.c3c4 mice in response to $PDC_{166}/IA^{g7}$-NP therapy.

FIG. 3A shows changes in serum TB and ALT levels with age. FIG. 3B shows microscopic scoring system (left) and progression of microscopic scores of disease with age (right). FIG. 3C shows representative CBD images and progression of CBD diameter and scores with age. FIG. 3D shows representative liver images (top) and progression of liver scores and weight with age (bottom). FIG. 3E shows that NOD.c3c4 mice spontaneously develop anti-PDC-E2-specific autoantibodies (left) and ANAs (right). FIG. 3F depicts representative images of liver inflammation by CD4+ and CD8+ T-cells.

FIG. 4A shows changes in total bile acid (TBA) and alanine aminotransferase (ALT) levels in serum of NOD.c3c4 mice treated with $PDC_{166}/IA^{g7}$-NPs, $PDC_{82}/IA^{g7}$-NPs or control (Cys-NP). FIG. 4B shows representative histological images of livers from $PDC_{166}/IA^{g7}$-NPs, $PDC_{82}/IA^{g7}$-NPs, or Cys-NP-treated NOD.c3c4 mice (top) and average histological scores (bottom). FIG. 4C shows representative macroscopic images of the common bile duct (top), and average common bile duct scores and diameters (bottom). FIG. 4D shows representative macroscopic images of livers (top) and average liver scores and weight (bottom). FIG. 4E shows representative whole body images of NOD.c3c4 mice treated with $PDC_{166}/IA^{g7}$-NP or control Cys-NPs. FIG. 4F shows changes in the titer of anti-mitochondrial (PDC-E2) antibodies and anti-nuclear autoantibodies (ANAs) after treatment (top left two panels and right panel, respectively), and representative images of Hep2 cells stained with sera from pMHC-NP vs Cys-NP-treated NOD.c3c4 mice (bottom). FIG. 4G shows percentages of tetramer+ cells in mice treated starting at 24 weeks of age (until week 38-44). FIGS. 4H and 4I show microscopic (FIG. 4H) and macroscopic scores (FIG. 4I) for the mice studied in FIG. 4G.

FIG. 5A shows two different mice, and FIG. 5B shows average values corresponding to cohorts of mice treated with $PDC_{166}/IA^{g7}$-NPs or left untreated. FIG. 5C shows percentage of tetramer+CD4+ T-cells, and FIG. 5D shows mean fluorescence intensity staining for TR1 markers in tetramer+CD4+ T-cells from the mice studied in FIG. 5A. FIG. 5E shows average macroscopic CBD and liver scores for the mice studied in FIGS. 5A-5D.

FIG. 6C shows percentages of tetramer+CD4+ T-cells in the mice studied in FIGS. 6A-6B. FIGS. 6D and 6E show effects of treatment with PBC-relevant pMHC-NPs or the standard of care in PBC (UDCA) on macroscopic (FIG. 6D) and microscopic (FIG. 6E) disease scores when treatment is initiated at advanced stages of disease. FIG. 6F shows percentages of tetramer+CD4+ T-cells in the mice studied in FIGS. 6D-6E.

FIG. 7A shows percentages of tetramer+CD4+ T-cells in mice treated with pMHC-NPs and rat-IgG (control) or blocking rat mAbs against mouse IL-10 or TGF-beta. FIGS. 7B and C show macroscopic (FIG. 7B) and microscopic (FIG. 7C) scores of the mice studied in FIG. 7A. FIG. 7D shows percentages of tetramer+CD4+ T cells in blood and lymphoid organs of NOD.c3c4.scid hosts reconstituted with whole splenocytes from untreated NOD.c3c4 donors and then transfused with splenic CD4+ T-cells from $PDC_{166-181}/IA^{g7}$-NP-treated NOD.c3c4 mice. The latter were either left untreated after CD4+ T-cell transfer or were treated with $PDC_{166}$-$181/IA^{g7}$-NPs. FIG. 7E shows representative FACS staining histograms (top) and average mean fluorescence intensity values for TR1 markers on tetramer+CD4+ vs. tetramer-CD4+ T-cells (bottom) of the hosts treated with $PDC_{166-181}/IA^{g7}$-NPs. FIG. 7F shows macroscopic scores and measurements of the mice studied in A. FIG. 7G shows the cytokine profile of LPS challenged CD11b+ cells isolated from the liver draining (PLN) or non-draining (MIN) lymph nodes of pMHC-NP vs Cys-NP-treated NOD.c3c4 mice. FIG. 7H shows the cytokine profile of liver Kupffer cells from pMHC-NP vs Cys-NP-treated NOD.c3c4 mice. FIG. 7I shows absolute numbers of B-cells in liver draining (PCLN) and non-draining (ILN) lymph nodes or liver of pMHC-NP vs Cys-NP-treated NOD.c3c4 mice. FIG. 7J shows correlation between absolute numbers of B-cells and tetramer+CD4+ T-cells in pMHC-NP-treated mice. (FIG. 7K shows IL-10 secretion levels of LPS-challenged B-cells isolated from liver draining and non-draining lymph nodes or liver of pMHC-NP vs Cys-NP-treated NOD.c3c4 mice. FIG. 7L shows representative FACS plots showing conversion of B cells into IL-10-producing Breg cells only in the experiments arising in in hosts treated with pMHC-NPs. FIG. 7M shows percentages of conventional B-cell-derived Breg cells in hosts treated with pMHC-NP or Cys-NP in liver and peripheral lymphoid organs harboring (spleen and PCLN) or lacking (MIN) pMHC-NP-induced TR1-like CD4+ T-cells.

FIG. 8A shows representative tetramer stains in NSG hosts engrafted with PBMC's from DRB4*0101+ PBC patients and treated with three different PBC-relevant pMHC-NPs. FIG. 8B shows average percentages and absolute numbers of tetramer+CD4+ cells in responsive vs. unresponsive pMHC-NP-treated mice or untreated littermates. FIG. 8C shows mean fluorescence intensity values (top) and two-dimensional FACS plots (bottom) for the TR1 markers CD49b and LAG3 in the mice studied in FIGS. 8A-B.

FIG. 9A shows percentage of tetramer+CD4+ T-cells in NOD.Abcb4−/− mice in response to pMHC-NP therapy. FIG. 9B shows average Primary Sclerosing Cholangitis scores (top) and representative H&E stained or picrosirius-stained liver sections (bottom), and TBA and ALT (right column) corresponding to the mice studied in FIG. 10A. FIG. 9C shows percentage of tetramer+CD4+ T-cells in NOD mice infected with an hFTCD-encoding Adenovirus (developing AIH) and treated with three different pMHC-NP types. FIG. 9D shows autoimmune hepatitis histopathological scores (top) and representative H&D and picrosirius liver stained sections (bottom) for the mice studied in FIG. 9C. FIG. 9E shows serum ALT levels in the mice in FIG. 9C [n=11, 5, 9 and 10) mice (left to right); 2-3 experiments].

FIG. 10A shows representative FACS staining histograms, and FIG. 10B shows average mean fluorescence intensity values for TR1 markers on tetramer+CD4+ vs. tetramer-CD4+ T-cells of NOD.Abcb4−/− mice (spontaneously developing PSC) treated with PBC- or AIH-relevant pMHC-NPs.

FIG. 11A shows representative FACS staining histograms, and FIG. 11B shows average mean fluorescence intensity values for TR1 markers on tetramer+CD4+ vs. tetramer-CD4+ T-cells of NOD mice infected with an adenovirus encoding hFTCD (spontaneously developing AIH) treated with PBC- or AIH-relevant pMHC-NPs.

FIG. 12A shows percentage of tetramer+CD4+ T-cells in NOD.c3c4 mice treated with an AIH relevant pMHC-NP type. FIG. 12B shows average macroscopic liver scores in NOD.c3c4 mice treated with PBC-AIH- or TID-relevant pMHC-NP types. FIG. 12C shows percentage of tetramer+CD4+ T-cells in NOD mice treated with PBC- or AIH-relevant pMHC-NP types.

FIG. 13A shows percentages of tetramer+CD4+ T-cells in mice (males and females pooled) treated with Cys-NPs or $PDC_{166-181}/IA^{g7}$-NPs. FIG. 13B shows serum TBA and ALT levels in the mice studied in A. FIG. 13C shows microscopic scores of the female mice studied in A (left) and representative H&E (top right) and picrosirius-red-stained liver sections (bottom right). Data in FIGS. 13A-13C correspond to n=7 and 12 mice/treatment type, respectively, from 2-3 experiments.

FIG. 14A shows an alpha chain of an MHC class II dimer fused to the $CH_2$ and $CH_3$ domain of an immunoglobulin molecule comprising an engineered knob (SEQ ID NO: 100).

Figure 1A:
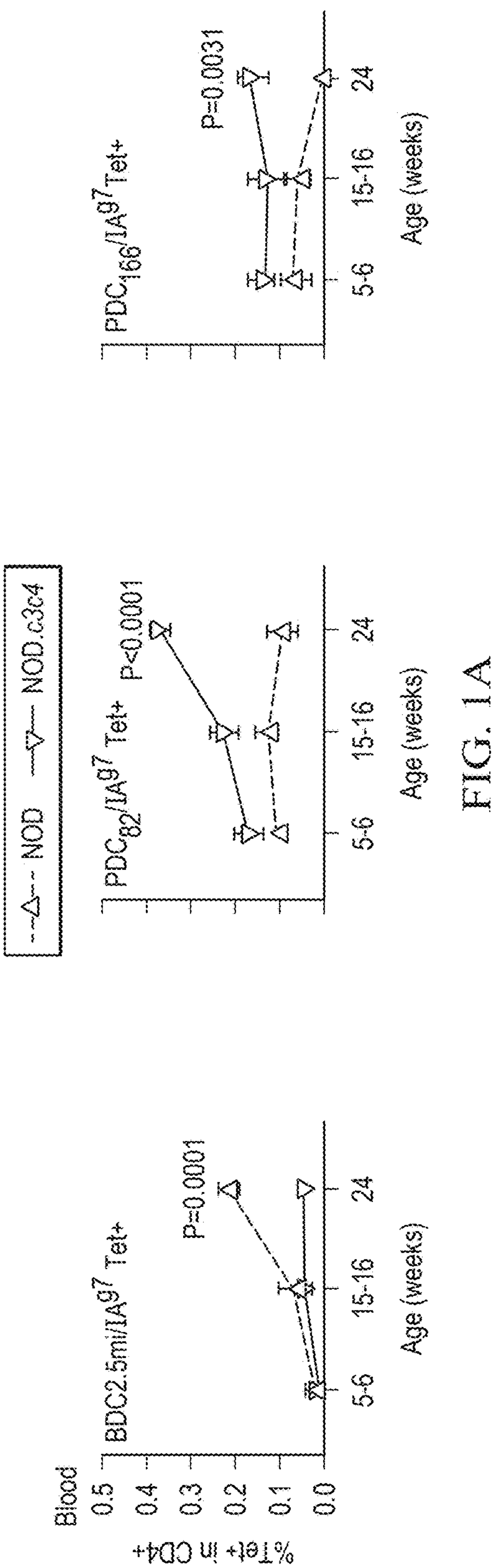
FIGS. 1A-1G illustrate the expansion of Primary Biliary Cirrhosis (PBC) relevant regulatory T cells by nanoparticles coupled to MHC class II associated with peptides derived from pyruvate dehydrogenase complex-E2 component (PDC-E2) (PBC-relevant peptide-major histocompatibility complex-nanoparticles (pMHC-NPs)).

TABLE 1 illustrates linkers useful for coupling ubiquitous autoantigen-MHCs to nanoparticles.

TABLES 2, 3, and 4 illustrate percentages and absolute numbers of tetramer+CD4+ T-cells in NSG mice engrafted with PBMCs from DRB4*0101+ PBC patients, upon treatment with three different human PBC-relevant pMHC-NP types.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

The use of the terms “a” and “an” and “the” and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., “such as”) provided herein, is intended merely to better illuminate the embodiments and does not pose a limitation on the scope of the claims unless otherwise stated. No language in the specification should be construed as indicating any non-claimed element as essential.

"Antigen" as used herein refers to all, part, fragment, or segment of a molecule that can induce an immune response in a subject or an expansion of an immune cell, preferably a T or B cell. Antigens can be polypeptides, lipids, carbohydrates, or nucleic acids.

As used herein "individual" is synonymous with "subject" or "patient". The individual can be diagnosed with a disease. The individual can suspected of having a particular disease based on manifesting at least one symptom of said disease, having a family history of said disease, having a genotype relevant to define risk for said disease, or having one or more phenotypic measurements or "lab tests" at or near a level that would place an individual at risk for the disease. The individual can be a mammal, such as a horse, cat, dog, pig, cow, goat, or sheep. The individual can in certain instances be a human person.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, "polypeptide" refers to a plurality of amino acids joined by peptide bonds having more than about eight amino acid residues. The amino acids of the polypeptide can be naturally occurring or unnatural amino acid residues.

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are known for instance, using publicly available computer software such as BLAST, BLAST-2, ALIGN or Megalign (DNASTAR) software. Appropriate parameters for aligning sequences are able to be determined, including algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The uaMHC or the uaMHC-NP of the current disclosure, described herein, can be encoded by a nucleic acid. A nucleic acid is a type of polynucleotide comprising two or more nucleotide bases. In certain embodiments, the nucleic acid is a component of a vector that can be used to transfer the polypeptide encoding polynucleotide into a cell. As used herein, the term "vector" refers to a nucleic acid molecule capable of transporting another nucleic acid to which it has been linked. One type of vector is a genomic integrated vector, or "integrated vector," which can become integrated into the chromosomal DNA of the host cell. Another type of vector is an "episomal" vector, e.g., a nucleic acid capable of extra-chromosomal replication. Vectors capable of directing the expression of genes to which they are operatively linked are referred to herein as "expression vectors." Suitable vectors comprise plasmids, bacterial artificial chromosomes, yeast artificial chromosomes, viral vectors and the like. In the expression vectors regulatory elements such as promoters, enhancers, polyadenylation signals for use in controlling transcription can be derived from mammalian, microbial, viral or insect genes. The ability to replicate in a host, usually conferred by an origin of replication, and a selection gene to facilitate recognition of transformants may additionally be incorporated. Vectors derived from viruses, such as lentiviruses, retroviruses, adenoviruses, adeno-associated viruses, and the like, may be employed. Plasmid vectors can be linearized for integration into a chromosomal location. Vectors can comprise sequences that direct site-specific integration into a defined location or restricted set of sites in the genome (e.g., AttP-AttB recombination). Additionally, vectors can comprise sequences derived from transposable elements.

Any of the nucleic acids encoding the uaMHC or the vectors comprising said nucleic acids can be transferred to a suitable cell line for the production of uaMHC. In certain embodiments, the nucleic acid or vector is stably integrated into the genome of the cell line. Suitable cell lines can be, e.g., Vero cells (ATCC CRL, 81), CHO-K1 (ATCC CRL 61) cells, Hela cells or L cells. Exemplary eukaryotic cells that can be used to express polypeptides include, but are not limited to, COS cells, including COS 7 cells; 293 cells, including 293-6E cells; CHO cells, including CHO-S and DG44 cells; PER.C6™ cells (Crucell); and NSO cells.

In one aspect described herein is a composition for use in treating a hepatic inflammatory disease, the composition comprising: (a) a plurality of antigen-major histocompatibility complexes (antigen-MHCs), each antigen-MHC of the plurality comprising a ubiquitous autoantigen associated with a binding groove of an MHC molecule, wherein the ubiquitous autoantigen is not liver specific antigen; and (b) a nanoparticle core possessing a diameter of between 1 and about 100 nanometers; wherein the antigen-MHCs are coupled to the nanoparticle core or a biocompatible layer surrounding the nanoparticle core.

In another aspect described herein is a method of treating a hepatic inflammatory disease in an individual comprising administering to an individual a composition comprising: (a) a plurality of antigen-major histocompatibility complexes (antigen-MHCs), each antigen-MHC of the plurality comprising a ubiquitous autoantigen associated with a binding groove of an MHC molecule, wherein the ubiquitous autoantigen is not a tissue specific antigen; and (b) a nanoparticle core possessing a diameter of from about 1 to about 100 nanometers; wherein the antigen-MHCs are coupled to the nanoparticle core or a biocompatible layer surrounding the nanoparticle core.

Ubiquitous Autoantigens

Described herein are nanoparticle compositions and methods useful for treating hepatic inflammatory disorders. The nanoparticle compositions comprise a plurality of antigens associated with MHCs coupled to a nanoparticle. The nanoparticle compositions and methods utilize broadly expressed ubiquitous autoantigens to elicit the generation of regulatory T and B lymphocytes.

In a certain aspect, the antigens that are associated with the MHC molecules are ubiquitous autoantigens or a polypeptide derived from a ubiquitous autoantigen. Ubiquitous autoantigens are differentiated from tissue specific antigens at least in that they are antigens commonly expressed by a plurality of different cell types that are unrelated. In certain embodiments, a ubiquitous autoantigen is one that is commonly expressed by ontogenically distinct tissues. In certain embodiments, a ubiquitous autoantigen is one that is expressed in at least two cell types derived from a tissue originating from the list consisting of ectoderm, mesoderm, and endoderm. In certain embodiments, a ubiquitous autoantigen is one that is commonly expressed by functionally distinct tissues. In certain embodiments, a ubiquitous autoantigen is one that is expressed in at least two tissues selected from the list consisting of neural tissue, endocrine tissue, connective tissue, hematopoietic cells, liver tissue, cardiac tissue, skin tissue, lung tissue, vascular tissue, intestinal tissue, and stomach tissue. In certain embodiments, a ubiquitous autoantigen is one that is expressed in both neural tissue and liver tissue. In certain embodiments, a ubiquitous autoantigen is one that is expressed in both neural tissue and pancreatic tissue. In a certain embodiment, the ubiquitous autoantigen is a polypeptide derived from a protein that participates in a cellular process common to at least 1, 2, 3, 4, 5, 6, 7, 8, 9, 10, or more cell types. Ubiquitous autoantigens may be sequences that are common to two or more closely related proteins that are recognized as being paralogs or homologs in the same family, yet display differential expression across various tissues. In certain embodiments, the two or more closely related proteins can for example, perform the same or similar function in two different unrelated tissues. In a certain embodiment, the ubiquitous autoantigen is a polypeptide derived from a protein that participates in a cellular process, wherein the cellular process is a metabolic process selected from glycolysis, oxidative phosphorylation, glycogenesis, nucleotide biosynthesis, beta oxidation, and omega oxidation. In certain embodiments, the ubiquitous autoantigen is selected from the list consisting of pyruvate dehydrogenase complex-E2 component (PDC-E2), Cytochrome P450 2D6 (CYP2D6), formimidoyltransferase-cyclodeaminase (FTCD, also referred to as formiminotransferase cyclodeaminase), soluble liver antigen (SLA), actin (ACTB), and myeloperoxidase (MPO).

Ubiquitous autoantigens are often encoded by housekeeping genes that are utilized in a variety of cell types. For example, actin is a cytoskeletal protein that contributes to cell structure, motility, cell division, and vesicle motility, and is also ubiquitously expressed. As such, many ubiquitous autoantigens are intracellular and reside in a particular intracellular compartment at a steady-state. An antigen exists at steady-state in the cellular location where the antigen can be found at its highest quantities, determined, for example, by microscopy or cell fractionation. For example, despite the fact that actin can be found extracellularly associated with exosomes the vast majority of actin is found in the cytosol of the cell. Likewise, many antigens may transit through different organelles but reside primarily in a single organelle. For example, many endoplasmic reticulum (ER) resident proteins will transiently transit through the cis-Golgi, but are immediately returned to the ER, where they reside at steady-state.

In certain embodiments, the ubiquitous autoantigens for use with the nanoparticle compositions described herein are polypeptides derived from pyruvate dehydrogenase complex-E2 component (PDC-E2). In certain embodiments, the polypeptide derived from PDC-E2 is any one or more of: PDC-E2$_{353-367}$, PDC-E2$_{72-86}$ and PDC-E2$_{422-436}$ for DRB3*0202; PDC-E2$_{353-367}$, PDC-E2$_{80-94}$ and PDC-E2$_{535-549}$ for DRB5*0101; PDC-E2$_{629-648}$, PDC-E2$_{122-135}$ and PDC-E2$_{249-263}$ for DRB4*0101; and PDC-E2$_{249-263}$ for DRB1*0801. In certain embodiments, the polypeptide derived from PDC-E2 is any one or more of: PDC-E2$_{422-436}$ and PDC-E2$_{80-94}$. In certain embodiments, the polypeptide derived from PDC-E2 is any one or more of: SEQ ID NOs: 1 to 12.

In certain embodiments, the ubiquitous autoantigens for use with the nanoparticle compositions described herein are polypeptides derived from Cytochrome P450 2D6 (CYP2D6). In certain embodiments, the polypeptide derived from CYP2D6 is any one or more of: CYP2D6$_{284-298}$, CYP2D6$_{289-303}$, CYP2D6$_{318-332}$, CYP2D6$_{313-332}$, CYP2D6$_{393-412}$, CYP2D6$_{192-206}$, CYP2D6$_{5-19}$, CYP2D6$_{293-307}$ (for DRB1*0301); CYP2D6$_{219-233}$, CYP2D6$_{237-251}$, CYP2D6$_{15-29}$ (for DRB3*0202); CYP2D6$_{235-249}$, CYP2D6$_{317-331}$, CYP2D6$_{293-307}$ (for DRB4*0) 101); CYP2D6$_{428-442}$, CYP2D6$_{237-251}$, CYP2D6$_{14-28}$ (for DRB5*0) 101); CYP2D6$_{199-213}$, CYP2D6$_{450-464}$, CYP2D6$_{301-315}$ (for DRB1*0) 401); CYP2D6$_{452-466}$, CYP2D6$_{59-73}$, CYP2D6$_{130-144}$, CYP2D6$_{193-212}$, CYP2D6$_{305-324}$, and CYP2D6$_{15-29}$ (for DRB1*0701). In certain embodiments, the polypeptide derived from CYP2D6 is any one or more of: SEQ ID NOs: 13 to 37.

In certain embodiments, the ubiquitous autoantigens for use with the nanoparticle compositions described herein are polypeptides derived from soluble liver antigen (SLA). In certain embodiments, the polypeptide derived from SLA is any one or more of: SLA$_{334-348}$, SLA$_{196-210}$, SLA$_{115-129}$, SLA$_{373-386}$, SLA$_{186-197}$ (for DRB1*0301); SLA$_{342-256}$, SLA$_{110-124}$, SLA$_{299}$-313 (for DRB3*0202); SLA$_{49-63}$, SLA$_{260-274}$, SLA$_{119-133}$ (for DRB4*0) 101); SLA$_{86-100}$, SLA$_{26-40}$, SLA$_{331-345}$ (for DRB5*0) 101); SLA$_{317-331}$, SLA$_{171-185}$, SLA$_{417-431}$ (for DRB1*0401); SLA$_{359-373}$, SLA$_{215-229}$, and SLA$_{111-125}$ (for DRB1*0) 701). In certain embodiments, the polypeptide derived from SLA is any one or more of: SEQ ID NOs: 53 to 72.

In certain embodiments, the ubiquitous autoantigens for use with the nanoparticle compositions described herein are polypeptides derived from actin (ACTB). In certain embodiments, the polypeptide derived from ACTB is any one or more of: ACTB$_{202-216}$, ACTB$_{170-184}$, ACTB$_{245-259}$, (for DRB1*0301); ACTB$_{187-201}$, ACTB$_{172-186}$, ACTB$_{131-145}$ (for DRB3*0) 202); ACTB$_{131-145}$, ACTB$_{171-185}$, ACTB$_{129-143}$ (for DRB4*0101); ACTB$_{164-178}$, ACTB$_{25}$-39, and ACTB$_{323-337}$ (for DRB5*0) 101). In certain embodiments, the polypeptide derived from ACTB is any one or more of: ACTB$_{146-160}$, ACTB$_{18-32}$, and ACTB$_{171-185}$. In certain embodiments, the polypeptide derived from ACTB is any one or more of: SEQ ID NOs: 38 to 52.

In certain embodiments, the ubiquitous autoantigens for use with the nanoparticle compositions described herein are polypeptides derived from formimidoyltransferase-cyclodeaminase (FTCD). In certain embodiments, the polypeptide derived from FTCD is any one or more of: $FTCD_{439-453}$, $FTCD_{381-395}$, $FTCD_{297-311}$ (for DRB3*0202); $FTCD_{525-539}$, $FTCD_{218-232}$, $FTCD_{495-509}$ (for DRB1*0301); $FTCD_{262-276}$, $FTCD_{300-314}$, $FTCD_{259-273}$ (for DRB4*0101); $FTCD_{490-504}$, $FTCD_{389-403}$, and $FTCD_{295-309}$ (for DRB5*0) 101). In certain embodiments, the polypeptide derived from FTCD is any one or more of: $FTCD_{271-285}$, $FTCD_{498-512}$, and $FTCD_{301-315}$. In certain embodiments, the polypeptide derived from FTCD is any one or more of: SEQ ID NOs: 73 to 87.

In certain embodiments, the ubiquitous autoantigens for use with the nanoparticle compositions described herein are polypeptides derived from myeloperoxidase (MPO). In certain embodiments, the polypeptide derived from MPO is any one or more of: $MPO_{322-336}$, $MPO_{714-728}$, $MPO_{617-631}$ (for DRB3*0202); $MPO_{504-518}$, $MPO_{462-476}$, $MPO_{617-631}$ (for DRB1*0301); $MPO_{444-458}$, $MPO_{689-703}$, $MPO_{248-262}$ (for DRB4*0101); $MPO_{511-525}$, $MPO_{97-111}$, and $MPO_{616-630}$ (for DRB5*0101). In certain embodiments, the polypeptide derived from MPO is any one or more of: SEQ ID NOs: 88 to 99.

Additional ubiquitous autoantigens are listed in Table 5 at the end of this disclosure. In certain embodiments, the ubiquitous autoantigens for use with the nanoparticle compositions described herein are derived from a protein or polypeptide listed in Table 5. In certain embodiments, the ubiquitous autoantigen comprises a polypeptide derived from any one or more of: Mdh1; Actg1; Vim; Ldha; Gapdh; Ywhaz; Fabp3; Atox1; Prdx1; Txndc17; Nel; Hnrnpf; Cops9; Lsm5; Pena; Hnrnpa2b1; Tkt; Rbbp4; Rbbp7; Nme1; Rack1; Tfrc; Gab1; Lifr; Egfr; Tfrc: S100a6; Fadd; Cnrip1; Eps1511; Nptp; Hspe1; Bax; Hspa9; Gstp1; Ndufab1; Mdh2; Hspd1; Atp5f1a; Hspd1; Atp5f1e; Arf3; Arf4; Arf5; Dpy30; Pitpnb; Ap1b1; Arl1; Prre1; Copz1; Sar1b; Pormc1; Cyp2f2; Atp2a2; Fkbp2; Cyb5a; Erp44; Canx; Hsp90b1; Vcp; and Lman1. In certain embodiments, the ubiquitous autoantigens for use with the nanoparticle compositions described herein is derived from a human homolog to protein or polypeptide listed in Table 5. In certain embodiments, a homologue or human homologue is a protein or polypeptide that displays at least about 75%, 80%, 85%, 90%, 95%, or 98% identity to a protein listed in Table 5.

Tissue Specific Antigens

The nanoparticle compositions and methods described herein utilize ubiquitous autoantigens that are not tissue specific antigens. Many autoimmune or inflammatory diseases are associated with an immune response directed to a tissue specific antigen. This presents a problem for the production of a medicament to treat an autoimmune or inflammatory disease, since each disease requires a specific medicament that targets that antigen. Alternatively, nonspecific immune inhibitors can be used, but these are associated with significant systemic side-effects.

Tissue specific antigens are often expressed by a tissue or cell type affected by the autoimmune disease, for example a main pathological consequence of multiple sclerosis is demyelination of nervous system tissue; as a consequence tissue specific antigens for multiple sclerosis are largely restricted to the nervous system (e.g., myelin basic protein). Tissue specific antigens are those antigens that are associated with a specific cell or cell type. Tissue specific antigens can perform specialized functions or contribute to specialized tissue structures. In certain embodiments, a tissue specific antigen has expression restricted to any one of the following tissues: neural, kidney, cardiac, lung, liver, small intestine, colon, stomach, muscle, connective, and blood-vessel. In certain embodiments, a tissue specific antigen is restricted to expression of any one of the following cell types: beta cells, alpha cells, B lymphocytes, T lymphocytes, Schwann cells, adrenocortical cells.

Many tissue specific antigens may be expressed at a very low level in other cell or tissue types, but the main source of expression is one specific cell or tissue type. For example, a single cell or tissue type that displays cell specific or tissue type specific expression of a certain gene will express at least 10-fold, 50-fold, 100-fold, 500-fold, 1,000 fold or more of the gene at the mRNA or protein level than any other unrelated cell-type. Additionally, some tissue specific antigens will gain ectopic expression of a cell specific antigen under a pathogenic condition or by an exogenous stimulation. It is intended that merely because a different cell-type may gain ectopic expression under pathological or exogenous conditions the tissue specific nature of the antigen is not lost. For example, insulin is a tissue specific antigen produced by beta cells, yet due to genetic instability, some tumors (known as insulinomas) will express insulin, and under these types of circumstances insulin is still considered tissue specific.

Tissue specific antigens that are not ubiquitous autoantigens are primarily antigens associated with a particular tissue specific autoimmune or inflammatory disease.

In certain embodiments, the autoimmune or inflammatory disease is multiple sclerosis. In certain embodiments, the tissue specific antigen that is not a ubiquitous autoantigen is a polypeptide derived from myelin basic protein, myelin associated glycoprotein, myelin oligodendrocyte protein (MOG), proteolipid protein, oligodendrocyte myelin oligoprotein, myelin associated oligodendrocyte basic protein, oligodendrocyte specific protein, heat shock proteins, an oligodendrocyte specific protein, NOGO A, glycoprotein Po, peripheral myelin protein 22, and/or 2'3'-cyclic nucleotide 3'-phosphodiesterase.

In certain embodiments, the autoimmune or inflammatory disease is type I diabetes. In certain embodiments, the tissue specific antigen that is not a ubiquitous autoantigen is a polypeptide derived from pre-proinsulin, proinsulin, islet-specific glucose-6-phosphatase (IGRP), glutamate decarboxylase (GAD), islet cell autoantigen-2 (ICA2), and/or insulin.

In certain embodiments, the autoimmune or inflammatory disease is Pemphigus Foliaceus (PF) or Pemphigus Vulgaris (PV). In certain embodiments, the tissue specific antigen that is not a ubiquitous autoantigen is a polypeptide derived from desmoglein 3 (DG3) and/or desmoglein 1 (DG1).

In certain embodiments, the autoimmune or inflammatory disease is Neuromyelitis optica spectrum disorder (NMO). In certain embodiments, the tissue specific antigen that is not a ubiquitous autoantigen is a polypeptide derived from aquaporin 4 (AQP4).

In certain embodiments, the autoimmune or inflammatory disease is Arthritis. In certain embodiments, the tissue specific antigen that is not a ubiquitous autoantigen is a polypeptide derived from a heat shock protein, immunoglobulin binding protein, heterogeneous nuclear RNPs, annexin V, calpastatin, type II collagen, glucose-6-phosphate isomerase, elongation factor human cartilage gp39, mannose binding lectin, citrullinated vimentin, type II collagen, fibrinogen, alpha enolase, anti-carbamylated protein (anti-CarP), peptidyl arginine deiminase type 4 (PAD4), BRAF, fibrinogen gamma chain, inter-alpha-trypsin inhibitor heavy chain H1, alpha-1-antitrypsin, plasma protease C1 inhibitor, gelsolin, alpha 1-B glycoprotein, ceruloplasmin, inter-alpha-trypsin inhibitor heavy chain H4, complement factor H, alpha 2 macroglobulin, serum amyloid, C-reactive protein, serum albumin, fibrogen beta chain, serotransferin, alpha 2 HS glycoprotein, vimentin, and/or Complement C3.

In certain embodiments, the autoimmune or inflammatory disease is allergic asthma. In certain embodiments, the tissue specific antigen that is not a ubiquitous autoantigen is a polypeptide derived from DERPI and/or DERP2.

In certain embodiments, the autoimmune or inflammatory disease is inflammatory bowel disease. In certain embodiments, the tissue specific antigen that is not a ubiquitous autoantigen is a polypeptide derived from bacteroides integrase, flagellin, flagellin 2 (Fla-2/Fla-X), or uncharacterized *E. coli* protein (YIDX).

In certain embodiments, the autoimmune or inflammatory disease is systemic lupus erythematosus disease. In certain embodiments, the tissue specific antigen that is not a ubiquitous autoantigen is a polypeptide H4, H2B, H1', dsDNA, RNP, Smith (Sm), Sjogren's Syndrome-related Antigen A (SS-A)/Ro, Sjogren's Syndrome-related Antigen B (SS-B)/La, and/or histones. In some embodiments, SS-A includes, but is not limited to, RO60 and RO52. In some embodiments, histones include but are not limited to H4, H2B, H1.

In certain embodiments, the autoimmune or inflammatory disease is atherosclerosis. In certain embodiments, the tissue specific antigen that is not a ubiquitous autoantigen is a polypeptide derived from Apolipoprotein B (ApoB) and/or Apolipoprotein E (ApoE).

In certain embodiments, the autoimmune or inflammatory disease is chronic obstructive pulmonary disease (COPD). In certain embodiments, the tissue specific antigen that is not a ubiquitous autoantigen is a polypeptide derived from elastin.

In certain embodiments, the autoimmune or inflammatory disease is psoriasis. In certain embodiments, the tissue specific antigen that is not a ubiquitous autoantigen is a polypeptide derived from human adamis-like protein 5 (ATL5), cathelicidin antimicrobial peptide (CAP18), and/or ADAMTS-like protein 5 (ADMTSL5).

In certain embodiments, the autoimmune or inflammatory disease is uveitis. In certain embodiments, the tissue specific antigen that is not a ubiquitous autoantigen is a polypeptide derived from arrestin, human retinal S-antigen, and/or interphotoreceptor retinoid-binding protein (IRBP).

In certain embodiments, the autoimmune or inflammatory disease is Sjogren's syndrome. In certain embodiments, the tissue specific antigen that is not a ubiquitous autoantigen is a polypeptide derived from (SS-A)/Ro, (SS-B)/La, RO60, RO52, and/or muscarinic receptor 3 (MR3).

In certain embodiments, the autoimmune or inflammatory disease is scleroderma. In certain embodiments, the tissue specific antigen that is not a ubiquitous autoantigen is a polypeptide derived from centromere autoantigen centromere protein C (CENP-C), DNA topoisomerase I (TOP1), and/or RNA polymerase III.

In certain embodiments, the autoimmune or inflammatory disease is anti-phospholipid syndrome. In certain embodiments, the tissue specific antigen that is not a ubiquitous autoantigen is a polypeptide derived from beta-2-glycoprotein 1 (BG2P1 or APOH).

In certain embodiments, the autoimmune or inflammatory disease is stiff man syndrome. In certain embodiments, the tissue specific antigen that is not a ubiquitous autoantigen is a polypeptide derived from GAD65.

Antigen-Major Histocompatibility Complexes (MHCs)

The nanoparticle complexes of this disclosure comprise a nanoparticle core, with or without layers and/or coatings, coupled to a ubiquitous autoantigen-MHC. The individual MHC polypeptide(s) and the antigenic (e.g., polypeptide) components form a complex through covalent or non-covalent binding (e.g. through hydrogen bonds, ionic bonds, or hydrophobic bonds). The preparation of such complexes may require varying degrees of manipulation and such methods are well known in the literature. In some aspects, antigenic components can be associated non-covalently with the pocket portion of the MHC component by, for instance, mixing the MHC and antigenic components; this relies on the natural binding affinity between an MHC and an antigen. Alternatively, in some aspects, the MHC component may be covalently associated with the antigenic component using standard procedures, such as, but not limited to, the introduction of known coupling agents or photo affinity labelling (see e.g., Hall et al., Biochemistry 24:5702-5711 (1985)). In certain aspects, an antigenic component may be operatively coupled to the MHC component via peptide linkages or other methods discussed in the literature, including but not limited to, attachment via carbohydrate groups on the glycoproteins, including, e.g., the carbohydrate moieties of the alpha- and/or beta-chains. In particular embodiments, the antigenic component may be attached to the N-terminal or C-terminal end of an appropriate MHC molecule. Alternatively, in certain embodiments, the MHC complex may be recombinantly formed by incorporating the sequence of the antigenic component into a sequence encoding an MHC, such that both retain their functional properties.

Multiple ubiquitous autoantigen-MHCs may be coupled to the same nanoparticle core; these complexes, MHCs, and/or antigens may be the same or different from one another.

Major Histocompatibility Molecules

The ubiquitous autoantigens described herein are associated with MHC molecules (to form the ubiquitous autoantigen-MHC) and coupled to nanoparticles. The antigens are bound to the binding groove of the MHC molecule. MHC molecules primarily bind antigens that are polypeptides, but polypeptides can comprise modifications such as lipidation, glycosylation, phosphorylation and the like. The MHC molecule can be an MHC class I molecule (MHCI) or an MHC class II molecule (MHCII). MHC class I molecules bind polypeptides between 8-10 amino acid residues in their binding groove, as the binding groove is closed on either side. MHC class II molecules, including those described herein, bind polypeptides at least 8 amino acids residues in length, but can bind longer peptides, with lengths of 9, 10, 11, 12, 13, 14, 15, 16, 17, 18, 19 amino acid residues or longer, as the binding groove is open on either side.

For use with human individuals the MHC molecules utilized herein are human (also referred to as human leukocyte antigens, abbreviated "HLA"). In certain embodiments, the MHC class I molecule is a classical or a non-classical MHC class I molecule HLA-A, HLA-B, HLA-C, HLA-E, CD1d, or a fragment or biological equivalent thereof. In certain embodiments, the MHC class II molecule is an HLA-DRB1, HLA-DRB3, HLA-DRB4, HLA-DRB5, HLA-DQB1, or HLA-DPB1, or a fragment or biological equivalent thereof. In some embodiments, the antigen-MHC (pMHC) can be a single chain construct. In some embodiments, the pMHC can be a dual-chain construct. In the case of a class II MHC, the beta chain of HLA will generally be non-covalently bound with an appropriate alpha chain to form a dual chain heterodimer with the alpha chain paired to the beta chain. Generally, the alpha chain of the MHC class II exhibits a much lower degree of polymorphism, for example, the DR alpha chain.

Since MHC class II complexes are heterodimers comprising an alpha and a beta chain, the heterodimers can have problems forming under some conditions, or are inherently unstable in some circumstances. When MHC class II molecules are deployed in a method or composition herein, the MHC molecules can further comprise a knob-in-hole architecture. In general, the alpha or beta chain is fused to an antibody $C_H2$ and $C_H3$ domain that has been modified to comprise a protuberance, while the corresponding other alpha or beta chain of the heterodimer is fused to an antibody $C_H2$ and $C_H3$ domain that has been modified to comprise a cavity.

As used herein, "knob-in-hole" or "knob-into-hole" refers to a polypeptidyl architecture requiring a protuberance (or "knob") at an interface of a first polypeptide and a corresponding cavity (or a "hole") at an interface of a second polypeptide, such that the protuberance can be positioned in the cavity so as to promote heterodimer formation. Protuberances may be constructed by replacing small amino acid side chains from the interface of the first polypeptide with larger side chains (e.g., phenylalanine or tyrosine). Cavities of identical or similar size to the protuberances may be created in the interface of the second polypeptide by replacing large amino acid side chains with smaller ones (e.g., alanine or threonine). The protuberances and cavities can be made by synthetic means such as by altering the nucleic acid encoding the polypeptides or by peptide synthesis, using routine methods by one skilled in the art. In some embodiments, the interface of the first polypeptide is located on an Fc domain in the first polypeptide; and the interface of the second polypeptide is located on an Fc domain on the second polypeptide. Knob-in-hole heterodimers and methods of their preparation and use are disclosed in U.S. Pat. Nos. 5,731,168; 5,807,706; 5,821,333; 7,642,228; 7,695,936; 8,216,805; and 8,679,785; and in Merchant et al., Nature Biotechnology, 1998, 16:677-681, all of which are incorporated by reference herein in their entirety.

Alternatively or in addition any of the antigens described herein can comprise a cysteine residue that interacts with a cysteine residue (engineered or natural) of an MHC class II alpha or beta chain. This is commonly known as a cysteine trap.

A cysteine trap can be utilized to stabilize a heterodimer described herein. Cysteine trapping involves forming covalently joined polypeptide complexes from unbound polypeptide partners. In some embodiments, cysteine trapping comprises introducing a cysteine at a strategically selected position within the interaction interface of the polypeptide partners to form a stabilized polypeptide complex. In some embodiments, cysteine trapping may stabilize the polypeptide complex to favor a specific conformation and to prevent dissociation. Cysteine trapping is also referred to as disulfide trapping and disulfide crosslinking. Examples of methods and applications of cysteine trapping are reviewed in Kufareva, et al., Methods Enzymol. 570:389-420 (2016). In the context of MHC, a cysteine is engineered into a polypeptide that is known or suspected to associate in the binding groove of an MHC class II dimer. A cysteine is then engineered in or near the binding groove such that, when the polypeptide associates with the binding groove, the binding groove cysteine can come into proximity and form a disulfide linkage with a polypeptide cysteine.

Provided herein, in one aspect, are isolated heterodimers comprising at least one first polypeptide and at least one second polypeptide, wherein the first polypeptide and the second polypeptide meet at an interface, wherein the interface of the first polypeptide comprises an engineered protuberance which is positionable in an engineered cavity in the interface of the second polypeptide; and (i) the first polypeptide comprises an MHC class II α1 domain, an MHC class II α2 domain, or a combination thereof; and the second polypeptide comprises an MHC class II β1 domain, an MHC class II β2 domain, or a combination thereof; or (ii) the first polypeptide comprises an MHC class II β1 domain, an MHC class II β2 domain, or a combination thereof; and the second polypeptide comprises an MHC class II al domain, an MHC class II α2 domain, or a combination thereof. The first polypeptide, the second polypeptide, or both can comprise an antibody $C_H3$ domain fused to the polypeptide. Optionally, the first polypeptide, the second polypeptide, or both comprise an antibody $C_H2$ domain located between the MHC (a or β chain) and the $C_H3$ domain. In certain embodiments, the first polypeptide comprises an antibody $C_H3$ domain, and the antibody $C_H3$ domain comprises at least one mutation selected from the list consisting of S354C, T366W, and both S354C and T366W (EU numbering). In certain embodiments, the second polypeptide comprises an antibody $C_H3$ domain, and the antibody $C_H3$ domain comprises at least one mutation selected from the list consisting of Y349C, T366S, L368A, Y407V (EU numbering), and any combination thereof. In further embodiments, the isolated heterodimer comprises a ubiquitous autoantigen, optionally covalently bound to either the first or the second polypeptide. Optionally, the ubiquitous autoantigen comprises a cysteine residue that interacts with a cysteine residue in either the first or second polypeptide to create a cysteine trap.

In one aspect, one polypeptide of the heterodimer comprises an MHC class II al domain, an MHC class II α2 domain, or a combination thereof; and at least one engineered protuberance. In some embodiments, the at least one engineered protuberance is not located at the MHC class II al domain or the MHC class II α2 domain. In some embodiments, the engineered protuberance is located at an antibody $C_H3$ domain fused to the polypeptide. In some embodiments, the polypeptide optionally comprises an antibody $C_H2$ domain located between an MHC class II α2 domain and the $C_H3$ domain with an engineered protuberance. In certain embodiments, the polypeptide comprises an antibody $C_H3$ domain, and the antibody $C_H3$ domain comprises at least one mutation selected from the list consisting of S354C, T366W, and both S354C and T366W (EU numbering). In further embodiments, the polypeptide comprises a ubiquitous autoantigen. Optionally, the ubiquitous autoantigen comprises a cysteine residue that interacts with a cysteine residue in either an MHC al or B1 domain to create a cysteine trap.

In one aspect, one polypeptide of the heterodimer comprises an MHC class II β1 domain, an MHC class II β2 domain, or a combination thereof; and at least one engineered protuberance. In some embodiments, the at least one engineered protuberance is not located at the MHC class II β1 domain or the MHC class II β2 domain. In some embodiments, the engineered protuberance is located at an antibody $C_H3$ domain fused to the polypeptide. In some embodiments, the polypeptide optionally comprises an antibody $C_H2$ domain located between an MHC class II β2 domain and the $C_H3$ domain with an engineered protuberance. In certain embodiments, the polypeptide comprises an antibody $C_H3$ domain, and the antibody $C_H3$ domain comprises at least one mutation selected from the list consisting of S354C, T366W, and both S354C and T366W (EU numbering). In further embodiments, the polypeptide comprises a ubiquitous autoantigen. Optionally, the ubiquitous autoantigen comprises a cysteine residue that interacts with a cysteine residue in either an MHC al or B1 domain to create a cysteine trap.

In one aspect, one polypeptide of the heterodimer comprises an MHC class II al domain, an MHC class II α2 domain, or a combination thereof; and at least one engineered cavity. In some embodiments, the at least one engineered cavity is not located at the MHC class II al domain or the MHC class II α2 domain. In some embodiments, the engineered cavity is located at an antibody $C_H3$ domain fused to the polypeptide. In some embodiments, the polypeptide optionally comprises an antibody $C_H2$ domain located between an MHC class II α2 domain and the $C_H3$ domain with an engineered cavity. In certain embodiments, the polypeptide comprises an antibody $C_H3$ domain, and the antibody $C_H3$ domain comprises at least one mutation selected from the list consisting of Y349C, T366S, L368A, Y407V (EU numbering), and any combination thereof. In further embodiments, the polypeptide comprises a ubiquitous autoantigen. Optionally, the ubiquitous autoantigen comprises a cysteine residue that interacts with a cysteine residue in either an MHC al or β1 domain to create a cysteine trap.

In one aspect, one polypeptide of the heterodimer comprises an MHC class II β1 domain, an MHC class II β2 domain, or a combination thereof; and at least one engineered cavity. In some embodiments, the at least one engineered cavity is not located at the MHC class II β1 domain or the MHC class II β2 domain. In some embodiments, the engineered cavity is located at an antibody $C_H3$ domain fused to the polypeptide. In some embodiments, the polypeptide optionally comprises an antibody $C_H2$ domain located between an MHC class II β2 domain and the $C_H3$ domain with an engineered cavity. In certain embodiments, the polypeptide comprises an antibody $C_H3$ domain, and the antibody $C_H3$ domain comprises at least one mutation selected from the list consisting of Y349C, T366S, L368A, Y407V (EU numbering), and any combination thereof. In further embodiments, the polypeptide comprises a ubiquitous autoantigen. Optionally, the ubiquitous autoantigen comprises a cysteine residue that interacts with a cysteine residue in either an MHC al or β1 domain to create a cysteine trap.

Figure 14A:
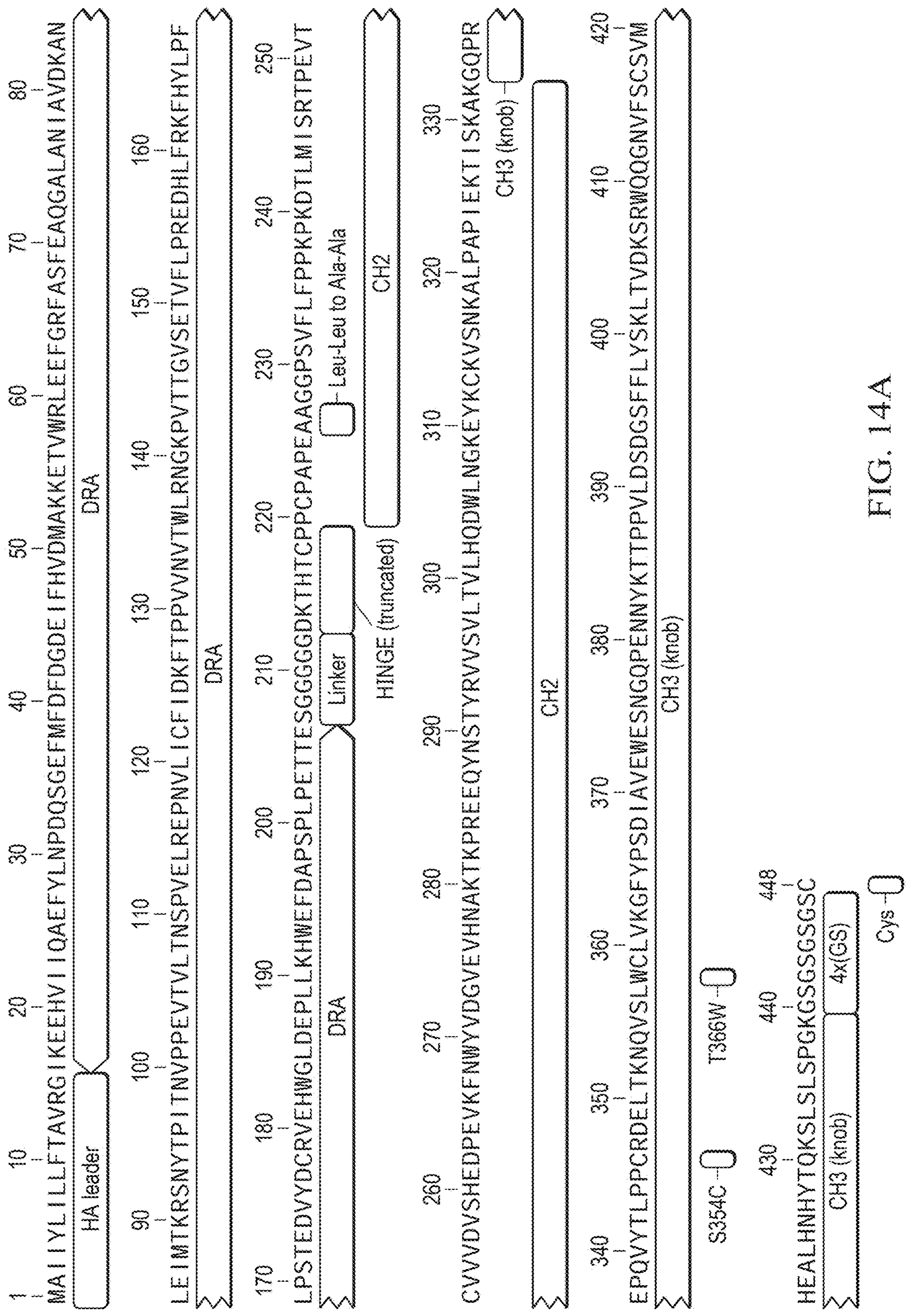
FIGS. 14A and B illustrate non-limiting embodiments of a pMHC-NP of this disclosure.
Figure 14B:
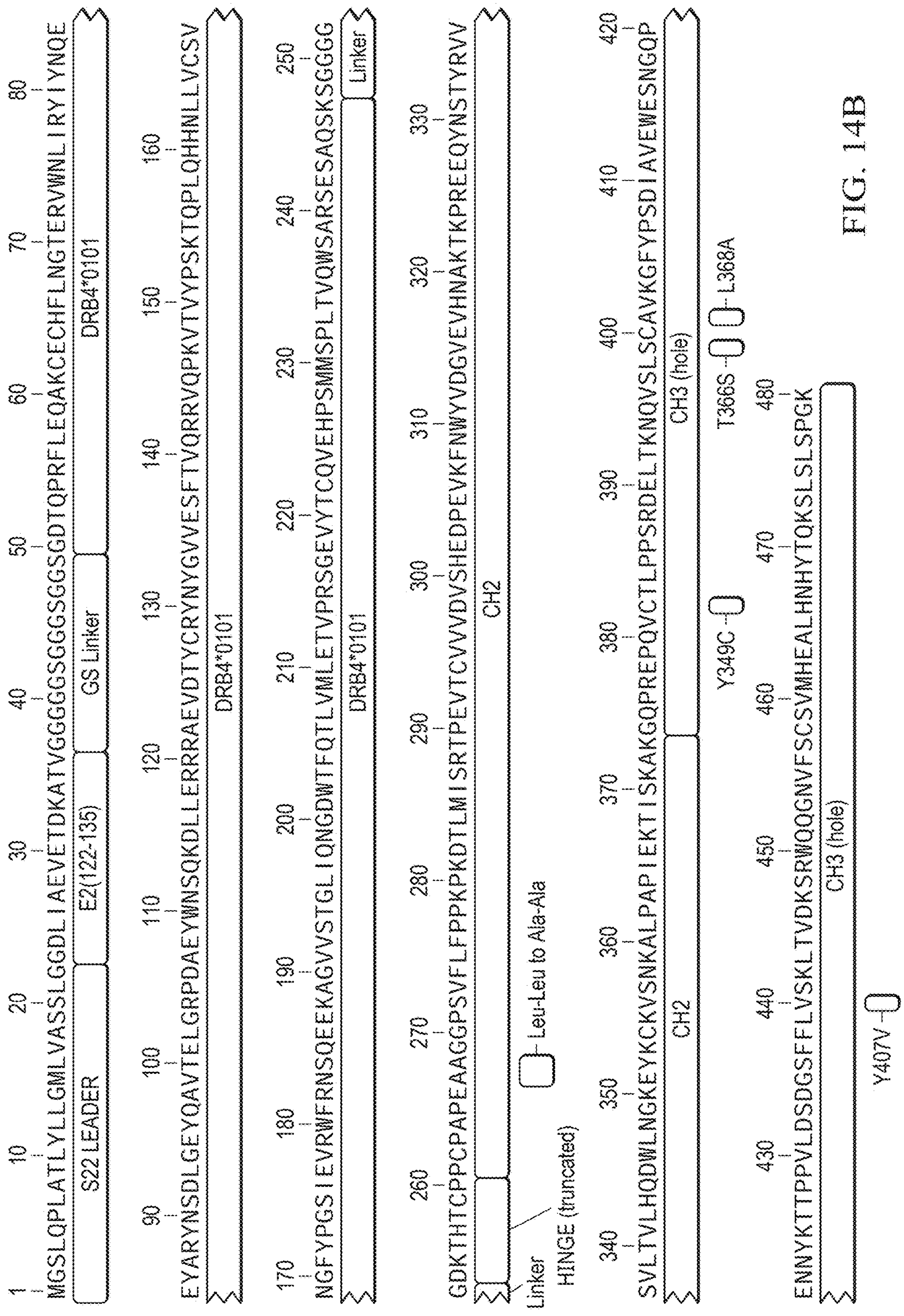
FIG. 14B shows a beta chain of an MHC class II with an N-terminal ubiquitous polypeptide (E2122-135), fused to the beta chain of the MHC class II, and fused to the $CH_2$ and $CH_3$ domains of an immunoglobulin molecule comprising an engineered hole (SEQ ID NO: 101).

FIGS. 14A and B show non-limiting embodiments of an engineered uaMHC comprising an engineered cavity and an engineered protuberance. FIG. 14A shows a human MHC class II alpha chain fused to an immunoglobulin $C_H2$ and $C_H3$ domain (SEQ ID NO: 100). The $C_H3$ domain comprises an engineered knob that has been created by substituting two amino acids S354C and T366W (SEQ ID NO: 104). The alpha chain comprises an optional c-terminal cysteine to allow for conjugation to a functionalized linker, however this c-terminal cysteine can be alternatively included on the beta chain. FIG. 14B shows a human MHC class II beta chain fused to an immunoglobulin $C_H2$ and $C_H3$ domain (SEQ ID NO: 101). The $C_H3$ domain comprises an engineered hole that has been created by substituting four amino acids-Y349C, T366S, L368A and Y407V (SEQ ID NO: 105). The beta chain also comprises a ubiquitous autoantigen (PDC-$E2_{122-135}$, SEQ ID NO: 8) that is covalently coupled to the beta chain by a peptide linker. The protuberance-cavity interaction favors assembly and allows for purification of intact uaMHC heterodimers using standard techniques to purify immunoglobulin. Once purified the uaMHC can be coupled to a suitable nanoparticle through a functionalized linker molecule (e.g., functionalized PEG molecules). In certain embodiments, the MHC heterodimer comprises amino acid sequences as set forth in SEQ ID NOS: 100 and 101. In certain embodiments, the MHC heterodimer comprises amino acid sequences at least about 90%, 95%, 97%, 98%, 99%, or 100% identical to SEQ ID NOS: 100 and 101. In certain embodiments, the alpha chain of the MHC heterodimer comprises an amino acid sequence at least about 90%, 95%, 97%, 98%, 99%, or 100% identical to SEQ ID NO: 102. In certain embodiments, the beta chain of the MHC heterodimer comprises an amino acid sequence at least about 90%, 95%, 97%, 98%, 99%, or 100% identical to SEQ ID NO: 103. In certain embodiments, the MHC heterodimer comprises an alpha chain at least about 90%, 95%, 97%, 98%, 99%, or 100% identical to SEQ ID NO: 102; and a beta chain at least about 90%, 95%, 97%, 98%, 99%, or 100% identical to SEQ ID NO: 103. In certain embodiments the MHC heterodimer comprises an alpha chain and beta chain at least about 90%, 95%, 97%, 98%, 99%, or 100% identical to SEQ ID NO: 102 and 103, respectively, and any one or more of the CH2 and CH3 domain of SEQ ID NO: 104, the CH2 and CH3 domain of SEQ ID NO: 105, and/or the ubiquitous autoantigen is identical to that disclosed in SEQ ID NO: 101 (separately disclosed as SEQ ID NO: 8). In certain embodiments the alpha chain and the beta chain are at least about 90%, 95%, 97%, 98%, 99%, or 100% identical to SEQ ID NO: 102 and 103, respectively, and the ubiquitous autoantigen is identical to that disclosed in SEQ ID NO: 101. In certain embodiments, the alpha chain of the MHC heterodimer comprises an amino acid sequence at least about 90%, 95%, 97%, 98%, 99%, or 100% identical to SEQ ID NO: 104. In certain embodiments, the beta chain of the MHC heterodimer comprises an amino acid sequence at least about 90%, 95%, 97%, 98%, 99%, or 100% identical to SEQ ID NO: 105. In certain embodiments, the alpha chain of the MHC heterodimer comprises an amino acid sequence at least about 90%, 95%, 97%, 98%, 99%, or 100% identical to SEQ ID NO: 104 while preserving specific knob or hole mutations. In certain embodiments, the beta chain of the MHC heterodimer comprises an amino acid sequence at least about 90%, 95%, 97%, 98%, 99%, or 100% identical to SEQ ID NO: 105 while preserving specific knob or hole mutations. Those of skill in the art will recognize that the alpha and beta chains of human MHC are highly polymorphic, and thus can tolerate a relatively high degree of variability. One of skill in the art will also be able to substitute the alpha and beta chains of the MHC shown in SEQ ID NOs: 102 and 103, respectively for a different HLA allele, and an appropriate ubiquitous autoantigen that is able to bind the specific substituted allele. Such HLA allele and ubiquitous autoantigen pairings are disclosed elsewhere in the application, for example, at the sequence listing at the end of this application.

Nanoparticles

The ubiquitous autoantigen-MHCs are coupled to a nanoparticle core (uaMHC-NP). The nanoparticle can be made from a variety of materials. In certain embodiments, the nanoparticle is non-liposomal and/or has a solid core. In certain embodiments, the solid core can be a metal or a metal oxide. In certain embodiments, the solid core can be iron, iron oxide, or gold. The solid core can be a high density core such that the density is greater than about 2.0 $g/cm^3$, about 3.0 $g/cm^3$, about 4.0 $g/cm^3$, about 5.0 $g/cm^3$, about 6.0 $g/cm^3$, or about 7.0 $g/cm^3$. In certain embodiments, the density of the solid core is between about 4.0 $g/cm^3$ and about 8.0 g/$cm^3$. In certain embodiments, the density of the solid core is between about 5.0 g/$cm^3$ and about 8.0 g/$cm^3$. In certain embodiments, the density of the solid core is between about 5.0 g/$cm^3$ and about 7.0 g/$cm^3$. In certain embodiments, the density of the solid core is between about 5.0 g/$cm^3$ and about 6.0 g/$cm^3$.

The nanoparticle core of the uaMHC-NP comprises, or consists essentially of, or yet further consists of a core, for example a solid core, a metal core, a dendrimer core, a polymeric micelle nanoparticle core, a nanorod, a fullerene, a nanoshell, a coreshell, a protein-based nanostructure or a lipid-based nanostructure. In some aspects, the nanoparticle core is bioabsorbable and/or biodegradable. In some aspects, the nanoparticle core is a dendrimer nanoparticle core comprising, or alternatively consisting essentially thereof, or yet further consisting of a highly branched macromolecule having a tree-like structure growing from a core. In further aspects, the dendrimer nanoparticle core may comprise, or alternatively consist essentially thereof, or yet further consist of a poly(amidoamine)-based dendrimer or a poly-1-lysine-based dendrimer. In certain aspects, the nanoparticle core is a polymeric micelle core comprising, or alternatively consisting essentially thereof, or yet further consisting of an amphiphilic block co-polymer assembled into a nano-scaled core-shell structure. In further aspects, the polymeric micelle core comprises, or alternatively consists essentially thereof, or yet further consists of a polymeric micelle produced using polyethylene glycol-diastearoylphosphatidylethanolamine block copolymer. In a further aspect, the nanoparticle core comprises, or alternatively consists essentially of, or yet further consists of a metal. In another aspect, the nanoparticle core is not a liposome. Additional examples of core materials include but are not limited to, standard and specialty glasses, silica, polystyrene, polyester, polycarbonate, acrylic polymers, polyacrylamide, polyacrylonitrile, polyamide, fluoropolymers, silicone, celluloses, silicon, metals (e.g., iron, gold, silver), minerals (e.g., ruby), nanoparticles (e.g., gold nanoparticles, colloidal particles, metal oxides, metal sulfides, metal selenides, and magnetic materials such as iron oxide), and composites thereof. In some embodiments, an iron oxide nanoparticle core comprises iron (II, III) oxide. The core could be of homogeneous composition, or a composite of two or more classes of material depending on the properties desired. In certain aspects, metal nanoparticles will be used. These metal particles or nanoparticles can be formed from Au, Pt, Pd, Cu, Ag, Co, Fe, Ni, Mn, Sm, Nd, Pr, Gd, Ti, Zr, Si, and In, precursors, their binary alloys, their ternary alloys and their intermetallic compounds. See U.S. Pat. No. 6,712,997, which is incorporated herein by reference for such disclosure. In certain embodiments, the compositions of the core and layers (described below) may vary provided that the nanoparticles are biocompatible and bioabsorbable. The core could be of homogeneous composition, or a composite of two or more classes of material depending on the properties desired. In certain aspects, metal nanospheres will be used. These metal nanoparticles can be formed from Fe, Ca, Ga and the like. In certain embodiments, the nanoparticle comprises, or alternatively consists essentially of, or yet further consists of a core comprising metal or metal oxide such as gold or iron oxide.

In another aspect, provided herein are uaMHC-NPs comprising at least one ubiquitous autoantigen-MHC described herein and a nanoparticle, wherein the nanoparticle is non-liposomal and has an iron oxide core.

In another aspect, provided herein are uaMHC-NPs comprising at least one ubiquitous autoantigen-MHC described herein and a nanoparticle, wherein the nanoparticle is non-liposomal and has a gold core.

In another aspect, provided herein are uaMHC-NPs comprising at least one ubiquitous autoantigen-MHC herein and a nanoparticle, wherein the nanoparticle is non-liposomal and has an iron oxide core; and the at least one ubiquitous autoantigen-MHC is covalently linked to the nanoparticle through a linker.

In some aspects, the nanoparticle core has a diameter selected from the group of from about 1 nm to about 100 nm; from about 1 nm to about 75 nm; from about 1 nm to about 50 nm; from about 1 nm to about 25 nm; from about 5 nm to about 100 nm; from about 5 nm to about 50 nm; from about 5 nm to about 40 nm; from about 5 nm to about 30 nm; from about 5 nm to about 25 nm; or from about 5 nm to about 20 nm. In some embodiments, the nanoparticle core has a dimeter from about 10 nm to about 100 nm; from about 10 nm to about 50 nm; from about 10 nm to about 40 nm; from about 10 nm to about 30 nm; from about 10 nm to about 25 nm; or from about 10 nm to about 20 nm. In certain embodiments, the nanoparticle core has a diameter greater than about 1 nm, 2 nm, 5 nm, 10 nm, 15 nm, 20 nm, 25 nm, 30 nm, 40 nm, or 50 nm. In certain embodiments, the nanoparticle core has a diameter less than about 100 nm, 75 nm, 50 nm, 40 nm, 30 nm, 20 nm, or 15 nm.

In some aspects, the nanoparticle core is a dendrimer nanoparticle core comprising, or alternatively consisting essentially thereof, or yet further consisting of a highly branched macromolecule having a tree-like structure growing from a core. In further aspects, the dendrimer nanoparticle may comprise, or alternatively consist essentially thereof, or yet further consist of a poly(amidoamine)-based dendrimer or a poly-L-lysine-based dendrimer. In certain aspects, the nanoparticle core is a polymeric micelle core comprising, or alternatively consisting essentially thereof, or yet further consisting of an amphiphilic block co-polymer assembled into a nano-scaled core-shell structure. In further aspects, the polymeric micelle core may comprise, or alternatively consist essentially thereof or yet further consist of, a polymeric micelle produced using polyethylene glycol-diastearoylphosphatidylethanolamine block copolymer. The dendrimer core or polymeric micelle core may further comprise an outer coating or layer as described herein.

In certain embodiments, specific means of synthesis of dendrimer nanoparticles or nanoparticles with a dendrimer nanoparticle core may require that metal ions are extracted into the interior of dendrimers and then subsequently chemically reduced to yield nearly size-monodispersed particles having dimensions of less than 3 nm, such as the method disclosed in Crooks et al., "Synthesis, Characterization, and Applications of Dendrimer-Encapsulated Nanoparticles". *The Journal of Physical Chemistry B* (109): 692-704 (2005), wherein the resulting dendrimer core component serves not only as a template for preparing the nanoparticle but also to stabilize the nanoparticle, making it possible to tune solubility, and provides a means for immobilization of the nanoparticle on solid supports.

The nanoparticle cores typically consist of a substantially spherical core and optionally one or more layers or coatings. The core may vary in size and composition as described herein. In addition to the core, the particle may have one or more layers to provide functionalities appropriate for the applications of interest. The thicknesses of layers, if present, may vary depending on the needs of the specific applications. For example, layers may impart useful optical properties.

Layers may also impart chemical or biological functionalities, referred to herein as chemically active or biologically active layers. These layers typically are applied on the outer surface of the particle and can impart functionalities to the pMHC-NPs. The layer or layers may typically range in thickness from about 0.001 micrometers (1 nanometer) to about 10 micrometers or more (depending on the desired particle diameter) or from about 1 nm to 5 nm, from about 1 nm to about 10 nm, from about 1 nm to about 40 nm, from about 15 nm to about 25 nm, or about 20 nm, and ranges in between.

The layer or coating may comprise, or alternatively consist essentially of, or yet further consist of a biodegradable sugar or other polymer. Examples of biodegradable layers include but are not limited to dextran; poly(ethylene glycol); poly(ethylene oxide); mannitol; poly(esters) based on polylactide (PLA), polyglycolide (PGA), polycaprolactone (PCL); poly(hydroxalkanoate) of the PHB-PHV class; and other modified poly(saccharides) such as starch, cellulose and chitosan. Additionally, the nanoparticle may include a layer with suitable surfaces for attaching chemical functionalities for chemical binding or coupling sites.

Surface Valency and Density of Antigen-MHCs

The ubiquitous autoantigen-MHCs described herein are coupled to the nanoparticle at a certain valency. Valency is the number of pMHCs per nanoparticle core. In certain embodiments, the valency of the nanoparticle may range between about 1 pMHC per nanoparticle core to about 6,000 pMHCs per nanoparticle core. In certain embodiments, the valency of the nanoparticle may range between about 10 pMHCs per nanoparticle core to about 6,000 pMHCs per nanoparticle core. In certain embodiments, the valency of the nanoparticle may range between about 50 pMHCs per nanoparticle core to about 6,000 pMHCs per nanoparticle core. In certain embodiments, the valency of the nanoparticle may range between about 1 pMHC per nanoparticle core to about 5000, about 4000, about 3000, about 2000, or about 1000 pMHCs per nanoparticle core. In certain embodiments, the valency of the nanoparticle may range between about 10 pMHCs per nanoparticle core to about 5000, about 4000, about 3000, about 2000, or about 1000 pMHCs per nanoparticle core. In certain embodiments, the valency of the nanoparticle may range between about 50 pMHC per nanoparticle core to about 5000, about 4000, about 3000, about 2000, or about 1000 pMHCs per nanoparticle core. In certain embodiments, the valency of the nanoparticle may range between about 1 pMHC to per nanoparticle core to about 1000 pMHCs per nanoparticle core, or between about 10:1 to about 1000:1, or between about 11:1 to about 1000:1, or between about 12:1 to about 1000:1. In certain embodiments, the valency (antigen-MHC to nanoparticle core) may range between about 10:1 to about 500:1, or between about 11:1 to about 500:1, or between about 12:1 to about 500:1. In certain embodiments, the valency (antigen-MHC to nanoparticle core) may range between about 10:1 to about 200:1, or between about 11:1 to about 200:1, or between about 12:1 to about 200:1. In certain embodiments, the valency (antigen-MHC to nanoparticle core) may range between about 10:1 to about 150:1, or between about 11:1 to about 150:1, or between about 12:1 to about 150): 1. In certain embodiments, the valency (antigen-MHC to nanoparticle core) may range between about 10:1 to about 100:1, or between about 11:1 to about 100:1, or between about 12:1 to about 100:1. In certain embodiments, the valency (antigen-MHC to nanoparticle core) may range between about 10:1 to about 200:1, between about 20:1 to about 200:1, between about 30:1 to about 200:1, between about 40:1 to about 200:1, or between about 50:1 to about 200:1. In certain embodiments, the valency (antigen-MHC to nanoparticle core) may range between about 10:1 to about 150:1, between about 20:1 to about 150:1, between about 30:1 to about 200:1, between about 40:1 to about 150:1, or between about 50:1 to about 150:1. In certain embodiments, the valency (antigen-MHC to nanoparticle core) may range between about 10:1 to about 100:1, between about 20:1 to about 100:1, between about 30:1 to about 100:1, between about 40:1 to about 100:1, or between about 50:1 to about 100:1.

In some aspects, the nanoparticle core has a defined valency per surface area of the core, also referred to herein as "density." In these aspects, the pMHC density per nanoparticle is from about 0.025 pMHC/100 $nm^2$ to about 100 pMHC/100 $nm^2$ of the surface area of the nanoparticle core, or alternatively from about 0.406 pMHC/100 $nm^2$ to about 50 pMHC/100 $nm^2$; or alternatively from about 0.05 pMHC/100 $nm^2$ to about 25 pMHC/100 $nm^2$. In certain aspects, the pMHC density per nanoparticle is from about 0.4 pMHC/100 $nm^2$ to about 25 pMHC/100 $nm^2$, or from about 0.4 pMHC/100 $nm^2$ to about 20 pMHC/100 $nm^2$, or from about 0.4 pMHC/100 $nm^2$ to about 15 pMHC/100 $nm^2$, or from about 0.4 pMHC/100 $nm^2$ to about 14 pMHC/100 $nm^2$, or from about 0.4 pMHC/100 $nm^2$ to about 13 pMHC/100 $nm^2$, or from about 0.4 pMHC/100 $nm^2$ to about 12 pMHC/100 $nm^2$, or from about 0.4 pMHC/100 $nm^2$ to about 11.6 pMHC/100 $nm^2$, or from about 0.4 pMHC/100 $nm^2$ to about 11.5 pMHC/100 $nm^2$, or from about 0.4 pMHC/100 $nm^2$ to about 11 pMHC/100 $nm^2$, or from about 0.4 pMHC/100 $nm^2$ to about 10 pMHC/100 $nm^2$, or from about 0.4 pMHC/100 $nm^2$ to about 9 pMHC/100 $nm^2$, or from about 0.4 pMHC/100 $nm^2$ to about 8 pMHC/100 $nm^2$, or from about 0.4 pMHC/100 $nm^2$ to about 7 pMHC/100 $nm^2$, or from about 0.4 pMHC/100 $nm^2$ to about 6 pMHC/100 $nm^2$, or from about 0.4 pMHC/100 $nm^2$ to about 5 pMHC/100 $nm^2$, or from about 0.4 pMHC/100 $nm^2$ to about 4 pMHC/100 $nm^2$, or from about 0.4 pMHC/100 $nm^2$ to about 3 pMHC/100 $nm^2$, or from about 0.4 pMHC/100 $nm^2$ to about 2.5 pMHC/100 $nm^2$, or from about 0.4 pMHC/100 $nm^2$ to about 2 pMHC/100 $nm^2$, or from about 0.4 pMHC/100 $nm^2$ to about 1.5 pMHC/100 $nm^2$.

In another aspect, the nanoparticle may have a pMHC density of from about 0.22 pMHC/100 $nm^2$ to about 10 pMHC/100 $nm^2$, or from about 0.22 pMHC/100 $nm^2$ to about 9 pMHC/100 $nm^2$, or from about 0.22 pMHC/100 $nm^2$ to about 8 pMHC/100 $nm^2$, or from about 0.22 pMHC/100 $nm^2$ to about 7 pMHC/100 $nm^2$, or from about 0.22 pMHC/100 $nm^2$ to about 6 pMHC/100 $nm^2$, or from about 0.22 pMHC/100 $nm^2$ to about 5 pMHC/100 $nm^2$, or from about 0.22 pMHC/100 $nm^2$ to about 4 pMHC/100 $nm^2$, or from about 0.22 pMHC/100 $nm^2$ to about 3 pMHC/100 $nm^2$, or from about 0.22 pMHC/100 $nm^2$ to about 2 pMHC/100 $nm^2$, or from about 0.22 pMHC/100 $nm^2$ to about 1.5 pMHC/100 $nm^2$. In some aspects, the nanoparticle has a pMHC density of from about 0.22 pMHC/100 $nm^2$ to about 10 pMHC/100 $nm^2$, or from 0.24 pMHC/100 $nm^2$ to about 9 pMHC/100 $nm^2$, or from about 0.26 pMHC/100 $nm^2$ to about 8 pMHC/100 $nm^2$, or from about 0.28 pMHC/100 $nm^2$ to about 7 pMHC/100 $nm^2$, or from about 0.24 pMHC/100 $nm^2$ to about 4 pMHC/100 $nm^2$, or from about 0.5 pMHC/100 $nm^2$ to about 3 pMHC/100 $nm^2$, or from about 0.6 pMHC/100 $nm^2$ to about 1.5 pMHC/100 $nm^2$. In a further aspect, the nanoparticle has a pMHC density of from about 0.4 pMHC/100 $nm^2$ to about 1.3 pMHC/100 $nm^2$, or alternatively from about 0.5 pMHC/100 $nm^2$ to about 0.9 pMHC/100 $nm^2$, or alternatively from about 0.6 pMHC/100 $nm^2$ to about 0.8 pMHC/100 $nm^2$.

Linkers

In certain aspects, ubiquitous autoantigen-MHC can be coupled to the nanoparticle core by one or more of covalently, non-covalently, or cross-linked; and optionally coupled through a linker. In aspects involving a linker or linkers, the linkers may be the same or different from each other on a single nanoparticle core. In some embodiments, the ubiquitous autoantigen-MHC comprises at least one ubiquitous autoantigen-MHC described herein and a nanoparticle, wherein the nanoparticle is non-liposomal and has metal or metal oxide core; and the at least one ubiquitous autoantigen-MHC is covalently linked to the nanoparticle through a linker comprising polyethylene glycol with a molecular weight of less than 5 kilodaltons (kD). In some embodiments, polyethylene glycol has a molecular weight of less than 1 kD, 2 kD, 3 kD, 4 kD, 5 kD, 6 kD, 7 kD, 8 kD, 9 kD, or 10 kD. In some embodiments, polyethylene glycol is functionalized with maleimide. In some embodiments, polyethylene glycol has a molecular weight of between about 1 kD and about 5 kD, between about 2 kD and about 5 kD, between about 3 kD and about 5 kD. In some embodiments, polyethylene glycol is functionalized with maleimide. In certain embodiments, the end of the linker that is in contact with the solid core is embedded in the solid core. In further aspects, the linker may be less than 5 kD in size, and is optionally polyethylene glycol. The linker can be any of the linkers described in Table 1.

TABLE 1

Exemplary linker molecules

| Types of Nanoparticle | PEG linkers | M.W. (kD) | Functional group | Structure |
|---|---|---|---|---|
| Gold nanoparticle (GNP-C) | Thiol-PEG-carboxyl | 3.5 | Carboxyl (—COOH) | 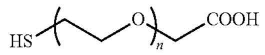 |
| Gold nanoparticle (GNP-N) | Thiol-PEG-amine | 3.5 | Amine (—$NH_2$) | 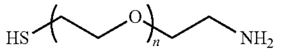 |
| Iron oxide Nanoparticle (SFP-C) | Dopamine-PEG-carboxyl | 3.5 | Carboxyl (—COOH) | 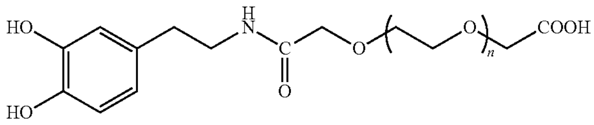 |
| Iron oxide Nanoparticle (SFP-N) | Dopamine-PEG-amine | 3.5 | Amine (—$NH_2$) | 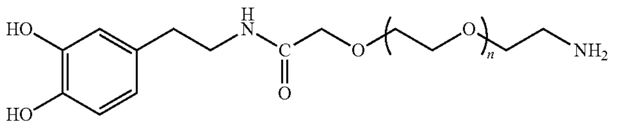 |
| Iron oxide Nanoparticle (SFP-Z) | Dopamine-PEG-azide | 3.5 | Azide (—$N_3$) | 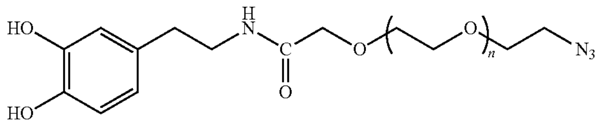 |
| Iron oxide Nanoparticle (SFP-M) | Dopamine-PEG-maleimide | 3.5 | Maleimide | 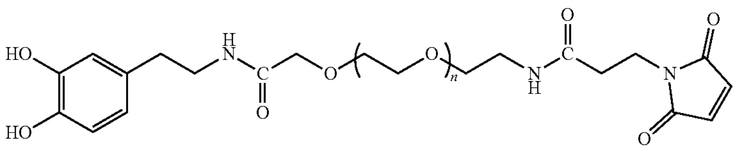 |
| Iron oxide Nanoparticle (SFP-O) | Dopamine-PEG-Orthopyridyl disulfide | 3.5 | Orthopyridyl disulfide | 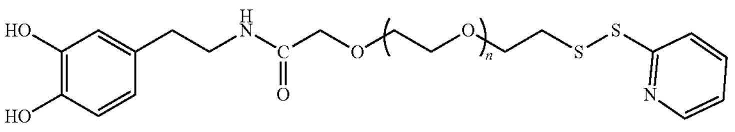 |
| Iron oxide Nanoparticle (PF-C) | carboxyl-PEG-carboxyl | 2.0 | Carboxyl (—COOH) | 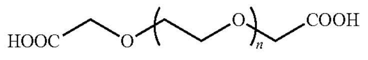 |
| Iron oxide Nanoparticle (PF-N) | Methoxy-PEG-amine | 2.0 | Amine (—$NH_2$) | 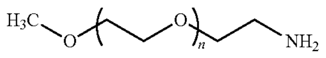 |

TABLE 1-continued

| Exemplary linker molecules | | | | |
|---|---|---|---|---|
| Types of Nanoparticle | PEG linkers | M.W. (kD) | Functional group | Structure |
| Iron oxide Nanoparticle (PF-M) | Methoxy-PEG-maleimide | 2.0 | Maleimide | 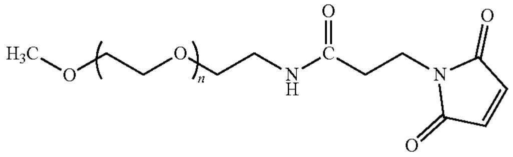 |
| Iron oxide Nanoparticle (PF-O) | Methoxy-PEG-Orthopyridyl disulfide | 2.0 | Orthopyridyl disulfide | 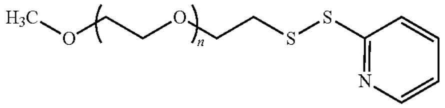 |
| Iron oxide Nanoparticle (PF) | PEG | 2.0 | Hydroxyl (—OH) | 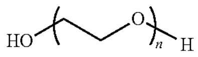 |

In order to couple the substrate or particles of the ubiquitous autoantigen-MHC to the nanoparticle, the following techniques can be applied.

The binding can be generated by chemically modifying the substrate or particle which typically involves the generation of "functional groups" on the surface, said functional groups being capable of binding to an MHC complex, and/or linking the optionally chemically modified surface of the surface or particle with covalently or non-covalently bound so-called "linking molecules," followed by reacting the MHC or MHC complex with the particles obtained.

The functional groups or the linking molecules bearing them may be selected from amino groups, carbonic acid groups, thiols, thioethers, disulfides, guanidino, hydroxyl groups, amine groups, vicinal diols, aldehydes, alpha-haloacetyl groups, mercury organyles, ester groups, acid halide, acid thioester, acid anhydride, isocyanates, isothiocyanates, sulfonic acid halides, imidoesters, diazoacetates, diazonium salts, 1,2-diketones, phosphoric acids, phosphoric acid esters, sulfonic acids, azolides, imidazoles, indoles, N-maleimides, alpha-beta-unsaturated carbonyl compounds, arylhalogenides or their derivatives.

Non-limiting examples for other linking molecules with higher molecular weights are nucleic acid molecules, polymers, copolymers, polymerizable coupling agents, silica, proteins, and chain-like molecules having a surface with the opposed polarity with respect to the substrate or particle. Nucleic acids can provide a link to affinity molecules containing themselves nucleic acid molecules, though with a complementary sequence with respect to the linking molecule. In some embodiments, the linking molecule comprises polyethylene glycol. In some embodiments, the linking molecule comprises polyethylene glycol and maleimide. In some embodiments, the polyethylene glycol comprises one or more of a C1-$C_3$ alkoxy group, —$R^{10}$NHC(O)R—, —$R^{10}$C(O)NHR—, —$R^{10}$C(O)R—, —$R^{10}$C(O)OR—, wherein each R is independently H or $C_1$-$C_6$ alkyl and wherein each $R_{10}$ is independently a bond or $C_1$-$C_6$ alkyl.

pMHCs can be coupled to nanoparticles by a variety of methods, one non-limiting example includes conjugation to NPs produced with PEG linkers carrying distal —NH2 or —COOH groups that can be achieved via the formation of amide bonds in the presence of 1-Ethyl-3-[3-dimethylaminopropyl]carbodiimide hydrochloride (EDC). NPs with —COOH groups are first dissolved in 20 mM MES buffer, pH 5.5. N-hydroxysulfosuccinimide sodium salt (sulpha-NHS, Thermo Scientific, Waltham, MA, final concentration 10 mM) and EDC (Thermo scientific, Waltham, MA, final concentration 1 mM) is added to the NP solution. After 20 min of stirring at room temperature, the NP solution is added drop-wise to the solution containing pMHC monomers dissolved in 20 mM borate buffer (pH 8.2). The mixture is stirred for an additional 4 hr. To conjugate MHCs to NH2-functionalized NPs pMHCs are first dissolved in 20 mM MES buffer, pH 5.5, containing 100 mM NaCl. Sulpha-NHS (10 mM) and EDC (5 mM) are then added to the MHC solution. The activated MHC molecules are then added to the NP solution in 20 mM borate buffer (pH 8.2), and stirred for 4 hr at room temperature.

To conjugate MHC to maleimide-functionalized NPs, pMHCs are first incubated with Tributylphospine (TBP, 1 mM) for 4 hr at room temperature, pMHCs engineered to encode a free carboxyterminal Cys residue are then mixed with NPs in 40 mM phosphate buffer, pH 6.0, containing 2 mM EDTA, 150 mM NaCl, and incubated overnight at room temperature. MHCs of the pMHCs are covalently bound with NPs via the formation of a carbon-sulfur bond between maleimide groups and the Cys residue.

Click chemistry can be used to conjugate ncMHC or avidin to NPs functionalized with azide groups. For this reaction, MHC or avidin molecules are first incubated with a suitable reagent comprising dibenzocyclooctyl (DBCO) functionality, for example: DBCO-NHS (Click Chemistry Tools, Scottdale, AZ) reagent for 2 hr at room temperature. Free DBCO-comprising molecules can be removed by dialysis overnight. MHC- or avidin-DBCO conjugates are then incubated with SFP-Z for 2 hr, resulting in formation of triazole bonds between ncMHCs or avidin molecules and NPs.

Unconjugated pMHCs in the different MHC-NP conjugating reactions can be removed by extensive dialysis using methods known in the art. A non-limiting example is dialysis against PBS, pH 7.4, at 4° C. though 300 kD molecular weight cut off membranes (Spectrum labs). Alternatively, pMHC-conjugated IONPs can be purified by magnetic separation. The conjugated NPs can be concentrated by ultrafiltration through Amicon Ultra-15 units (100 kD MWCO) and stored in PBS.

The surface of the particle can be chemically modified, for instance by the binding of phosphonic acid derivatives having functional reactive groups. One example of these phosphonic acid or phosphonic acid ester derivates is imino-bis(methylenephosphono) carbonic acid which can be synthesized according to the "Mannich-Moedritzer" reaction. This binding reaction can be performed with a substrate or a particle as directly obtained from the preparation process or after a pre-treatment (for instance with trimethylsilyl bromide). In the first case the phosphoric acid (ester) derivative may for instance displace components of the reaction medium which are still bound to the surface. This displacement can be enhanced at higher temperatures. Trimethylsilyl bromide, on the other hand, is believed to dealkylate alkyl group-containing phosphorous-based complexing agents, thereby creating new binding sites for the phosphonic acid (ester) derivative. The phosphonic acid (ester) derivative, or linking molecules bound thereto, may display the same functional groups as given above. A further example of the surface treatment of the substrate or particle involves heating in a diol such as ethylene glycol. It should be noted that this treatment may be redundant if the synthesis already proceeded in a diol.

Under these circumstances the synthesis product directly obtained is likely to show the necessary functional groups. This treatment is, however, applicable to a substrate or a particle that was produced in N- or P-containing complexing agents. If such substrate or particle is subjected to an after-treatment with ethylene glycol, ingredients of the reaction medium (e.g. complexing agent) still binding to the surface can be replaced by the diol and/or can be dealkylated.

It is also possible to replace N-containing complexing agents still bound to the particle surface by primary amine derivatives having a second functional group. The surface of the substrate or particle can also be coated with silica. Silica allows a relatively simple chemical conjugation of organic molecules since silica easily reacts with organic linkers, such as triethoxysilane or chlorosilane. The particle surface may also be coated by homo- or copolymers. Examples for polymerizable coupling agents are: N-(3-aminopropyl)-3-mercaptobenzamidine, 3-(trimethoxysilyl)propylhydrazide and 3-trimethoxysilyl)propylmaleimide. Other non-limiting examples of polymerizable coupling agents are mentioned herein. These coupling agents can be used singly or in combination depending on the type of copolymer to be generated as a coating.

Another surface modification technique that can be used with substrates or particles containing oxidic transition metal compounds is conversion of the oxidic transition metal compounds by chlorine gas or organic chlorination agents to the corresponding oxychlorides. These oxychlorides are capable of reacting with nucleophiles, such as hydroxyl or amino groups as often found in biomolecules. This technique allows generating a direct conjugation with proteins, for instance, via the amino group of lysine side chains. The conjugation with proteins after surface modification with oxychlorides can also be effected by using a bi-functional linker, such as maleimidopropionic acid hydrazide.

For non-covalent linking techniques, chain-type molecules having a polarity or charge opposite to that of the substrate or particle surface are particularly suitable. Examples for linking molecules which can be non-covalently linked to core/shell nanoparticles involve anionic, cationic or zwitter-ionic surfactants, acid or basic proteins, polyamines, polyamides, polysulfone or polycarboxylic acid. The hydrophobic interaction between substrate or particle and amphiphilic reagent having a functional reactive group can generate the necessary link. In particular, chain-type molecules with amphiphilic character, such as phospholipids or derivatised polysaccharides, which can be crosslinked with each other, are useful. The absorption of these molecules on the surface can be achieved by coincubation. The binding between affinity molecule and substrate or particle can also be based on non-covalent, self-organizing bonds. One example thereof involves simple detection probes with biotin as linking molecule and avidin- or streptavidin-coupled molecules.

Protocols for coupling reactions of functional groups to biological molecules can be found in the literature, for instance in "Bioconjugate Techniques" (Greg T. Hermanson, Academic Press 1996). The biological molecule (e.g., MHC molecule or derivative thereof) can be coupled to the linking molecule, covalently or non-covalently, in line with standard procedures of organic chemistry such as oxidation, halogenation, alkylation, acylation, addition, substitution or amidation. These methods for coupling the covalently or non-covalently bound linking molecule can be applied prior to the coupling of the linking molecule to the substrate or particle or thereafter. Further, it is possible, by means of incubation, to effect a direct binding of molecules to correspondingly pre-treated substrate or particles (for instance by trimethylsilyl bromide), which display a modified surface due to this pre-treatment (for instance a higher charge or polar surface).

Synthesis of Nanoparticles

Nanoparticles may be formed by contacting an aqueous phase containing the pMHC complex and a polymer and a non-aqueous phase followed by evaporation of the non-aqueous phase to cause the coalescence of particles from the aqueous phase as taught in U.S. Pat. No. 4,589,330 or 4,818,542. Certain polymers for such preparations are natural or synthetic copolymers or polymers which include gelatin agar, starch, arabinogalactan, albumin, collagen, polyglycolic acid, polylactic acid, glycolide-L(−) lactide poly(epsilon-caprolactone), poly(epsilon-caprolactone-CO-lactic acid), poly(epsilon-caprolactone-CO-glycolic acid), poly(P-hydroxy butyric acid), poly(ethylene oxide), polyethylene, poly(alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisocyanatohexane) and poly(methyl methacrylate). Particularly, certain polymers are polyesters, such as polyglycolic acid, polylactic acid, glycolide-L(−) lactide poly(epsilon-caprolactone), poly(epsilon-caprolactone-CO-lactic acid), and poly(epsilon-caprolactone-CO-glycolic acid). Solvents useful for dissolving the polymer include: water, hexafluoroisopropanol, methylenechloride, tetrahydrofuran, hexane, benzene, or hexafluoroacetone sesquihydrate.

The uaMHC described herein can be coupled to a nanoparticle via the layers previously mentioned or if no layer is present a linker molecule. In certain embodiments, such linker molecules comprise, consist essentially of, or consist of polyethylene glycol (PEG), dextran, or mannitol. In certain embodiments, such linker molecules comprise, consist essentially of, or consist of polyethylene glycol (PEG). In certain embodiments, such linker molecules comprise, consist essentially of, or consist of dextran. Such layers and linkers can be functionalized or derivatized with a group that is able to form a covalent bond with the uaMHC. The reaction can be any suitable reaction, including but not limited to, an amine-to-amine, sulfhydryl-to-sulfhydryl, amine-to-sulfhydryl, carboxyl-to-amine, or sulfhydryl-to-carboxyl. In certain embodiments, the uaMHC is coupled to the linker or layer by the reaction of an NHS ester and a primary amine on the uaMHC (e.g., a lysine residue). In certain embodiments, the uaMHC is coupled to the linker or layer by the reaction of an imidoester and a primary amine on the uaMHC (e.g., a lysine residue). In certain embodiments, the uaMHC is coupled to the linker or layer by the reaction of an amide group and a sulfhydryl group (e.g., cysteine residue) on the uaMHC. In certain embodiments, the uaMHC is coupled to the linker or layer by the reaction of a maleimide group and a sulfhydryl group (e.g., cysteine residue) on the uaMHC. In certain embodiments, the uaMHC is coupled to the linker or layer by the reaction of a maleimide group and a primary amine group on uaMHC. In certain embodiments, the uaMHC is coupled to the linker or layer by the reaction of a haloacetyl group and a sulfhydryl group on uaMHC. In certain embodiments, the uaMHC is coupled to the linker or layer by the reaction of a haloacetyl group and a primary amine group on the uaMHC. In certain embodiments, the uaMHC is coupled to the linker or layer by the reaction of a pyridyldithiol and a sulfhydryl group on uaMHC. In certain embodiments, the uaMHC is coupled to the linker or layer by the reaction of a pyridyldithiol and a primary amine group on the uaMHC. In certain embodiments, the uaMHC is coupled to the linker or layer by the reaction of a carbodiimide and a primary amine group on uaMHC. In certain embodiments, the uaMHC is coupled to the linker or layer by a heterobifunctional linker. In certain embodiments, the uaMHC is coupled to the linker or layer by the reaction of a maleimide/hydrazide and a sulfhydryl group on the uaMHC. In certain embodiments, the uaMHC is coupled to the linker or layer by the reaction of a pyridyldithiol/hydrazide and a sulfhydryl group on the uaMHC. In certain embodiments, the crosslinker is a photoreactive crosslinker.

Gold nanoparticles (GNPs) are synthesized using chemical reduction of gold chloride with sodium citrate as described in Perrault, S. D. et al. (2009) Nano Lett 9:1909-1915. Briefly, 2 mL of 1% of HAuCl4 (Sigma Aldrich) is added to 100 mL H2O under vigorous stirring and the solution is heated in an oil bath. Six (for 14 nm GNPs) or two mL (for 40 nm GNPs) of 1% Na Citrate is added to the boiling HAuCl4 solution, which is stirred for an additional 10 min and then is cooled down to room temperature. GNPs are stabilized by the addition of 1 μMol of thiol-PEG linkers (Nanocs, MA) functionalized with —COOH or —NH2 groups as acceptors of MHC. PEGylated GNPs are washed with water to remove free thiol-PEG, concentrated and stored in water for further analysis. NP density is determined via spectrophotometry and calculated according to Beer's law.

The SFP series of iron oxide NPs (SFP IONPs) can be produced by thermal decomposition of iron acetate in organic solvents in the presence of surfactants, then rendered solvent in aqueous buffers by pegylation (Xie, J. et al. (2007) Adv Mater 19:3163; Xie, J. et al. (2006) Pure Appl. Chem. 78:1003-1014; Xu, C. et al. (2007) Polymer International 56:821-826). Briefly, 2 mMol $Fe(acac)_3$ (Sigma Aldrich, Oakville, ON) are dissolved in a mixture of 10 mL benzyl ether and oleylamine and heated to 100° C. for 1 hr followed by 300° C. for 2 hr with reflux under the protection of a nitrogen blanket. Synthesized NPs are precipitated by addition of ethanol and resuspended in hexane. For pegylation of the IONPs, 100 mg of different 3.5 kD DPA-PEG linkers (Jenkem Tech USA) are dissolved in a mixture of $CHCl_3$ and $HCON(CH_3)_2$ (dimethylformamide (DMF)). The NP solution (20 mg Fe) is then added to the DPA-PEG solution and stirred for 4 hr at room temperature. Pegylated SFP NPs are precipitated overnight by addition of hexane and then resuspended in water. Trace amounts of aggregates are removed by high-speed centrifugation (20,000×g, 30 min), and the monodisperse SFP NPs are stored in water for further characterization and pMHC conjugation. The concentration of iron in IONP products is determined by spectrophotometry at A410 in 2N HCL. Based on the molecular structure and diameter of SFP NPs ($Fe_3O_4$; 8+1 nm diameter) (Xie, J. et al. (2007) *Adv Mater* 19:3163; Xie, J. et al. (2006) *Pure Appl. Chem.* 78:1003-1014), SFP solutions containing 1 mg of iron are estimated to contain $5\times10^{14}$ NPs.

The nanoparticles can also be made by thermally decomposing or heating a nanoparticle precursor. In one embodiment, the nanoparticle is a metal or a metal oxide nanoparticle. In one embodiment, the nanoparticle is an iron oxide nanoparticle. In one embodiment, the nanoparticle is a gold nanoparticle. In one embodiment, provided herein are the nanoparticles prepared in accordance with the present technology. In one embodiment, provided herein is a method of making iron oxide nanoparticles comprising a thermal decomposition reaction of iron acetylacetonate. In one embodiment, the iron oxide nanoparticle obtained is water-soluble. In one aspect, the iron oxide nanoparticle is suitable for protein conjugation. In one embodiment, the method comprises a single-step thermal decomposition reaction.

In one aspect, the thermal decomposition occurs in the presence of functionalized PEG molecules. Certain non-limiting examples of functionalized PEG linkers are shown in Table 1.

In one aspect, the thermal decomposition comprises heating iron acetylacetonate. In one embodiment, the thermal decomposition comprises heating iron acetylacetonate in the presence of functionalized PEG molecules. In one embodiment, the thermal decomposition comprises heating iron acetylacetonate in the presence of benzyl ether and functionalized PEG molecules. Without being bound by theory, in one embodiment, functionalized PEG molecules are used as reducing reagents and as surfactants. The method of making nanoparticles provided herein simplifies and improves conventional methods, which use surfactants that are difficult to be displaced, or are not displaced to completion, by PEG molecules to render the particles water-soluble. Conventionally, surfactants can be expensive (e.g., phospholipids) or toxic (e.g., Oleic acid or oleilamine). In another aspect, without being bound by theory, the method of making nanoparticles obviates the need to use conventional surfactants, thereby achieving a high degree of molecular purity and water solubility.

In one embodiment, the thermal decomposition involves iron acetylacetonate and benzyl ether and in the absence of conventional surfactants other than those employed herein.

In one embodiment, the temperature for the thermal decomposition is about 80° C. to about 300° C., or about 80° C. to about 200° C., or about 80° C. to about 150° C., or about 100° C. to about 250° C., or about 100° C. to about 200° C., or about 150° C. to about 250° C., or about 150° C. to about 250° C. In one embodiment, the thermal decomposition occurs at about 1 to about 2 hours of time.

In one embodiment, the method of making the iron oxide nanoparticles comprises a purification step, such as by using Miltenyi Biotec LS magnet column.

In one embodiment, the nanoparticles are stable at about 4° C. in phosphate buffered saline (PBS) without any detectable degradation or aggregation. In one embodiment, the nanoparticles are stable for at least 6 months.

In one aspect, provided herein is a method of making nanoparticle complexes comprising contacting pMHC with iron oxide nanoparticles provided herein. Without being bound by theory, pMHC encodes a cysteine at its carboxy-terminal end, which can react with the maleimide group in functionalized PEG at about pH 6.2 to about pH 6.5 for about 12 to about 14 hours.

In one aspect, the method of making nanoparticle complexes comprises a purification step, such as by using Miltenyi Biotec LS magnet column.

Regulatory Immune Cell Types

The uaMHC-NP complexes of the current disclosure reprogram or differentiate autoreactive T cells into T regulatory or TR1 cells. In certain embodiments, the TR1 cells express IL-10. In certain embodiments, the TR1 cells secrete IL-10. In certain embodiments, the TR1 cells express CD49b. In certain embodiments, the TR1 cells express LAG-3. T-cells that have these phenotypic characteristics are useful to treat inflammatory or autoimmune conditions of individuals. In certain embodiments, the uaMHC-NP complexes are useful in a method to reprogram or differentiate autoreactive T cells into TR1 cells in an individual after administration. This method generates TR1 cells in an antigen specific way.

The ubiquitous autoantigen-MHCs of the current disclosure are useful for generating B regulatory cells. In certain embodiments, the ubiquitous autoantigen-MHCs of the current disclosure are deployed in a method to generate B-cells expressing high levels of CD1d, CD5, and/or the secretion of IL-10. B-regs are also identified by expression of Tim-1. In certain embodiments, the uaMHC-NP complexes are useful in a method to induce B regulatory cells in an individual after administration. This method generates B regulatory cells in an antigen specific way.

Pharmaceutical Compositions and Administration

Provided herein are pharmaceutical compositions of ubiquitous autoantigen-MHC-NPs useful for the treatment and prevention of disease. The compositions comprise, or alternatively consist essentially of, or yet further consist of, a nanoparticle complex as described herein and a carrier.

Compositions of the disclosure may be conventionally administered parenterally, by injection, for example, intravenously, subcutaneously, or intramuscularly. Additional formulations which are suitable for other modes of administration include oral formulations. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%. The preparation of an aqueous composition that contains an antigen-MHC-nanoparticle complex that modifies the subject's immune condition will be known to those of skill in the art in light of the present disclosure. In one embodiment, the ubiquitous autoantigen-MHC-nanoparticle complex is administered systemically. In specific embodiments, the ubiquitous autoantigen-MHC-NP complex or the compositions comprising a plurality of ubiquitous autoantigen-MHC-N complexes can be administered intravenously.

Typically, the ubiquitous autoantigen-MHC-NPs, described herein, are administered in a manner compatible with the dosage formulation, and in such amount as will be therapeutically effective and immune modifying. The quantity to be administered depends on the subject to be treated. Precise amounts of active ingredient required to be administered depend on the judgment of the practitioner. However, suitable dosage ranges are of the order of ten to several hundred nanograms or micrograms of antigen/MHC/nanoparticle complex per administration.

Suitable regimes for initial administration and boosters are also variable, but are typified by an initial administration followed by subsequent administrations.

The manner of application may be varied widely. Any of the conventional methods for administration of a vaccine are applicable. These are believed to include oral application on a solid physiologically acceptable base or in a physiologically acceptable dispersion, parenterally, by injection and the like. The dosage of the antigen/MHC/nanoparticle complex will depend on the route of administration and will vary according to the size and health of the subject. The ubiquitous autoantigen-MHC-NPs can be administered by any suitable route including intravenous, subcutaneous, intradermal, intramuscular, rectally, or intraperitoneally. In certain embodiments, autoantigen-MHC-NPs are administered parenterally. In certain embodiments, autoantigen-MHC-NPs are administered intravenously. In certain embodiments, autoantigen-MHC-NPs are administered subcutaneously.

In many instances, it will be desirable to have multiple administrations of a ubiquitous autoantigen-MHC-NP, about, at least about, or at most about 3, 4, 5, 6, 7, 8, 9, 10 or more administrations. The administrations will normally range from 1, 2, 3, 4, 5, 6, or 7 day to twelve week intervals, more usually from one to two week intervals. Periodic boosters at intervals of every other day, twice a week, weekly, biweekly, monthly, or 0.1, 0.2, 0.3, 0.4, 0.5, 1, 2, 3, 4 or 5 years, usually two years, will be desirable to maintain the condition of the immune system. The course of the administrations may be followed by assays for autoreactive immune responses, cognate TR1 cells, and T cell activity.

In certain aspects, a single dose of the ubiquitous autoantigen-MHC-NP without including the nanoparticle core and any bioabsorbable/biocompatible outer layer comprises about 0.001 mg/kg to about 2.0 mg/kg, or about 0.001 mg/kg to about 1.5 mg/kg, or about 0.001 mg/kg to about 1.4 mg/kg, or about 0.001 mg/kg to about 1.3 mg/kg, or about 0.001 mg/kg to about 1.2 mg/kg, or about 0.001 mg/kg to about 1.1 mg/kg, or about 0.001 mg/kg to about 1.0 mg/kg. In some embodiments, the single dose comprises from about 0.004 mg/kg to about 1.014 mg/kg, or from about 0.02 mg/kg to about 0.811 mg/kg, or from about 0.041 mg/kg to about 0.608 mg/kg, or from about 0.061 mg/kg to about 0.507 mg/kg, or from about 0.081 mg/kg to about 0.405 mg/kg, or from about 0.121 mg/kg to about 0.324 mg/kg, or from about 0.162 mg/kg to about 0.243 mg/kg. In some embodiments, the single dose comprises from about 0.004 mg/kg to about 1.015 mg/kg, or from about 0.004 mg/kg to about 1.0 mg/kg, or from about 0.004 mg/kg to about 0.9 mg/kg, or from about 0.004 mg/kg to about 0.8 mg/kg, or from about 0.004 mg/kg to about 0.7 mg/kg, or from about 0.004 mg/kg to about 0.6 mg/kg, or from about 0.004 mg/kg to about 0.5 mg/kg, or from about 0.004 mg/kg to about 0.4 mg/kg, or from about 0.004 mg/kg to about 0.3 mg/kg, or from about 0.004 mg/kg to about 0.2 mg/kg, or from about 0.004 mg/kg to about 0.1 mg/kg. Herein, mg/kg refers to milligrams of ubiquitous autoantigen-MHC or ubiquitous autoantigen without considering the MHC component, administered per kg of subject body mass.

Hepatic Inflammatory Diseases

The ubiquitous autoantigen-MHCs of the current disclosure are useful for treating a hepatic inflammatory disorder. Hepatic inflammatory disorders include diseases or disorders arising from inflammation in the liver and can be associated with autoantibodies, inflammatory cell infiltrates including T cells, natural killer T cells, macrophages and/or monocyte cells. Liver inflammatory disease can also involve activation of liver resident macrophages (Kupffer Cells). In certain embodiments, ubiquitous autoantigen-MHCs of the current disclosure are useful in a method to treat or ameliorate a hepatic inflammatory disease selected from the group consisting of hepatitis, non-alcoholic fatty liver disease (NAFLD), non-alcoholic steatohepatitis (NASH), cirrhosis, and pyogenic liver abscesses. In certain embodiments, ubiquitous autoantigen-MHCs of the current disclosure are useful in a method to treat pyogenic liver abscesses. In certain embodiments, ubiquitous autoantigen-MHCs of the current disclosure are useful in a method to treat or ameliorate non-alcoholic steatohepatitis (NASH). In certain embodiments, ubiquitous autoantigen-MHCs of the current disclosure are useful in a method to treat or ameliorate non-alcoholic fatty liver disease (NAFLD). In certain embodiments, ubiquitous autoantigen-MHCs of the current disclosure are useful in a method to treat or ameliorate cirrhosis.

Pharmaceutically Acceptable Stabilizers, Excipients, and Diluents

In some embodiments, the uaMHC-NPs are formulated into a pharmaceutical composition. Pharmaceutical compositions are formulated in a conventional manner using one or more pharmaceutically acceptable inactive ingredients that facilitate processing of the active agents into preparations that are used pharmaceutically. Proper formulation is dependent upon the route of administration chosen. A summary of pharmaceutical compositions, described herein, is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Pharmaceutical compositions can also include surfactants, dispersing agents, and/or viscosity modulating agents. These agents include materials that can control the diffusion and homogeneity of a drug through liquid media or a granulation method or blend method. In some embodiments, these agents also facilitate the effectiveness of a coating or eroding matrix.

Exemplary diffusion facilitators/dispersing agents include, e.g., hydrophilic polymers, electrolytes, Tween® 60 or 80, PEG, Tyloxapol, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K 15M, and HPMC K100M), carboxymethylcellulose sodium, ethylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide; and poloxamer 188); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 4000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and any combination thereof. Plasticizers such as cellulose or triethyl cellulose can also be used as dispersing agents. In some cases, the pharmaceutical composition comprises a surfactant at between 0.01% and 0.5% (w/v). In some instances, the pharmaceutical composition comprises a surfactant at 0.01%, 0.05%, 0.1%, 0.2%, 0.4%, or 0.5% (w/v).

In certain embodiments, the uaMHC-NPs described herein are included in a pharmaceutical composition with a solubilizing emulsifying, or dispersing agent. In certain embodiments, the solubilizing agent can allow high-concentration solutions of the uaMHC-NPs that exceed at least about 0.5 mg/mL, 1 mg/mL, 2 mg/mL, 5 mg/mL, 10 mg/mL, 15 mg/mL, or 20 mg/mL. Carbomers in an aqueous pharmaceutical composition serve as emulsifying agents and viscosity modifying agents. In certain embodiments, the pharmaceutically acceptable excipient comprises or consists of a carbomer. In certain embodiments, the carbomer comprises or consists of carbomer 910, carbomer 934, carbomer 934P, carbomer 940, carbomer 941, carbomer 1342, or combinations thereof. Cyclodextrins in an aqueous pharmaceutical composition serve as solubilizing and stabilizing agents. In certain embodiments, the pharmaceutically acceptable excipient comprises or consists of a cyclodextrin. In certain embodiments, the cyclodextrin comprises or consists of alpha cyclodextrin, beta cyclodextrin, gamma cyclodextrin, or combinations thereof. Lecithin in a pharmaceutical composition may serve as a solubilizing agent. In certain embodiments, the solubilizing agent comprises or consists of lecithin. Poloxamers in a pharmaceutical composition serve as emulsifying agents, solubilizing agents, and dispersing agents. In certain embodiments, the pharmaceutically acceptable excipient comprises or consists of a poloxamer. In certain embodiments, the poloxamer comprises or consists of poloxamer 124, poloxamer 188, poloxamer 237, poloxamer 338, poloxamer 407, or combinations thereof. Polyoxyethylene sorbitan fatty acid esters in a pharmaceutical composition serve as emulsifying agents, solubilizing agents, surfactants, and dispersing agents. In certain embodiments, the pharmaceutically acceptable excipient comprises or consists of a polyoxyethylene sorbitan fatty acid ester. In certain embodiments, the polyoxyethylene sorbitan fatty acid ester comprises or consists of polysorbate 20, polysorbate 21, polysorbate 40, polysorbate 60, polysorbate 61, polysorbate 65, polysorbate 80, polysorbate 81, polysorbate 85, polysorbate 120, or combinations thereof. Polyoxyethylene stearates in a pharmaceutical composition serve as emulsifying agents, solubilizing agents, surfactants, and dispersing agents. In certain embodiments, the pharmaceutically acceptable excipient comprises or consists of a polyoxyethylene stearate. In certain embodiments, the polyoxyethylene stearate comprises or consists of polyoxyl 2 stearate, polyoxyl 4 stearate, polyoxyl 6 stearate, polyoxyl 8 stearate, polyoxyl 12 stearate, polyoxyl 20 stearate, polyoxyl 30 stearate, polyoxyl 40 stearate, polyoxyl 50 stearate, polyoxyl 100 stearate, polyoxyl 150 stearate, polyoxyl 4 distearate, polyoxyl 8 distearate, polyoxyl 12 distearate, polyoxyl 32 distearate, polyoxyl 150 distearate, or combinations thereof. Sorbitan esters in a pharmaceutical composition serve as emulsifying agents, solubilizing agents, and non-ionic surfactants, and dispersing agents. In certain embodiments, the pharmaceutically acceptable excipient comprises or consists of a sorbitan ester. In certain embodiments, the sorbitan ester comprises or consists of sorbitan laurate, sorbitan oleate, sorbitan palmitate, sorbitan stearate, sorbitan trioleate, sorbitan sesquioleate, or combinations thereof. In certain embodiments, solubility can be achieved with a protein carrier. In certain embodiments the protein carrier comprises recombinant human albumin.

In certain embodiments, the uaMHC-NP complexes of the current disclosure are included in a pharmaceutical composition comprising one or more pharmaceutically acceptable stabilizers excipients, carriers, and diluents. In certain embodiments, the uaMHC-NP complexes of the current disclosure are administered suspended in a sterile solution. In certain embodiments, the solution comprises 0.9% NaCl. In certain embodiments, the solution further comprises one or more of: buffers, for example, acetate, citrate, histidine, succinate, phosphate, bicarbonate and hydroxymethylaminomethane (Tris); surfactants, for example, polysorbate 80 (Tween 80), polysorbate 20 (Tween 20), and poloxamer 188; polyol/disaccharide/polysaccharides, for example, glucose, dextrose, mannose, mannitol, sorbitol, sucrose, trehalose, and dextran 40; amino acids, for example, glycine or arginine; antioxidants, for example, ascorbic acid, methionine; or chelating agents, for example, EDTA or EGTA. In certain embodiments, the uaMHC-NP complexes of the current disclosure are shipped/stored lyophilized and reconstituted before administration. In certain embodiments, the lyophilized uaMHC-NP complexes formulations comprise a bulking agent such as mannitol, sorbitol, sucrose, trehalose, or dextran 40. The lyophilized formulation can be contained in a vial comprised of glass. The uaMHC-NP complexes, when formulated, whether reconstituted or not, can be buffered at a certain pH, generally less than 7.0. In certain embodiments, the pH can be between 4.5 and 6.5, 4.5 and 6.0, 4.5 and 5.5, 4.5 and 5.0, or 5.0 and 6.0. In certain embodiments, the uaMHC-NP complexes can be formulated for intravenous injection. In certain embodiments, uaMHC-NP complexes can be formulated for oral ingestion. In certain embodiments, uaMHC-NP complexes can be formulated for parenteral administration, intramuscular injection, subcutaneous injection, or other intra tissue injection. In certain embodiments, uaMHC-NP complexes can be formulated and/or administered without any immunological adjuvant or other compound or polypeptide intended to increase or decrease an immune response.

EXAMPLES

The following illustrative examples are representative of embodiments of the compositions and methods described herein and are not meant to be limiting in any way.

Example 1—TR1 Like CD4+ T-Cell Formation and Expansion by PBC-Relevant pMHC Class II-NPs NOD.c3c4 mice, which carry anti-diabetogenic B6-derived chromosome 3 and 4 regions, spontaneously develop a form of autoimmune biliary ductal disease that resembles human PBC. See Irie, J., et al. *J. Exp. Med.* 203, 1209-1219. Like >90% of patients, these mice develop pathogenic T- and B-cell responses against the E2 and E3BP components of the pyruvate dehydrogenase (PDC) complex. See Kita, H. et al. *J. Clin. Invest.* 109, 1231-1240. In NOD.c3c4 mice as well as in humans, these autoimmune responses promote the destruction of biliary epithelial cells, leading to cholestasis, small bile duct proliferation, and finally liver failure.

To design PBC-relevant pMHC class II-based nanomedicines, we searched for 15mer peptides in murine PDC-E2 capable of binding to the NOD/NOD.c3c4 mouse MHC class II molecule (I-$A^{g7}$) in silico. I-$A^{g7}$-based pMHCs encoding two such epitopes (PDC-$E2_{166-181}$ and PDC-$E2_{82-96}$) were chosen for experimentation. The T1D-relevant I-$A^{g7}$-binding BDC2.5 mimotope was used as a negative control. These complexes were produced in lentiviral-transduced Chinese hamster ovary (CHO) cells, purified by sequential nickel and streptag affinity chromatography, and covalently coated via a free carboxyterminal cysteine onto iron-oxide nanoparticles produced by thermal decomposition of Iron(III) acetylacetonate ($Fe(acac)_3$) in the presence of maleimide-functionalized polyethylene glycol, as described in Singha, S. et al. *Nature Nanotechnology* 12, 701-710.

pMHC tetramer staining studies demonstrated that NOD.c3c4 (but not NOD) mice harbor increasing levels of both the PDC-$E2_{166-181}$/$IA^{g7}$ and PDC-$E2_{82-96}$/$IA^{g7}$-reactive T-cell subsets with age as shown in FIG. 1A (upside-down triangles, middle and right panels). In contrast, and unlike NOD mice, NOD.c3c4 mice contain negligible levels of the T1D-relevant BDC2.5 mi/$IA^{g7}$-reactive subset as shown in FIG. 1A (triangles, middle and right panels), an outcome that is consistent with the PBC vs T1D proclivity of these two strains. Thus, progression of liver autoimmunity in NOD.c3c4 mice is accompanied by increases in the size and/or circulating activity of PDC-E2-specific CD4+ T-cells.

Figure 1B:
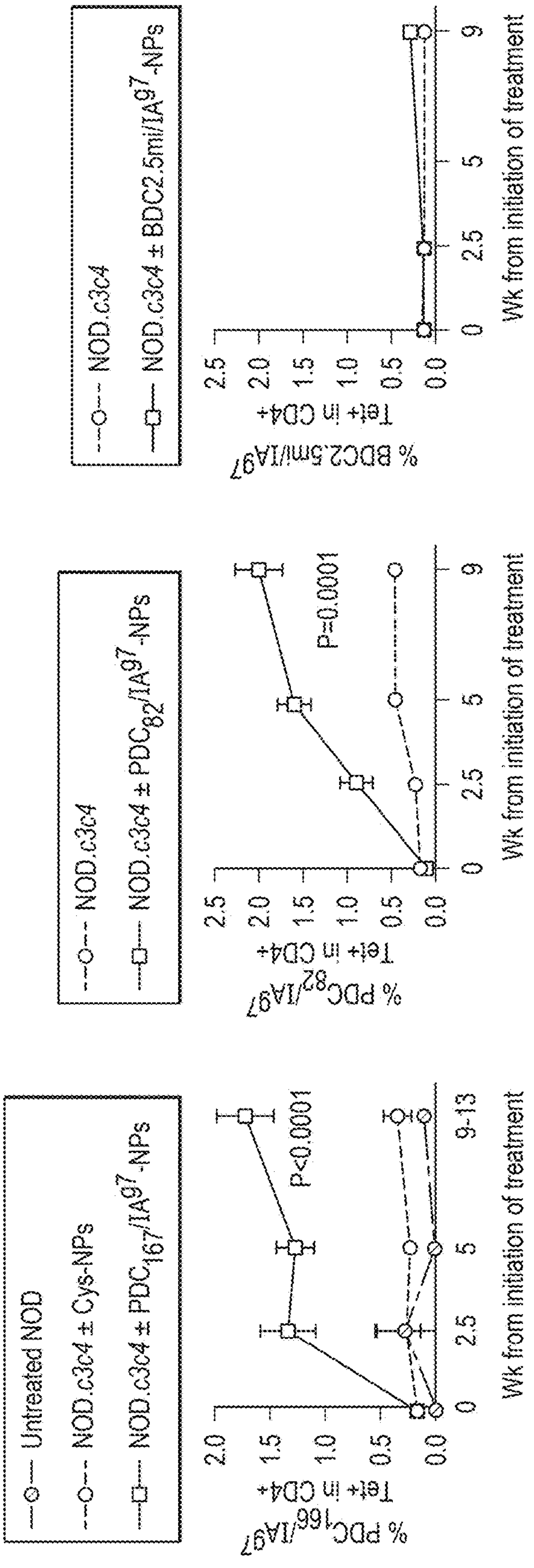
Figure 1C:
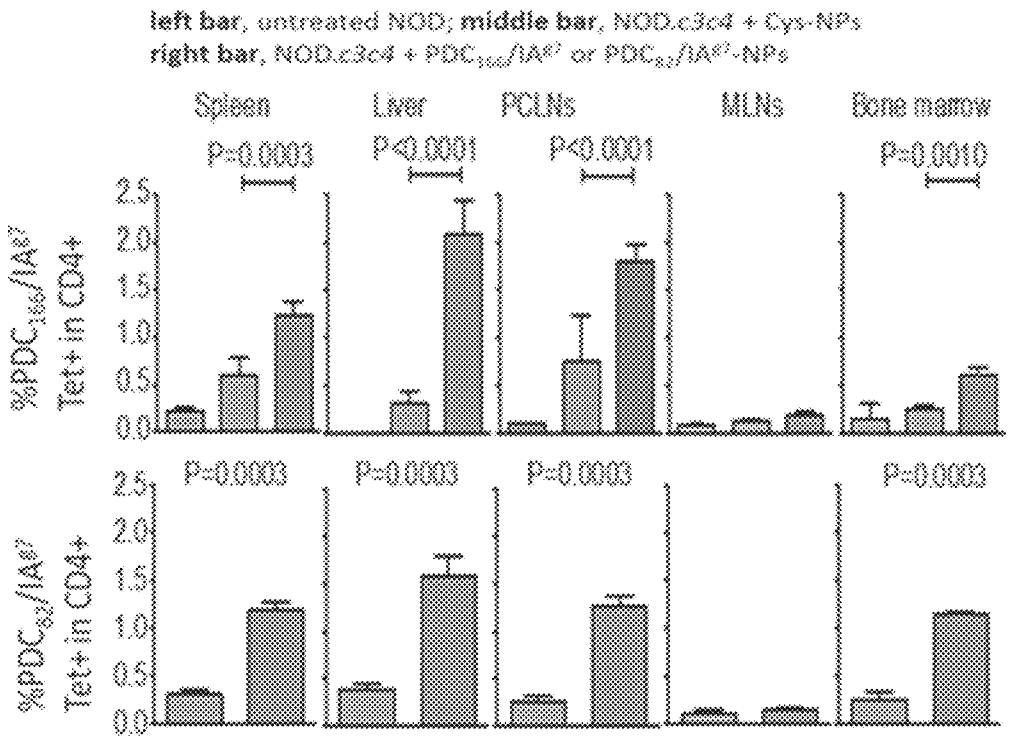

To ascertain if PBC-relevant pMHC class II-NPs could trigger the formation and expansion of PDC-E2-specific TR1-like CD4+ T-cells in NOD.c3c4 mice, we first treated 15 week-old NOD.c3c4 mice (when the disease is well established) with NPs displaying the PDC-$E2_{166-181}$/$IA^{g7}$ pMHC or control NPs (Cys-NPs) (twice a week intravenous for up to 13.5 weeks). Treatment triggered a rapid increase (within 2.5 weeks) in the peripheral frequency of circulating PDC-$E2_{166-181}$/$IA^{g7}$ tetramer+CD4+ T-cells as compared to mice treated with bare NPs or to untreated NOD mice as shown in FIG. 1B (squares, left and middle panels). Studies of mice at the end of follow up confirmed that the PDC-$E2_{166-181}$/$IA^{g7}$-NP-induced expansion of cognate CD4+ T-cells was systemic, with increased frequencies in spleen, bone marrow, liver and liver-draining (portal and celiac lymph nodes), but not non-draining lymph nodes (vs. mesenteric lymph nodes (MLN)) as shown in FIG. 1C.

Figure 1D:
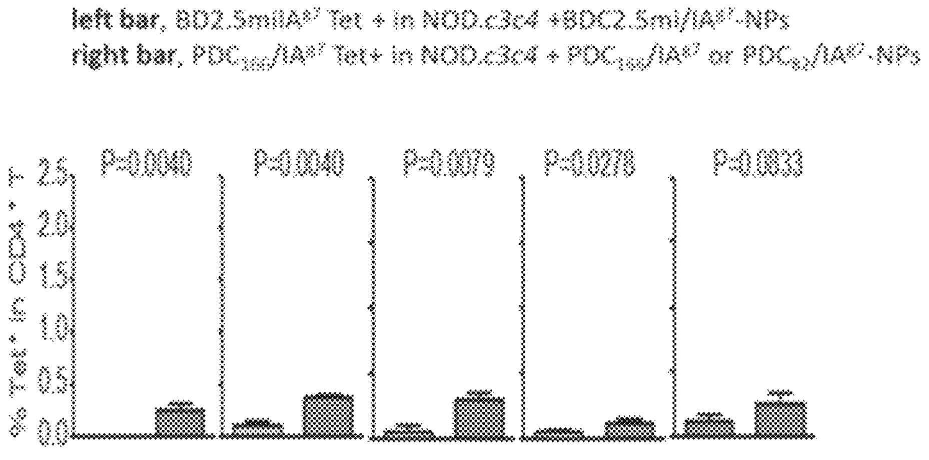

In contrast, treatment of NOD.c3c4 with NPs coated with the T1D-relevant BDC2.5/I-$A^{g7}$ pMHCs did not trigger TR1 cell formation or expansion (FIG. 1B right panel and FIG. 1D). This result is consistent with these nanomedicines exclusively operating on autoantigen-experienced T-cells; NOD.c3c4 mice do not develop islet inflammation and therefore are not expected to harbor antigen-activated BDC2.5 mi/$IA^{g7}$-autoreactive CD4+ T-cells.

Figure 1E:
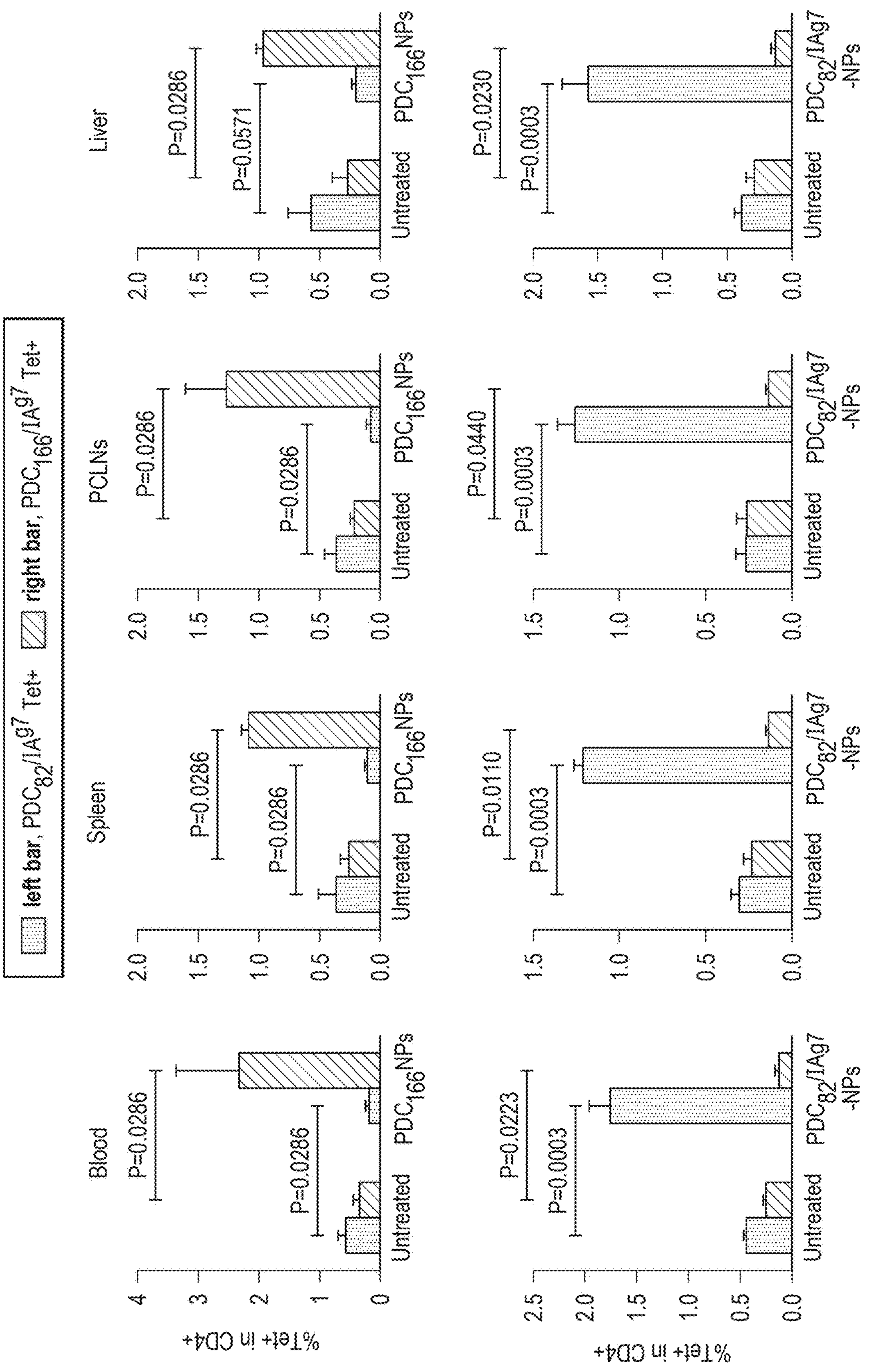

Experiments in additional cohorts of mice demonstrated that the PDC-$E2_{166-181}$/$IA^{g7}$-NP-induced expansion of cognate CD4+ T-cells was peptide-specific, without any detectable expansion of PDC-$E2_{82-96}$/I-$A^{g7}$-reactive CD4+ T-cells (FIG. 1E, top row). In fact, expansion of PDC-$E2_{166-181}$/$IA^{g7}$-specific CD4+ T-cells in these mice was accompanied by significant reductions in the frequency of PDC-E282-96/I-$A^{g7}$-reactive CD4+ T-cells in all organs examined, as compared to the levels detected in age-matched untreated mice (FIG. 1E, top row). This suggests that the PDC-$E2_{166-181}$/$IA^{g7}$-specific CD4+ T-cell subset somehow inhibited the proliferation of its PDC-$E2_{82-96}$/I-$A^{g7}$-reactive counterpart in response to endogenous autoantigen exposure.

Figure 1F:
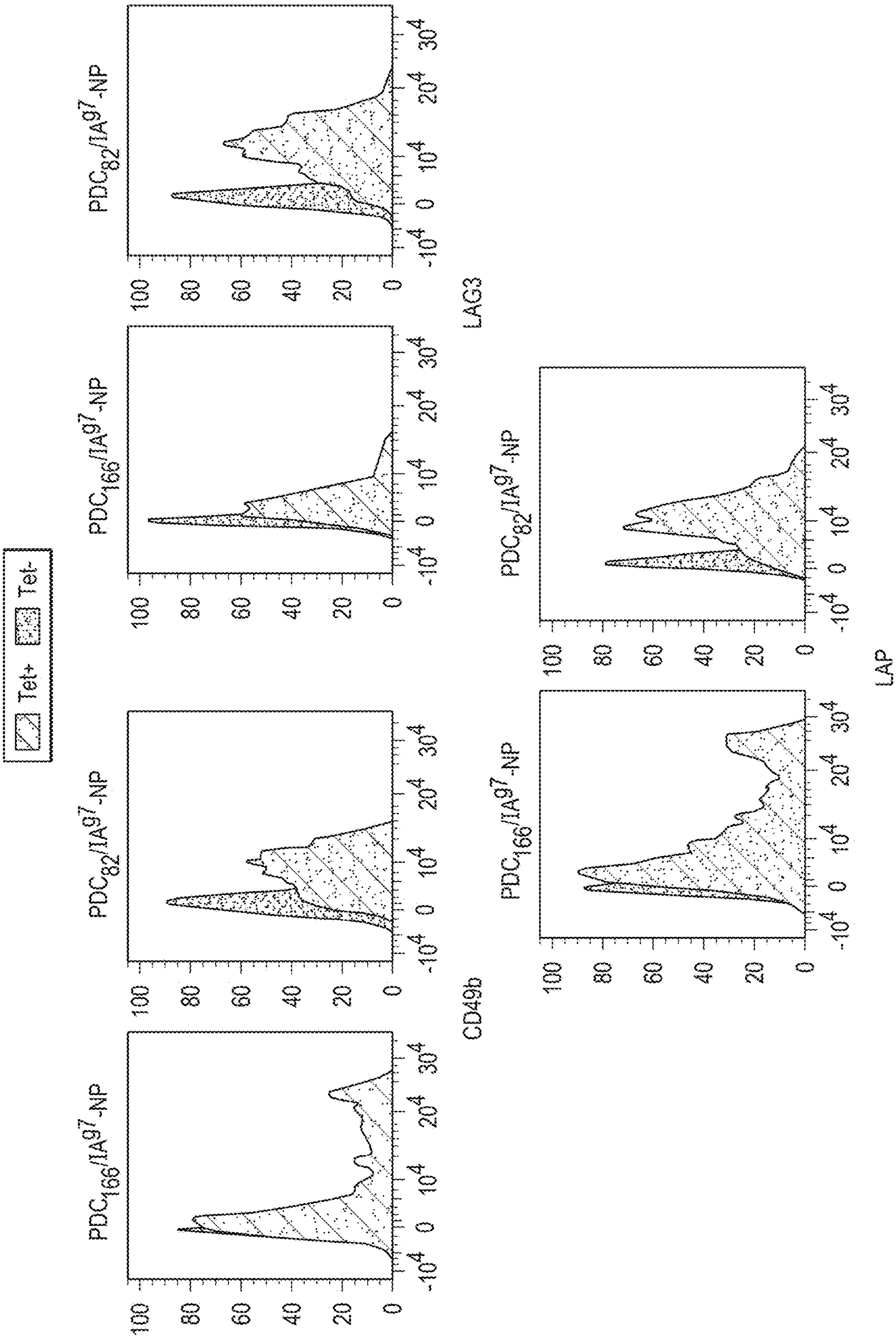
Figure 1G:
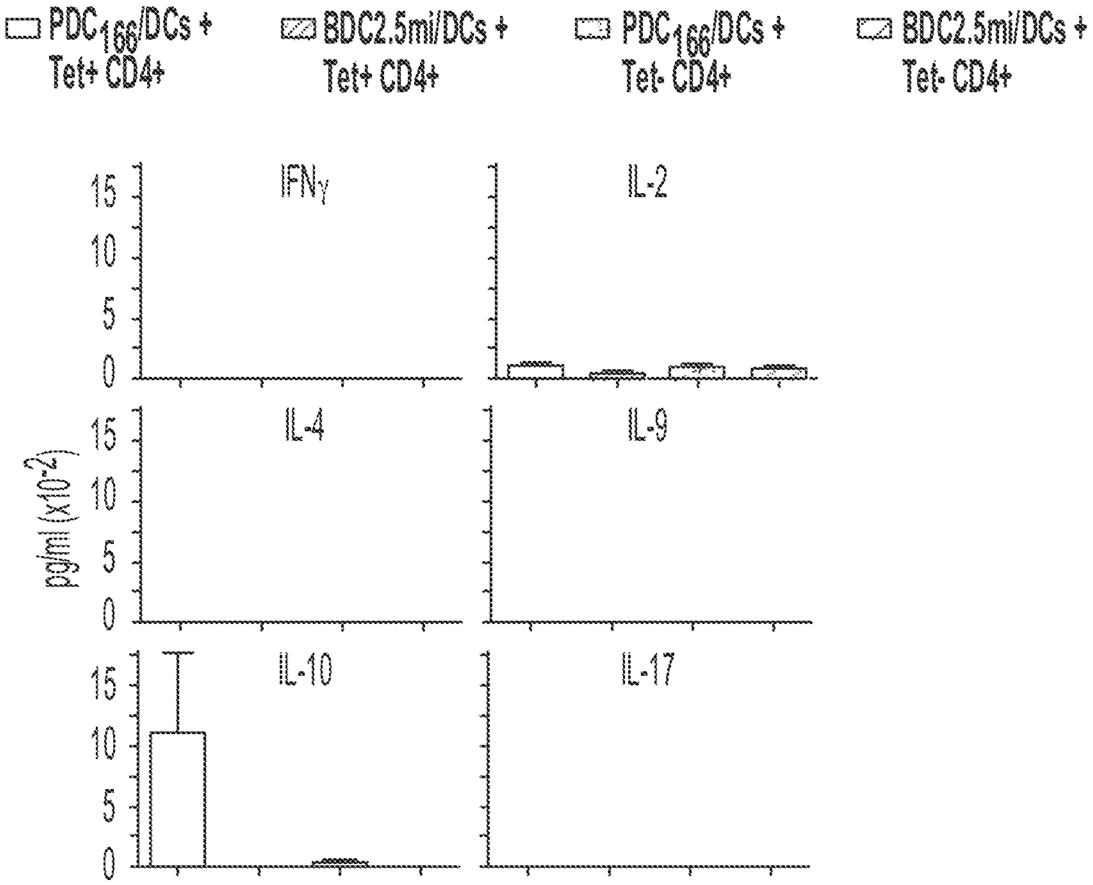
Figure 2A:
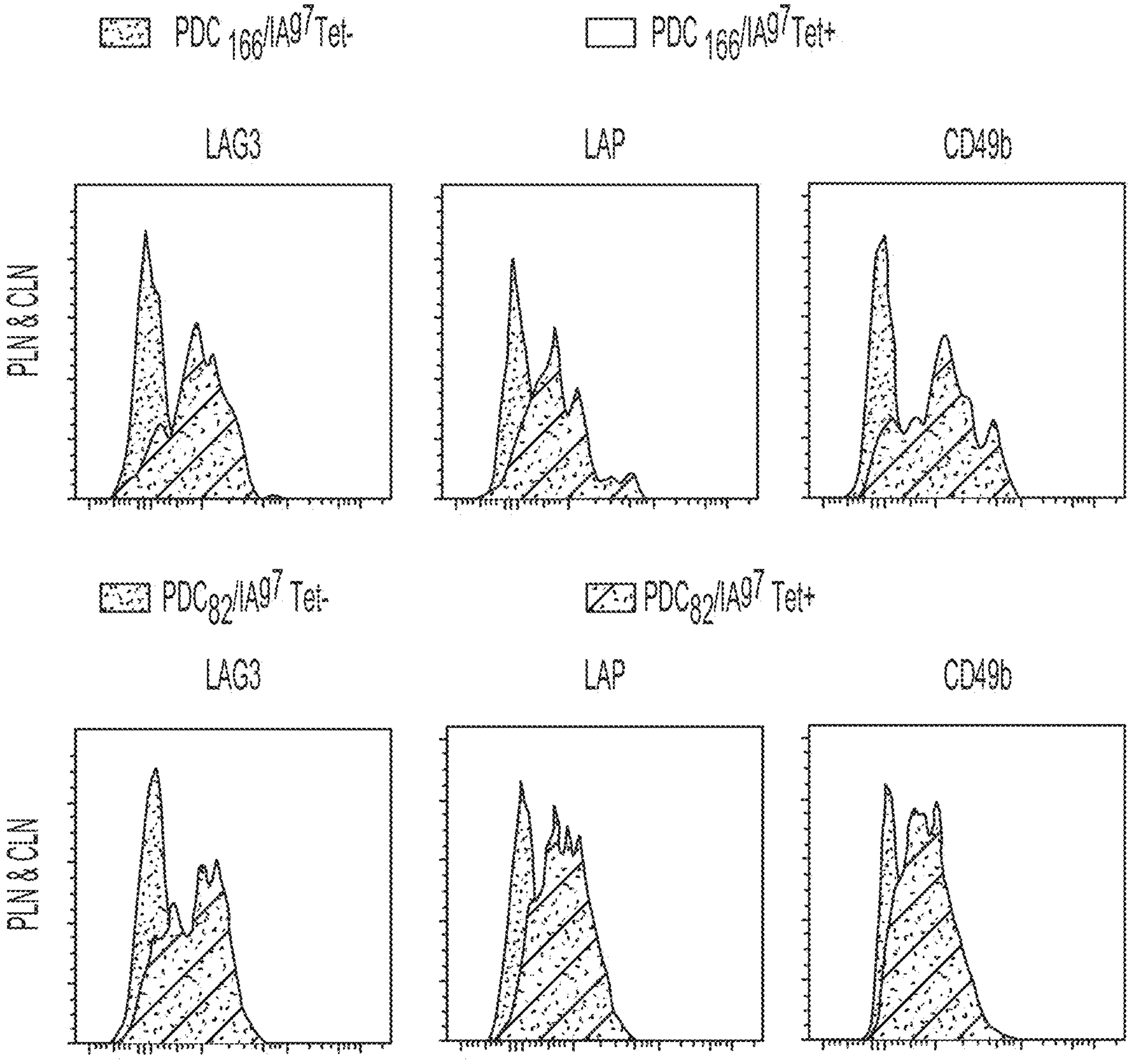
FIGS. 2A-2C illustrate the expansion of PBC relevant regulatory T cells by PBC-relevant pMHC-NPs.
Figure 2B:
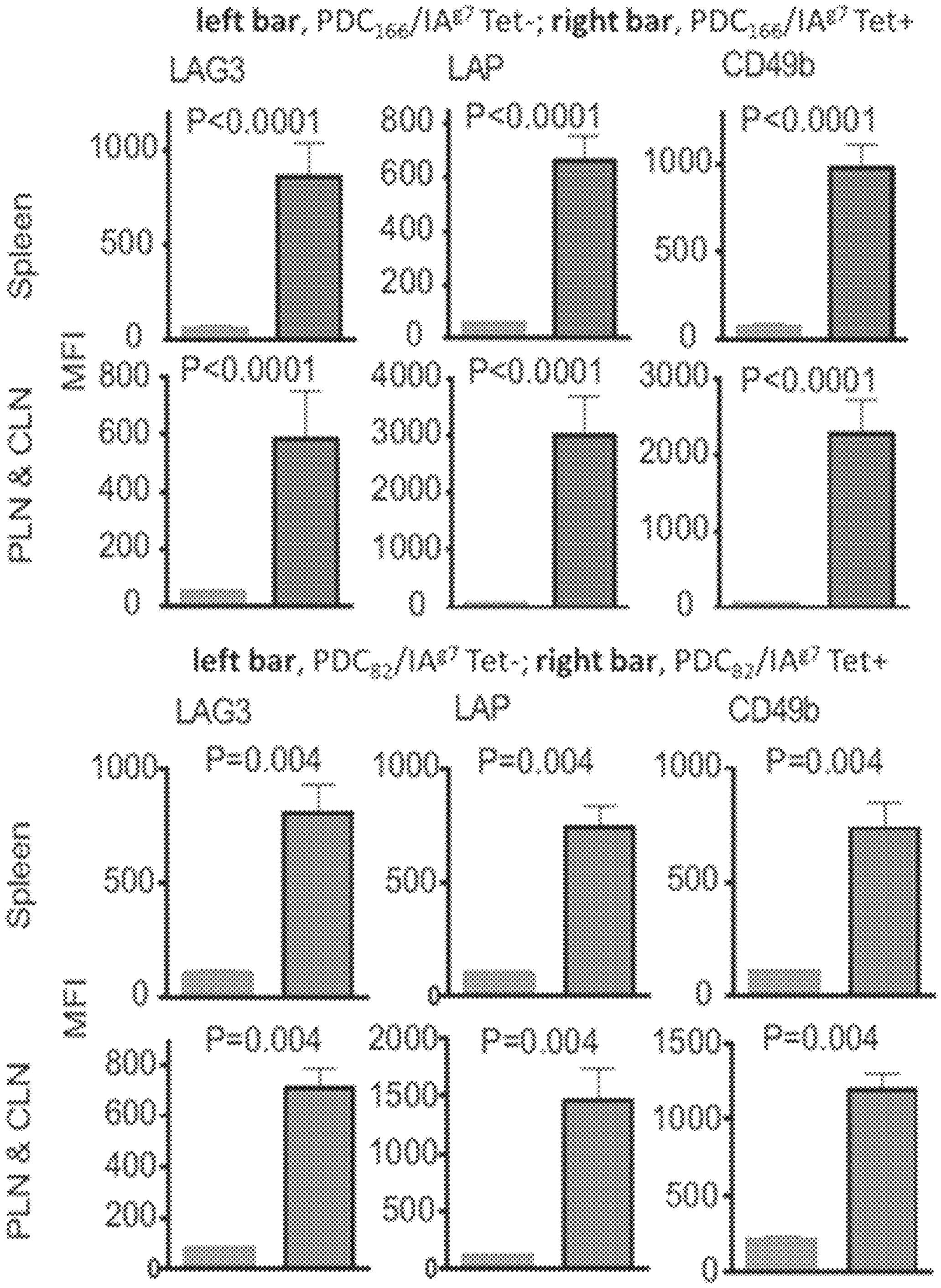

As expected, the PDC-$E2_{166-181}$/$IA^{g7}$ tetramer+CD4+ T-cells that expanded in these mice expressed the TR1 cell markers LAG-3, CD49b and LAP as shown in FIG. 1F and FIGS. 2A and 2B. Furthermore, unlike their tetramer-negative counterparts, the splenic tetramer+CD4+ T-cells of these mice produced the TR1 cytokine IL-10 but not IFNγ, IL-2, IL-4, IL-9 or IL-17 in response to PDC-$E2_{166-181}$ (but not BDC2.5) peptide-pulsed bone marrow-derived DCs (FIG. 1G). Similar results were obtained in mice treated with NPs displaying the second PDC-E2-based pMHC (PDC-$E2_{82-96}$/I-$A^{g7}$), in which there was a significant expansion of cognate PDC-E282-96/I-$A^{g7}$-reactive TR1-like CD4+ T-cells and significant reductions in the frequency of PDC-$E2_{166-181}$/$IA^{g7}$-reactive CD4+ T-cells as shown in FIGS. 1B (center) and 1E (bottom) and FIGS. 2A and 2B, indicating that the above outcome is not a peculiarity of any particular epitope on PDC-E2.

Together, the above data demonstrate that PDC-E2 peptide/$IA^{g7}$-NPs efficiently trigger the formation and expansion of cognate TR1-like CD4+ T-cells in NOD.c3c4 mice, as described previously for T1D-, EAE- and CIA-relevant pMHC class II-NPs in the corresponding disease models.

Example 2—Reversal of Established PBC by Disease-Relevant pMHC Class II-NPs

Figure 3A:
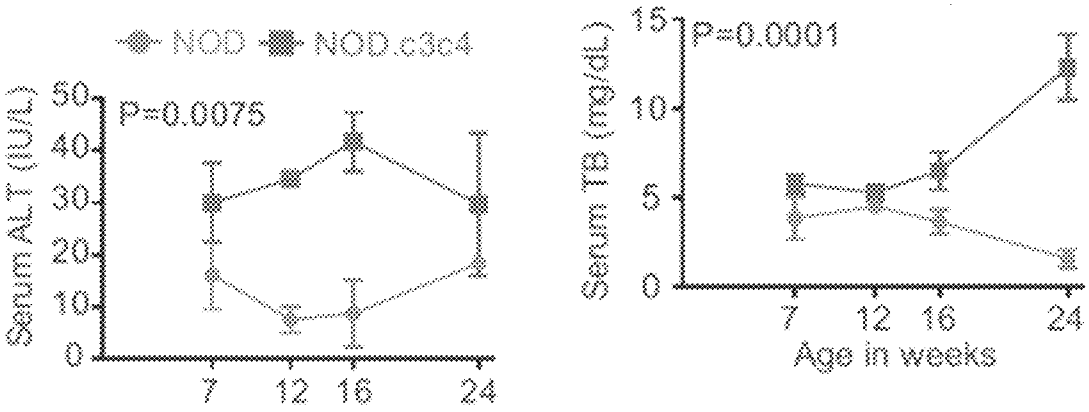
FIGS. 3A-3F illustrate clinical, phenotypic, immunological and pathological features of liver disease in NOD.c3c4 mice.
Figure 3B:
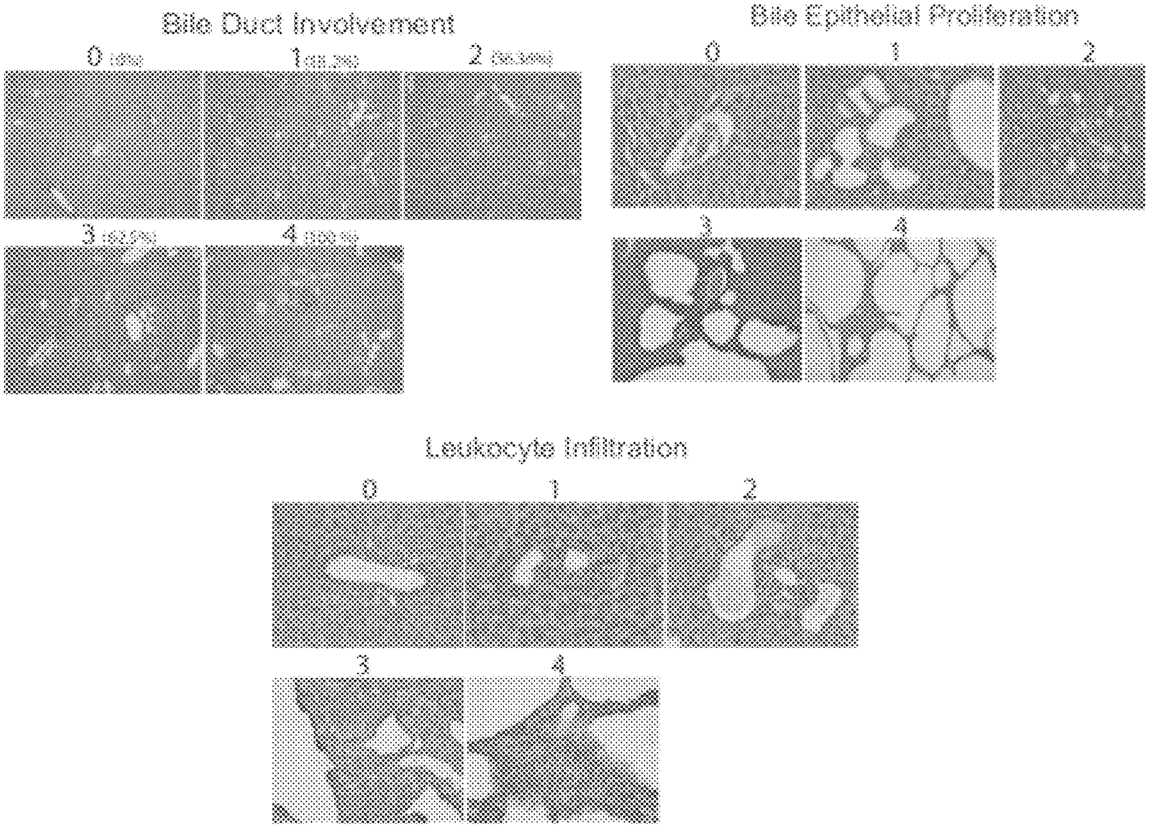
Figure 3C:
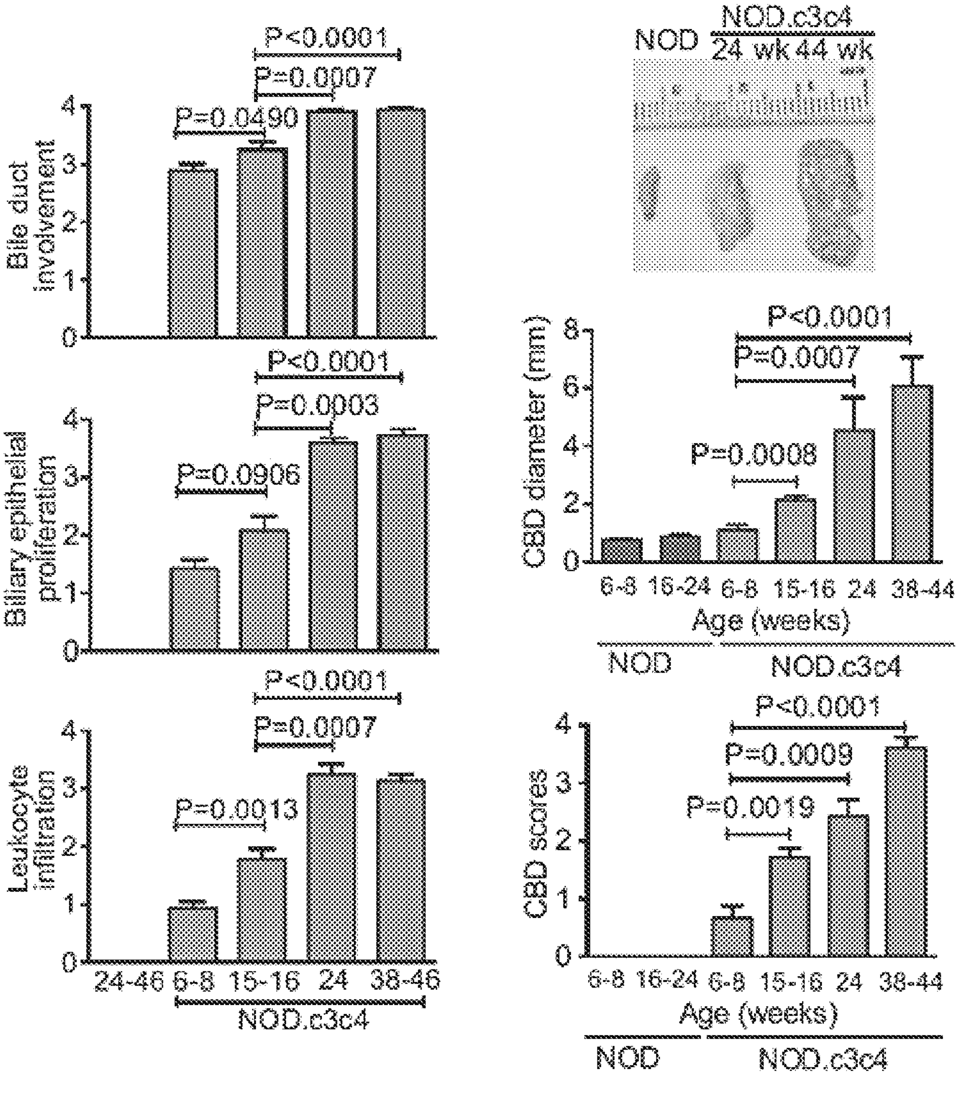
Figure 3D:
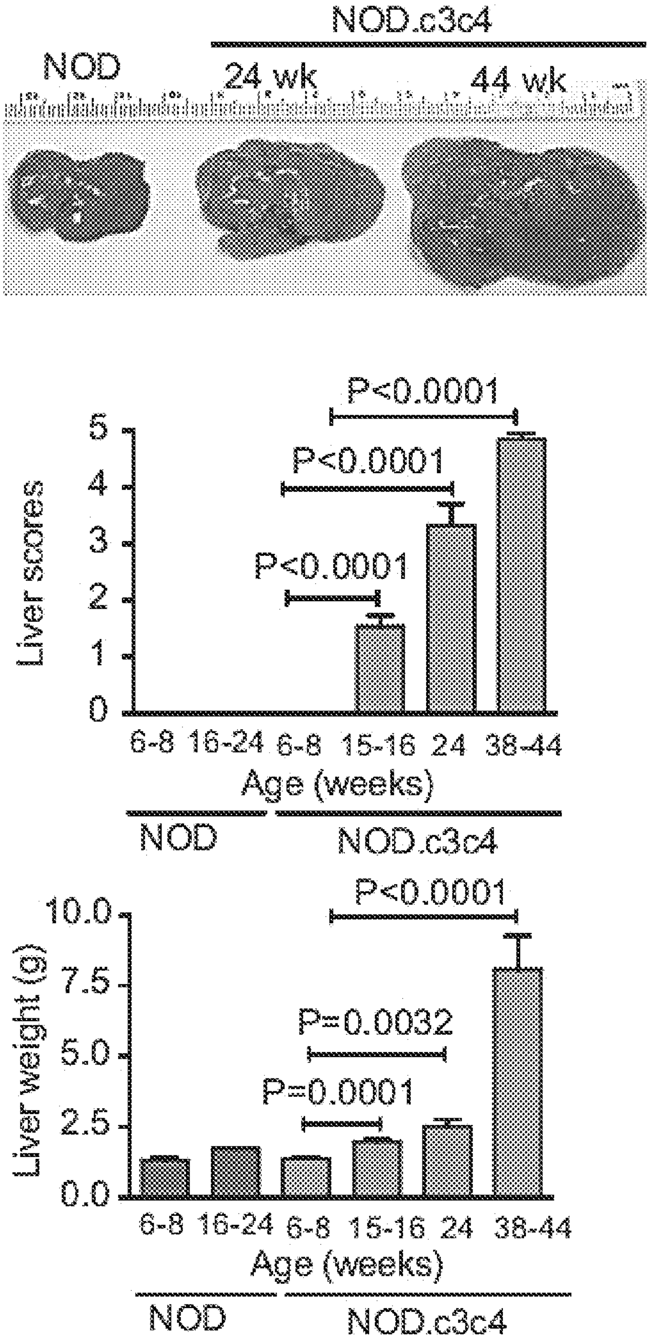
Figure 3E:
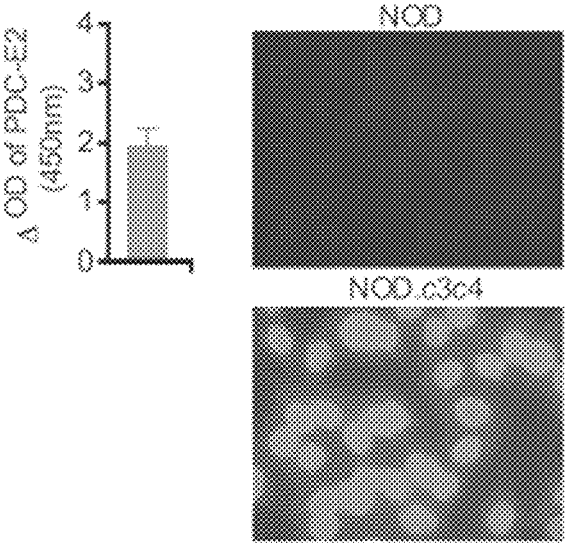
Figure 3F:
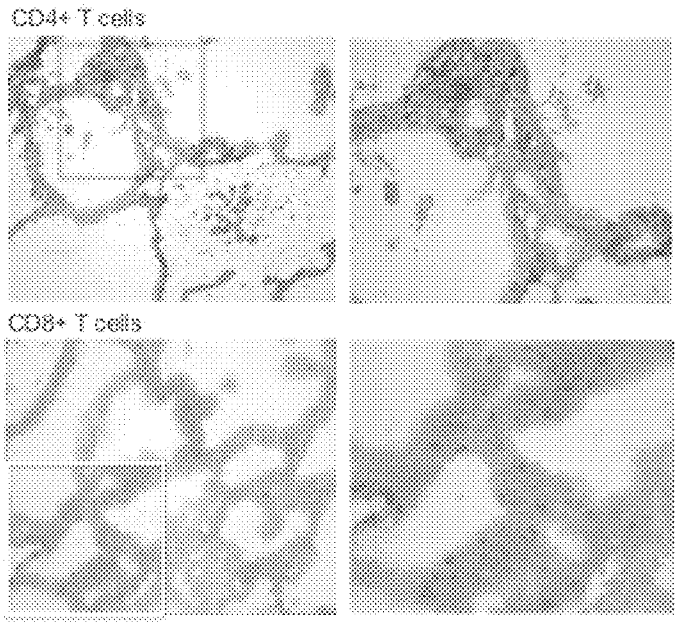

When compared to age-matched NOD mice, 6-8 week-old NOD.c3c4 mice begin to display elevated levels of serum alanine aminotransferase (ALT), microscopic biliary epithelial proliferation, biliary track leukocyte infiltration, massive bile duct involvement (near maximum number of portal triads affected) and macroscopic enlargement of the common biliary duct (CBD) (FIGS. 3A and 3C). FIG. 3B shows an exemplary scoring matrix to quantify microscopic analysis. By ~15-16 weeks these signs worsen and the mice begin to display increased total serum bilirubin (TB) levels (FIG. 3A) high titers of anti-mitochondrial/PDC-E2-specific autoantibodies (absent in NOD mice; FIG. 3E) and macroscopic signs of liver disease (bile cysts) (FIG. 3D). The severity of all these signs of disease peaks at –24 weeks of age (FIGS. 3A-3D), coinciding with massive infiltration of the biliary epithelium by CD4+ and CD8+ T-cells (FIG. 3F), high titers of anti-nuclear autoantibodies (ANAs) (FIG. 3E) and a nearly three-fold increase in liver weight (FIG. 3D).

Figure 4A:
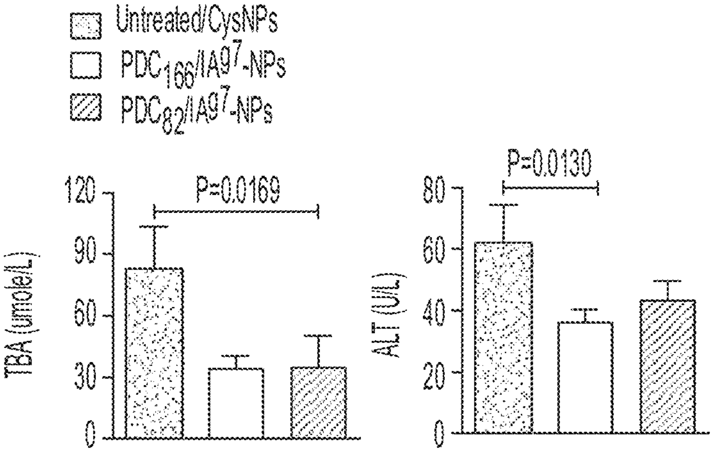
FIGS. 4A-4I illustrate reversal of disease in a mouse model of PBC using PBC-relevant pMHC-NPs.
Figure 4B:
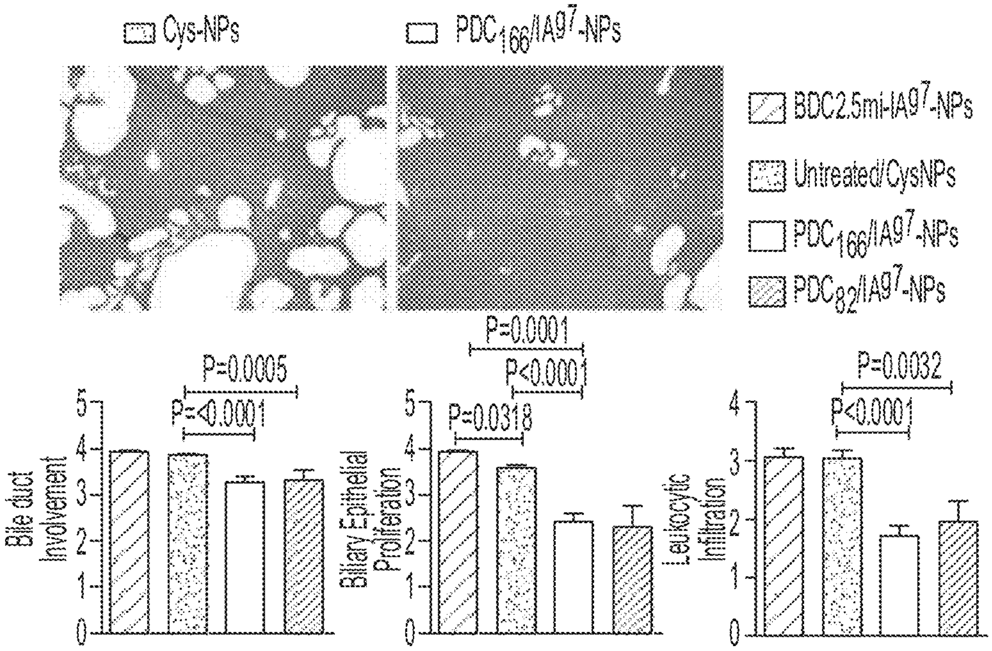
Figure 4C:
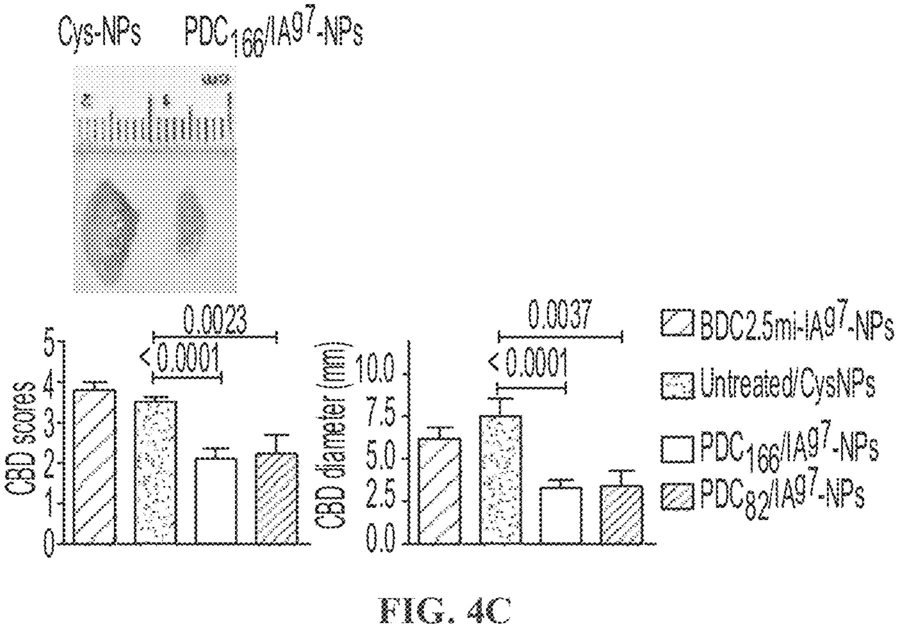
Figure 4D:
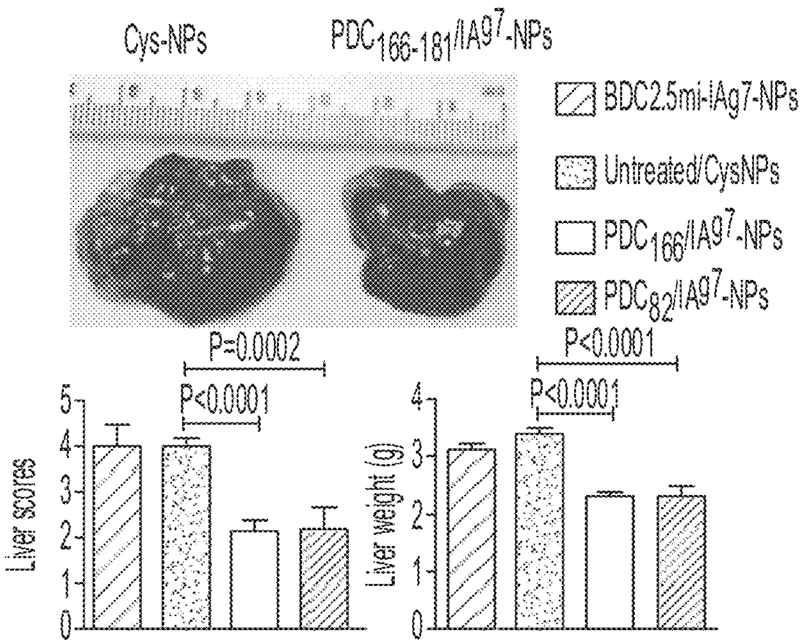
Figure 4E:
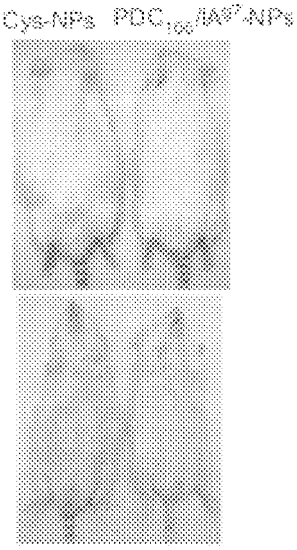
Figure 4F:
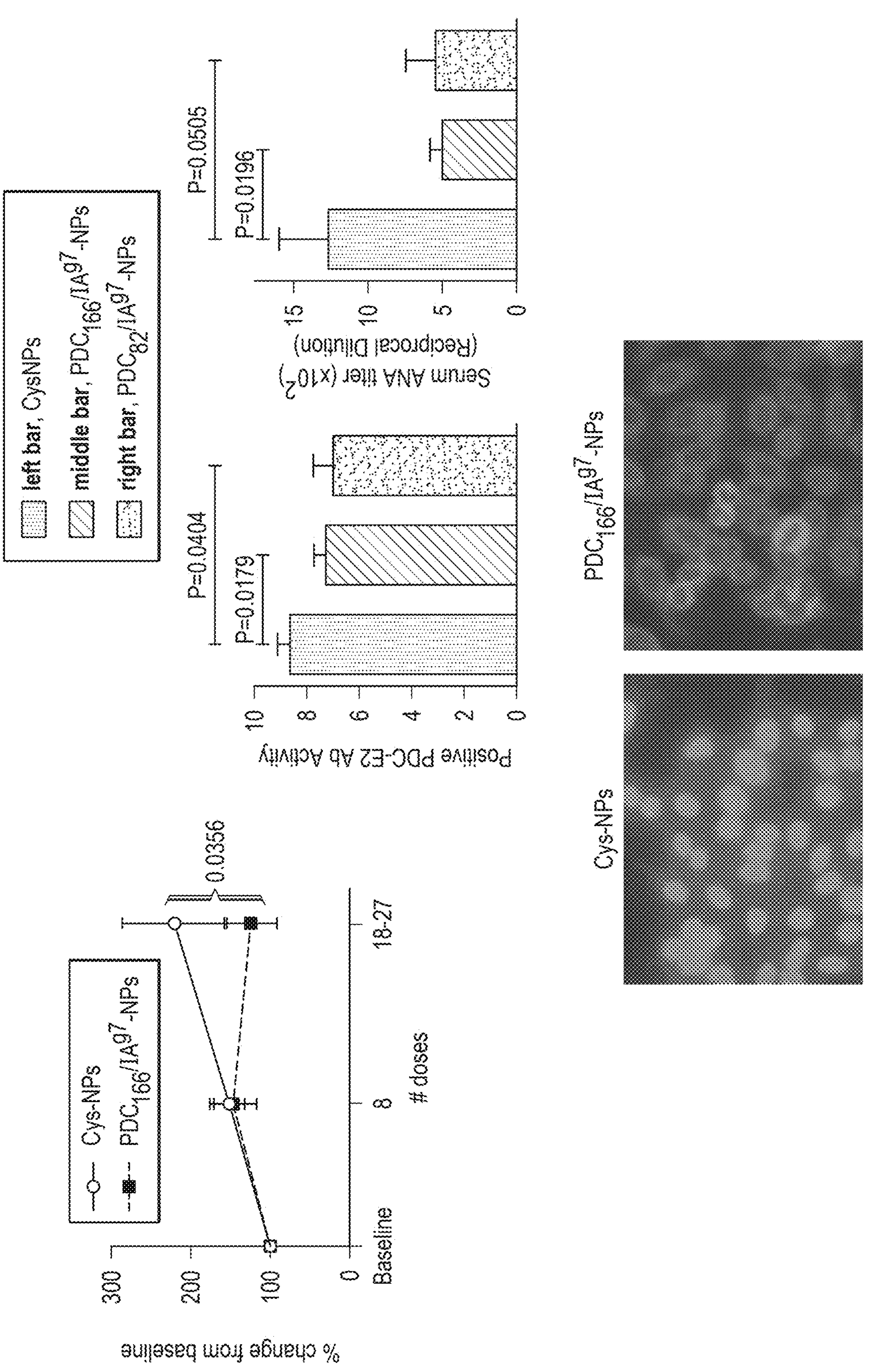

We tested the therapeutic properties of PDC-$E2_{166-181}$/$IA^{g7}$-, PDC-$E2_{82-96}$/I-$A^{g7}$- and BDC2.5/I-$A^{g7}$-NPs in 15 week-old NOD.c3c4 mice, an age when liver autoimmunity in these mice is well established. Mice received biweekly doses of 20 μg of pMHC-NPs or an equivalent dose of control (Cys-conjugated NPs; Cys-NPs) for 9-13.5 weeks. Treatment with PDC-$E2_{166-181}$/$IA^{g7}$-NPs resulted in significant reductions in serum ALT and TB levels (FIG. 4A), bile duct involvement, bile duct epithelial proliferation and leukocyte infiltration (FIG. 4B), common bile duct diameter and macroscopic score (FIG. 4C), liver weight and macroscopic liver scores (FIG. 4D) and abdominal girth (FIG. 4E). Although treatment did not decrease the autoantibody titers found at the initiation of therapy, it clearly blunted the progression of autoantibody formation, as documented by significant reductions in anti-PDC-E2 and anti-nuclear autoantibody titers in mice treated with PDC-$E2_{166-181}$/$IA^{g7}$-NPs, PDC-$E2_{82-96}$/I-$A^{g7}$-NPs vs. control NPs (FIG. 4F). Additional studies with the second PBC-relevant pMHC-NP compound (PDC-$E2_{82-96}$/I-$A^{g7}$-NPs), and the T1D-relevant (but PBC-irrelevant) counterpart (BDC2.5/I-$A^{g7}$-NPs) confirmed the disease specificity of these compounds (FIGS. 4C and 4D).

Figure 2C:
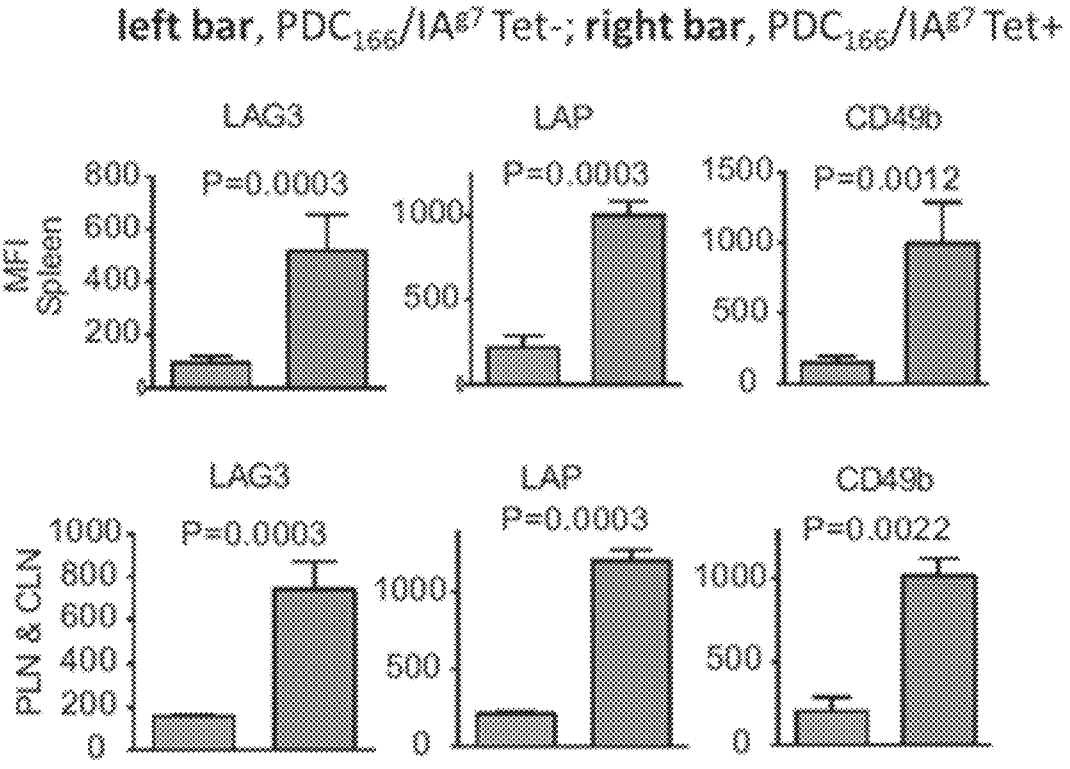
Figure 4G:
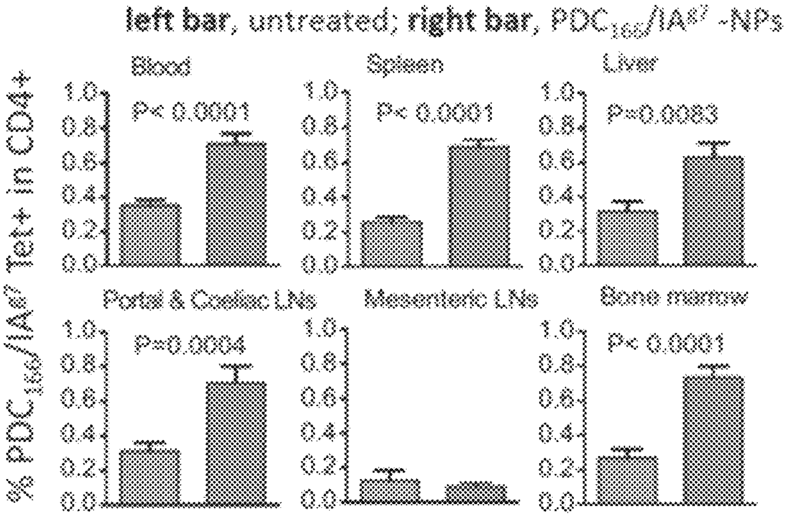
Figure 4H:
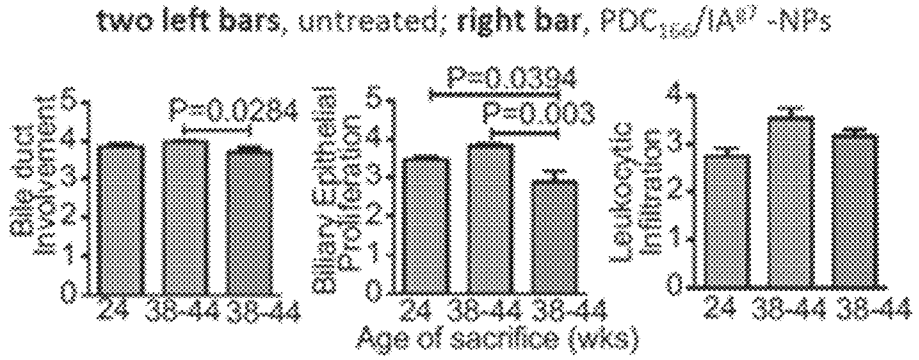
Figure 4I:
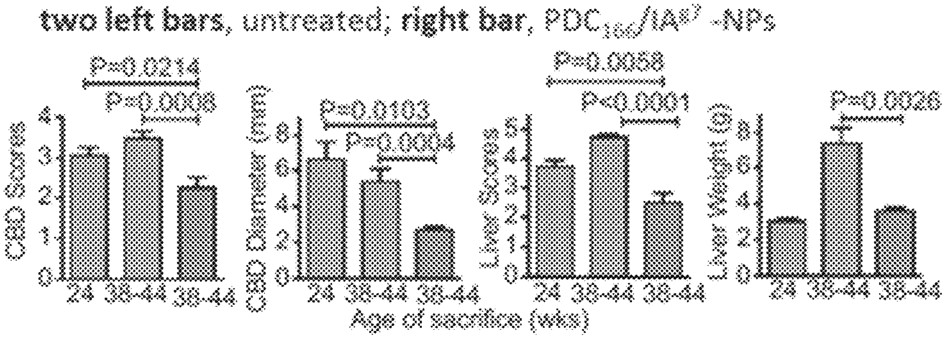

Similar results were obtained when treatment was initiated at the peak of disease severity (24 weeks of age). Analyses of mice after 14-20 weeks of therapy (38-44 weeks of age) with PDC-$E2_{166-181}$/$IA^{g7}$-NPs revealed systemic expansions of TR1-like CD4+ T-cells (FIG. 4G and FIG. 2C) and indicated that the magnitude of the signs of disease (FIGS. 4H and 4I) were significantly lower than those seen at the age when therapy was initiated, suggesting that resolution of liver inflammation by PBC-specific nanomedicines promotes repair of pre-existing liver damage.

Figure 5A:
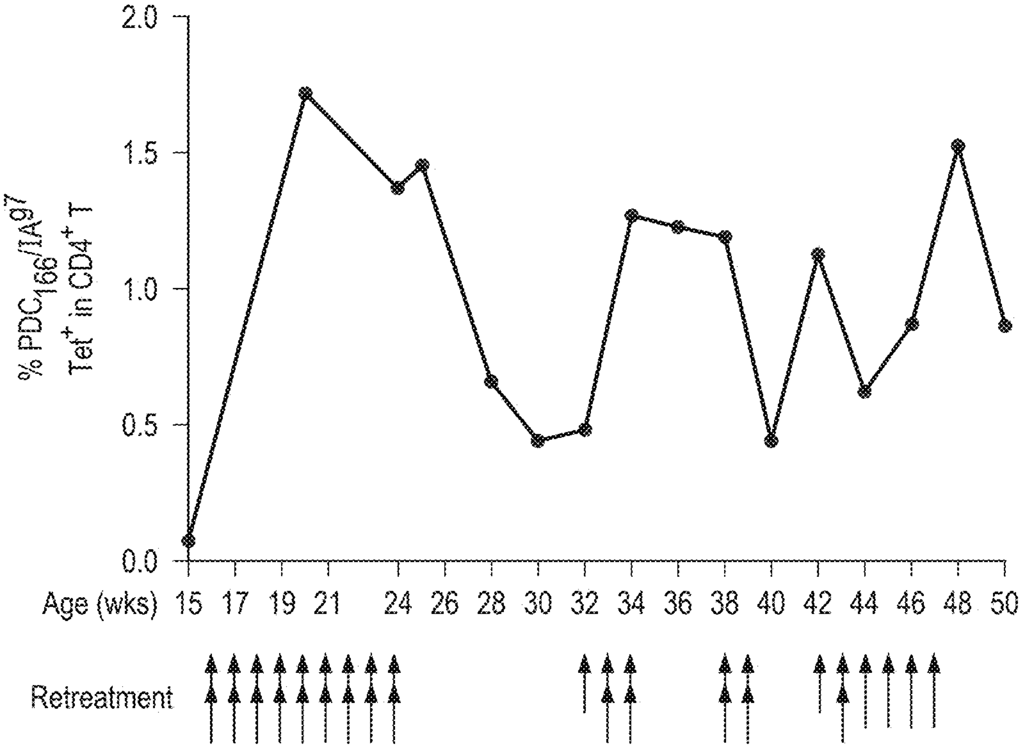
FIGS. 5A-5E illustrate changes in the circulating frequency of tetramer+CD4+ T-cells in response to periodic re-treatment with PBC relevant nanoparticles.
Figure 5A:
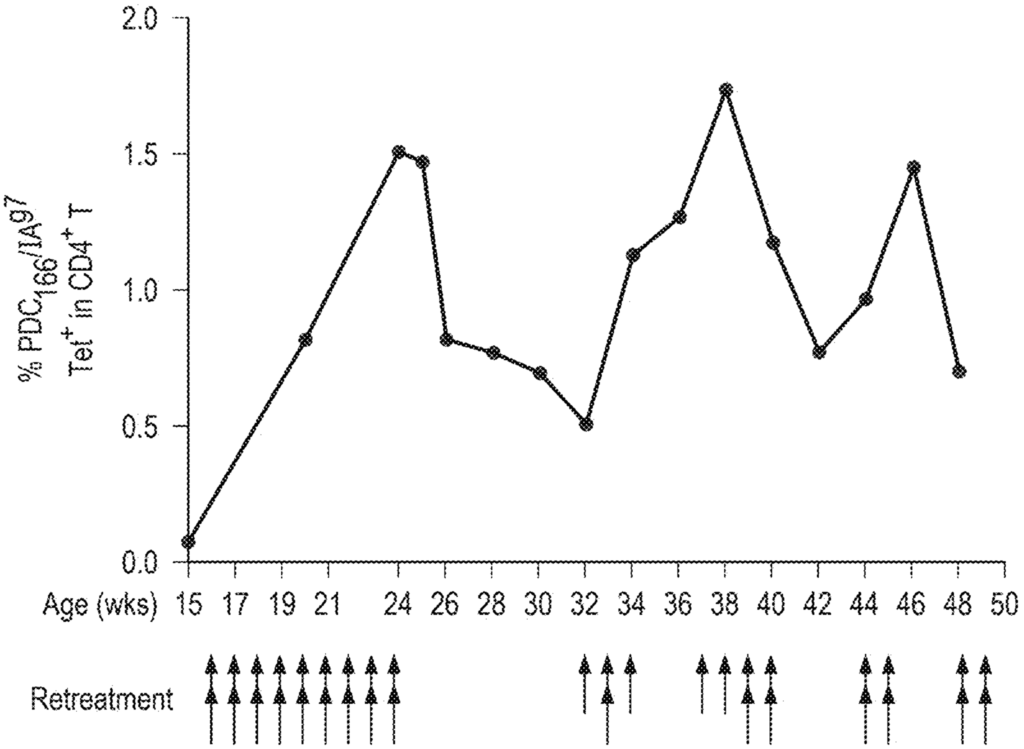
Figure 5B:
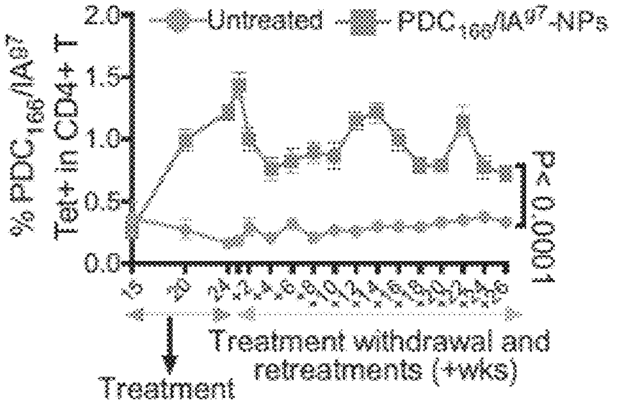
Figure 5C:
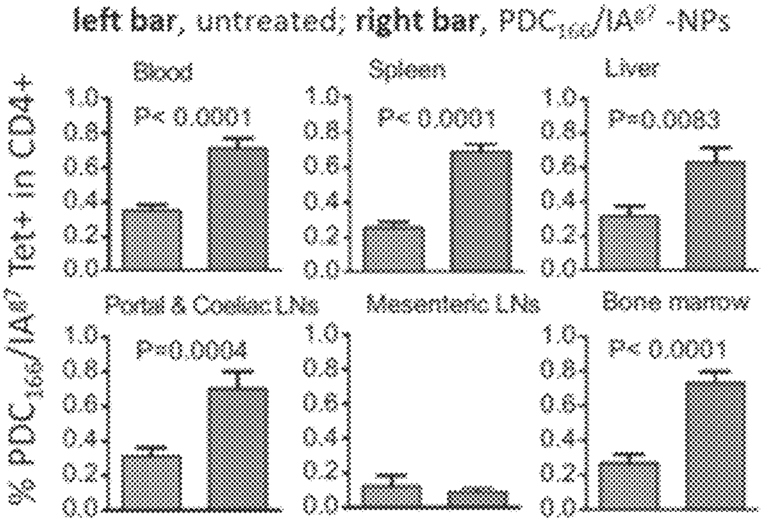
Figure 5D:
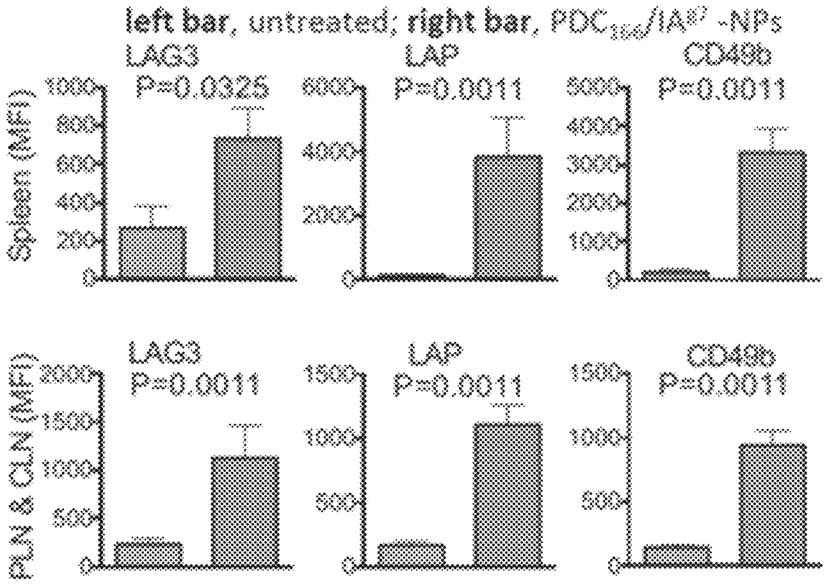
Figure 5E:
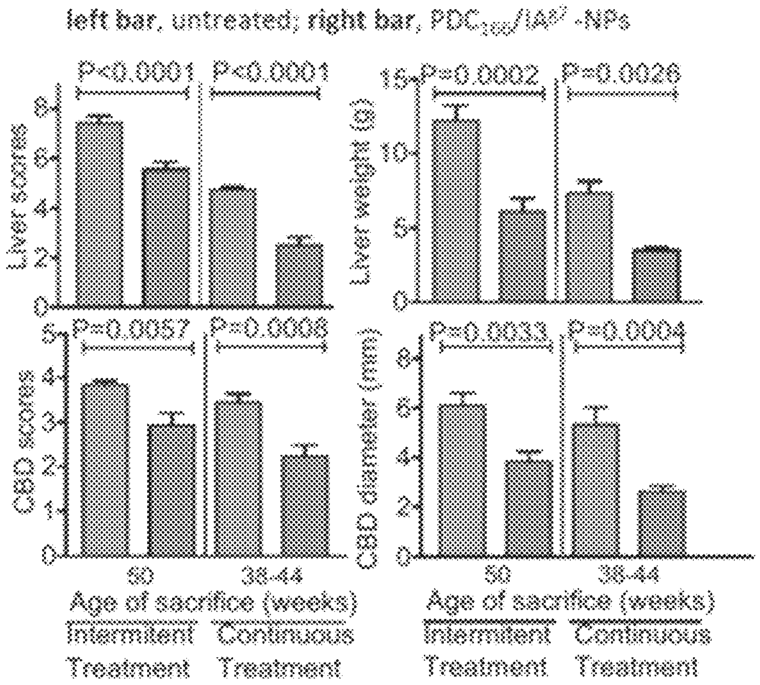

Example 3—Continued Versus Intermittent Treatment pMHC-NP therapy triggers the formation and expansion of cognate TR1 cells systemically, leading to accumulation of these cells in most lymphoid organs as well as at the site of inflammation (See FIGS. 1-3). In addition, these TR1 cells circulate through the bloodstream and their presence in blood can be used as a biomarker to gauge the need for re-treatment. To investigate this, and to ascertain whether circulating levels of cognate TR1-like CD4+ T-cells can in fact be used to guide therapeutic decisions, we withdrew treatment in NOD.c3c4 mice that had been treated with PDC-$E2_{166-181}$/$IA^{g7}$-NPs from 15 week to 24 weeks of age. We then measured the percentage of PDC-$E2_{166-181}$/$IA^{g7}$ tetramer+CD4+ T-cells in peripheral blood every two weeks, and re-treated animals in which the percentage of tetramer+ cells had declined to about 50% of the value at treatment withdrawal; treatment was again withdrawn when the tetramer+ values at the next scheduled measurement had recovered, and repeated this cycle until the mice reached 50 week of age. Although there was considerable variability from mouse to mouse (FIG. 5A), in most animals the peripheral blood tetramer+TR1 cell content progressively declined to about 50% of the original values within 4-6 weeks after treatment withdrawal but re-treatment of these animals rapidly restored these values (FIG. 5B). Intermittent treatment did not compromise the pharmacodynamic (systemic expansion of TR1-like CD4+ T-cells) (FIGS. 5C and 5D) or the therapeutic effects of treatment, including reduced common bile duct diameter/macroscopic scores and liver weight/macroscopic score (FIG. 5E), as compared to values in untreated mice or mice which had been treated continuously from 24 to 38-44 weeks of age.

Example 4—pMHC-NPs Versus the Standard of Care

Ursodeoxycholic acid (UDCA, a hydrophilic bile acid) is the standard of care for PBC. See Charatcharoenwitthaya, P. et al. Long-term survival and impact of ursodeoxycholic acid treatment for recurrent primary biliary cirrhosis after liver transplantation. *Liver Transpl.* 13, 1236-1245. UDCA possesses anti-cholestatic effects and stimulates hepatobiliary secretion, thus protecting cholangiocytes against the toxic effects of hydrophobic bile acids. Although effective in ~50% of patients when given early on in the disease process, it is ineffective at advanced stages of PBC.

Figure 6A:
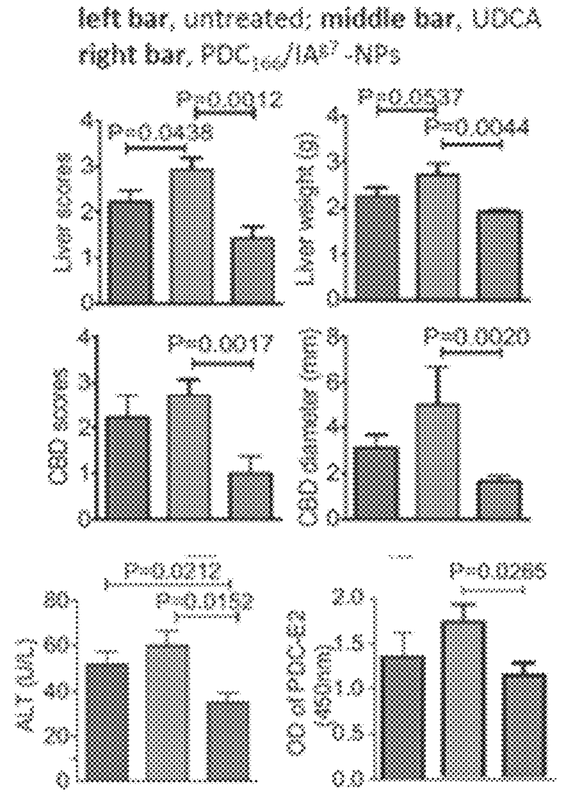
FIGS. 6A-6F illustrate effects of treatment with PBC-relevant pMHC-NPs or the standard of care in PBC (UDCA) on macroscopic and serum ALT levels (FIG. 6A) and microscopic (FIG. 6B) disease scores when treatment is initiated early on in the disease process.
Figure 6B:
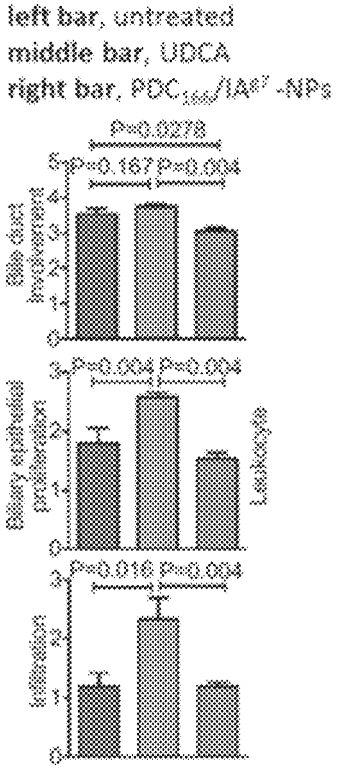
Figure 6C:
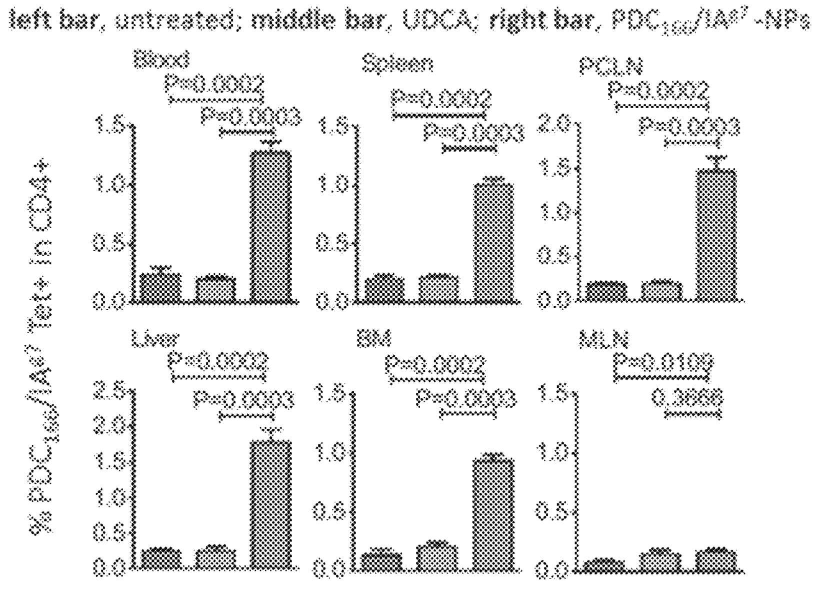
Figure 6D:
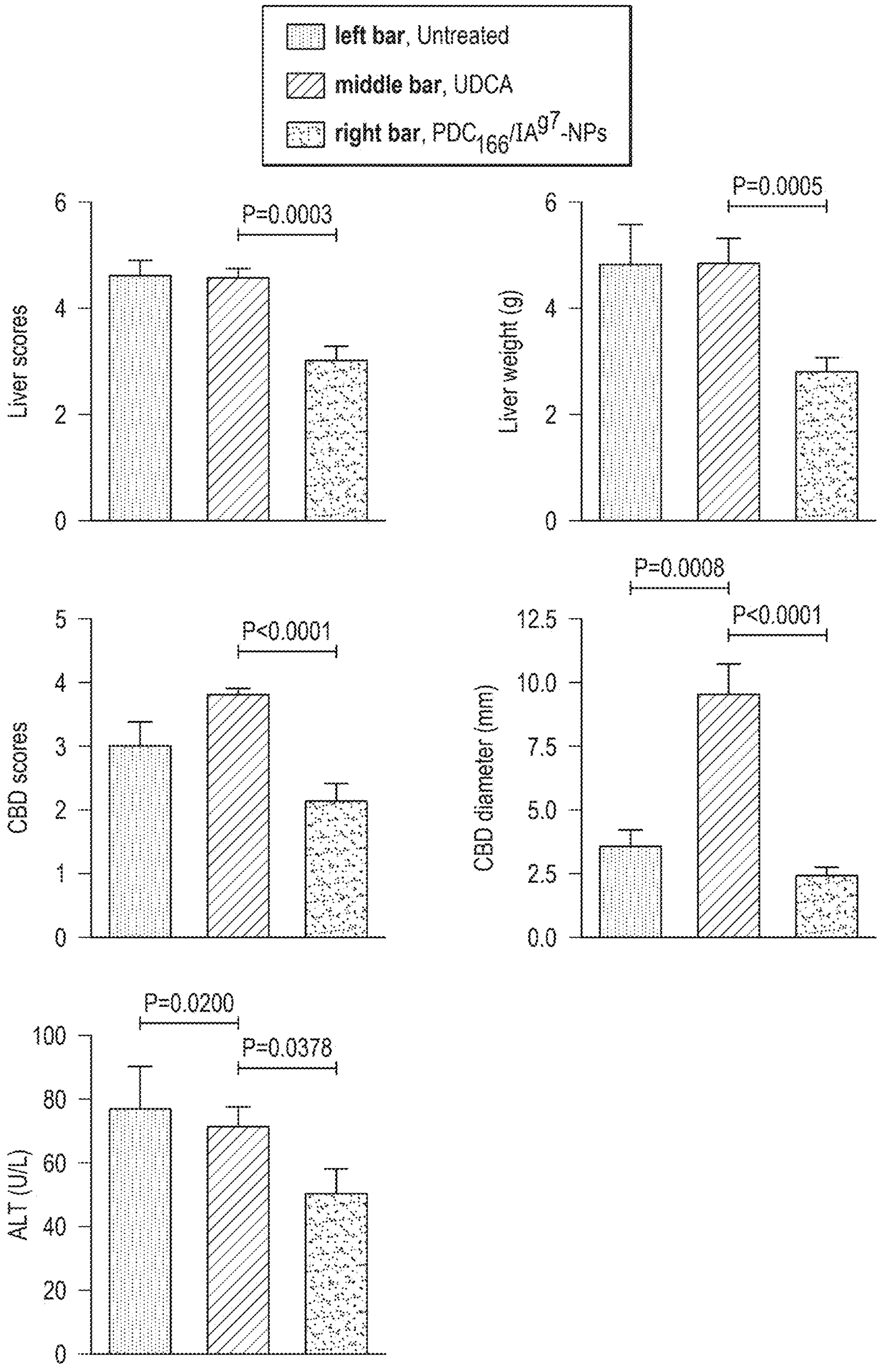
Figure 6E:
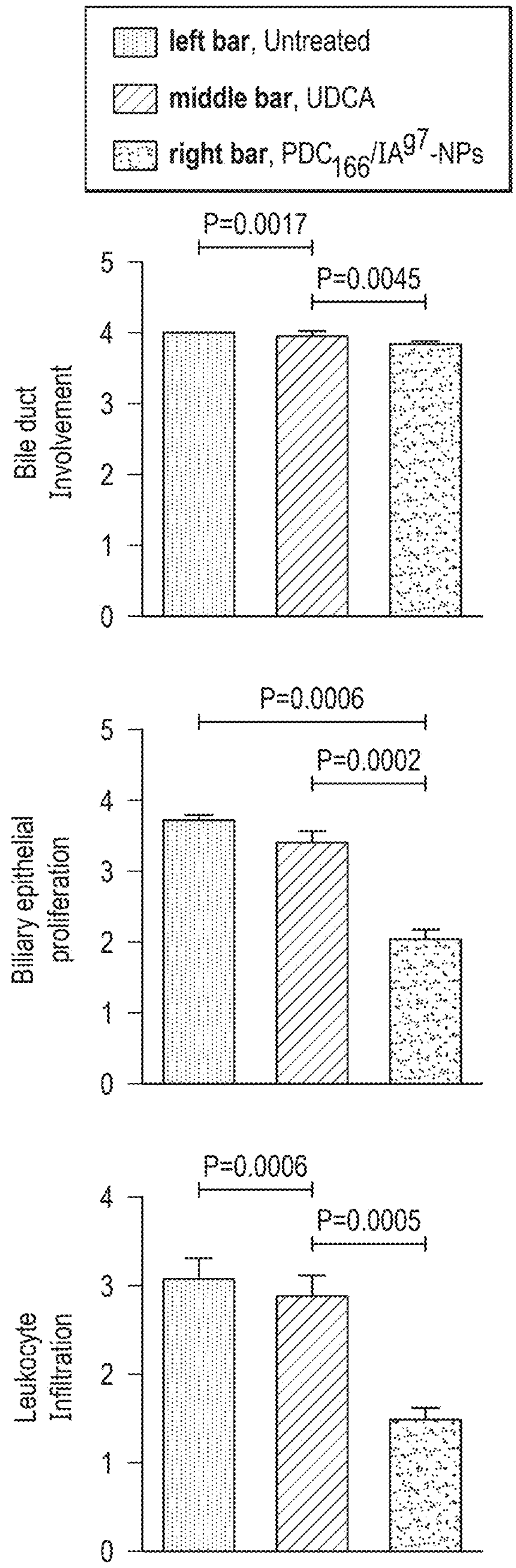

Oral administration of UDCA to 6 weeks-old NOD.c3c4 mice for 9 consecutive weeks via UDCA-supplemented chow had a therapeutic effect on the progression of PBC, as manifested by reductions in liver scores and liver weight, albeit not ALT, CBD scores or CBD diameter (FIG. 6A) and reductions in bile duct involvement and bile duct proliferation, albeit not leukocyte infiltration (FIG. 6B) as compared to untreated mice. However, when UDCA was given at advanced stages of disease progression (24 weeks of age), it had none of these therapeutic effects, except for a very significant reduction in CBD diameter as compared to untreated animals, possibly because of its anti-cholestatic effects (FIGS. 6D and 6E).

Figure 6F:
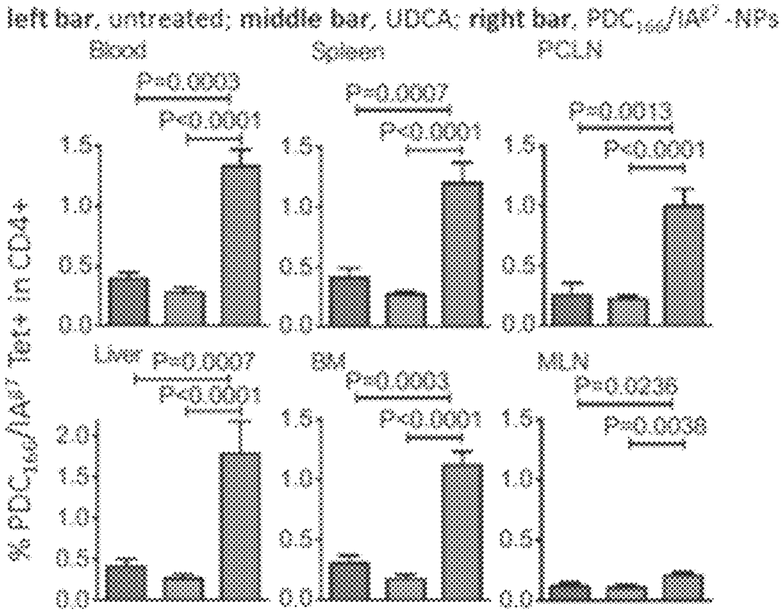

In contrast, PDC-$E2_{166-181}$/$IA^{g7}$-NP treatment had highly significant therapeutic effects in both 6 week-old and 24 week-old animals, as documented by significant reductions in the severity of all read-outs examined (FIGS. 6A-6E). As expected, this was associated with systemic expansion of cognate TR1-like CD4+ T-cells (FIG. 6F).

Example 5—Disease Suppression Requires IL-10, TGFb and CD4+ T Cells

Figure 7A:
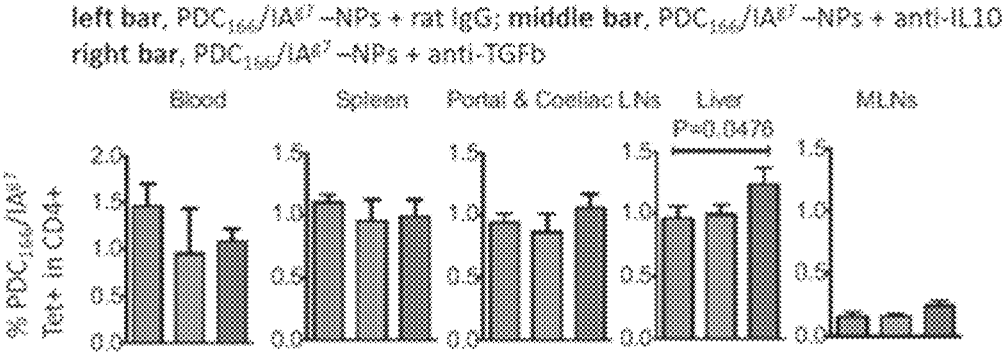
FIGS. 7A-7M illustrate that PBC-relevant pMHC-NPs expand regulatory B-cells.
Figure 7B:
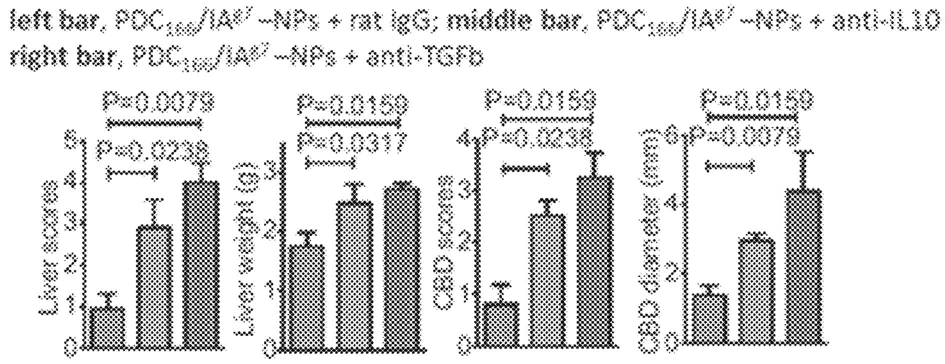
Figure 7C:
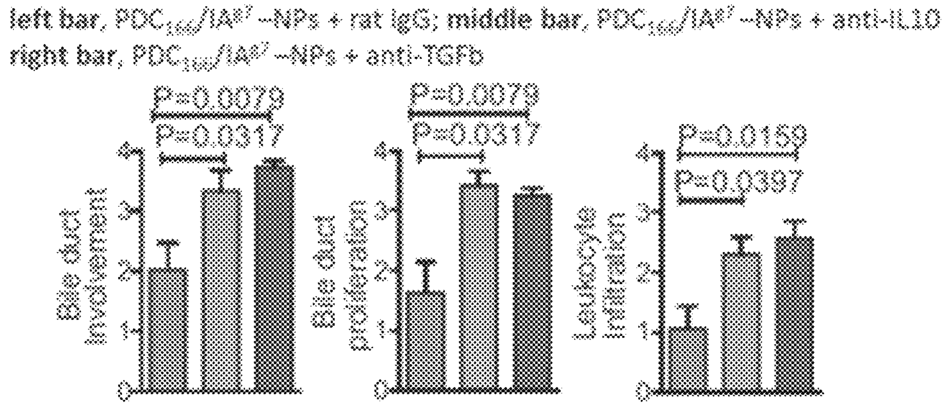
Figure 7D:
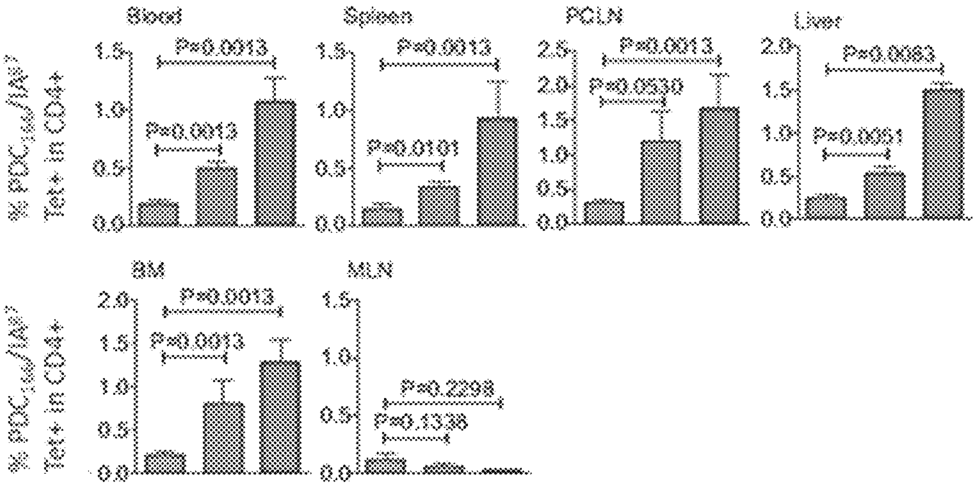
Figure 7E:
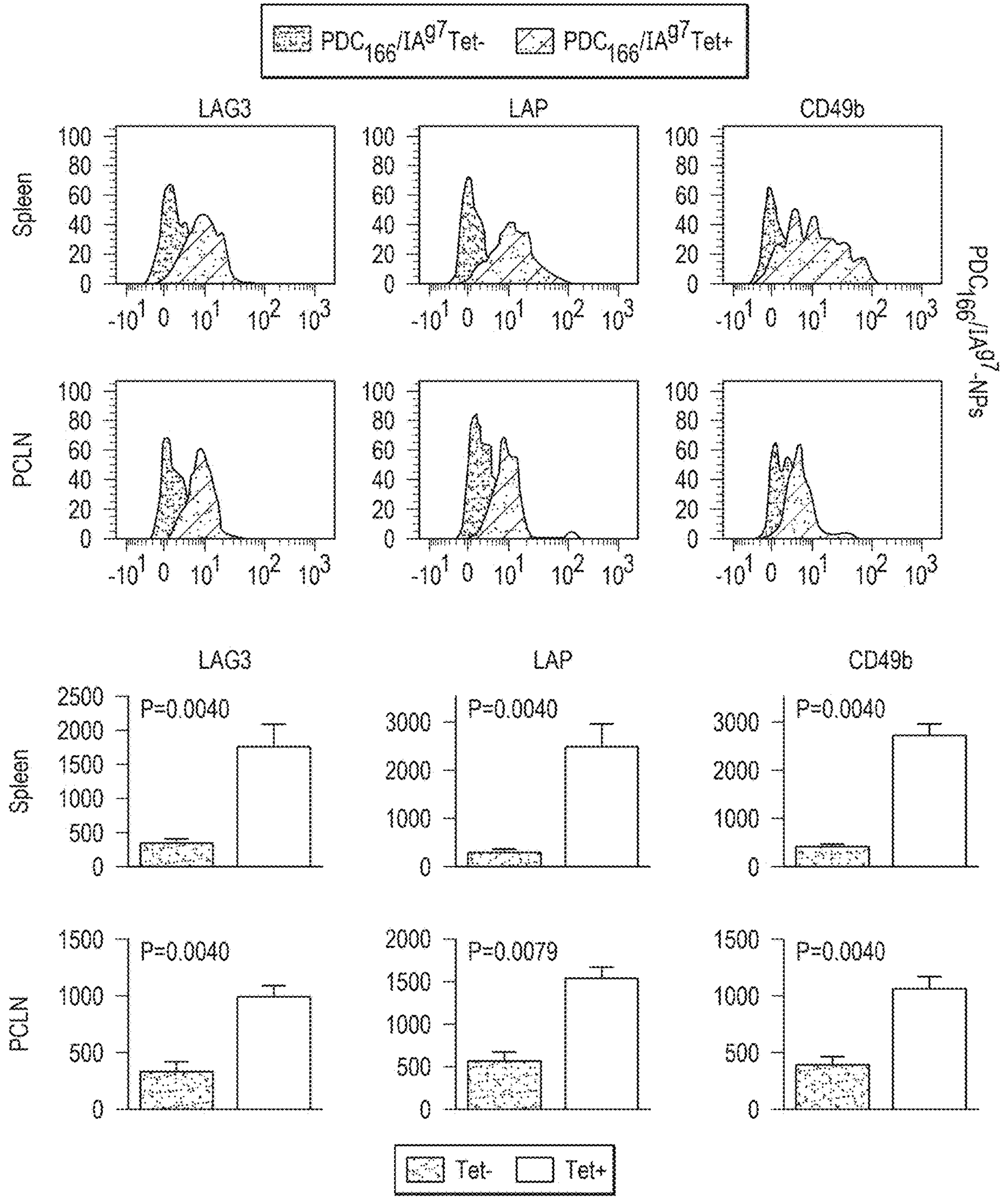
Figure 7F:
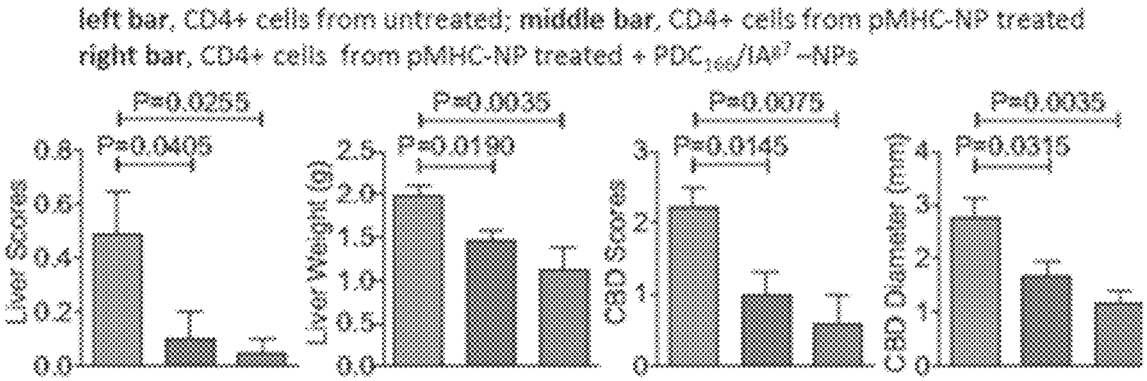

To ascertain if disease reversal by the TR1-like pMHC-NP-expanded PDC-$E2_{166-181}$/$IA^{g7}$ CD4+ T-cells was mediated by the TR1 cytokines IL-10 and/or TGFb, we compared the immunological and therapeutic effects of PDC-$E2_{166-181}$/$IA^{g7}$-NPs on 15 week-old NOD.c3c4 mice treated with blocking anti-IL10 or anti-TGFb mAbs or rat IgG for 5 weeks. Whereas cytokine blockade did not significantly inhibit the expansion of PDC-$E2_{166-181}$/$IA^{g7}$-specific TR1-like CD4+ T-cells (FIG. 7A), it suppressed their therapeutic effects, as compared to age-matched NOD.c3c4 mice treated with rat-IgG (FIGS. 7B and 7C). Purified splenic CD4+ T-cells from PDC-$E2_{166-181}$/$IA^{g7}$-NP-treated NOD.c3c4 mice could transfer disease suppression into NOD.scid.c3c4 hosts reconstituted with splenocytes from sick NOD.c3c4 mice, and treatment of the hosts with PDC-$E2_{166-181}$/$IA^{g7}$-NPs enhanced this effect as shown in FIGS. 7D-7F.

Figure 7G:
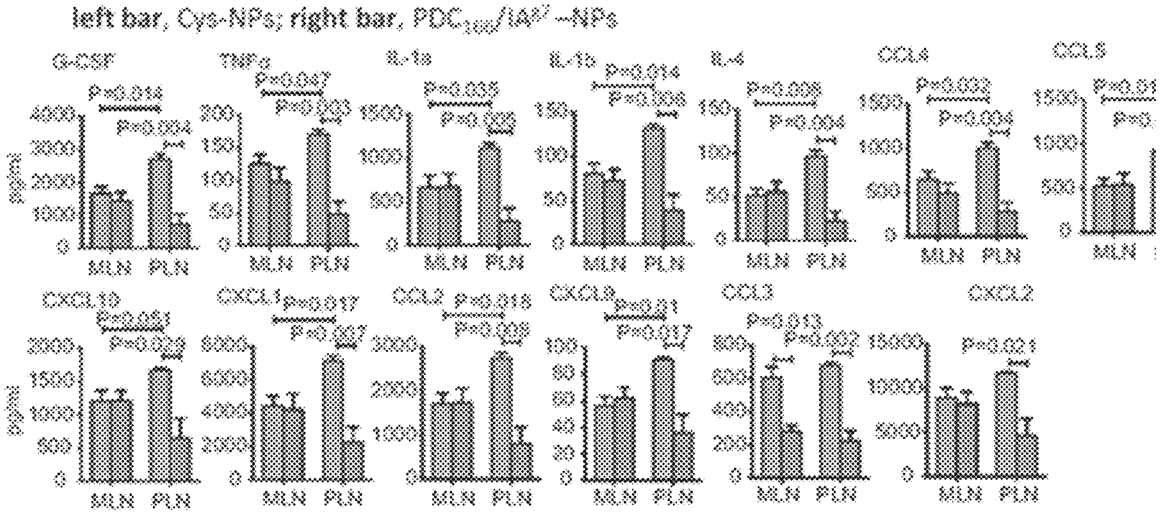
Figure 7H:
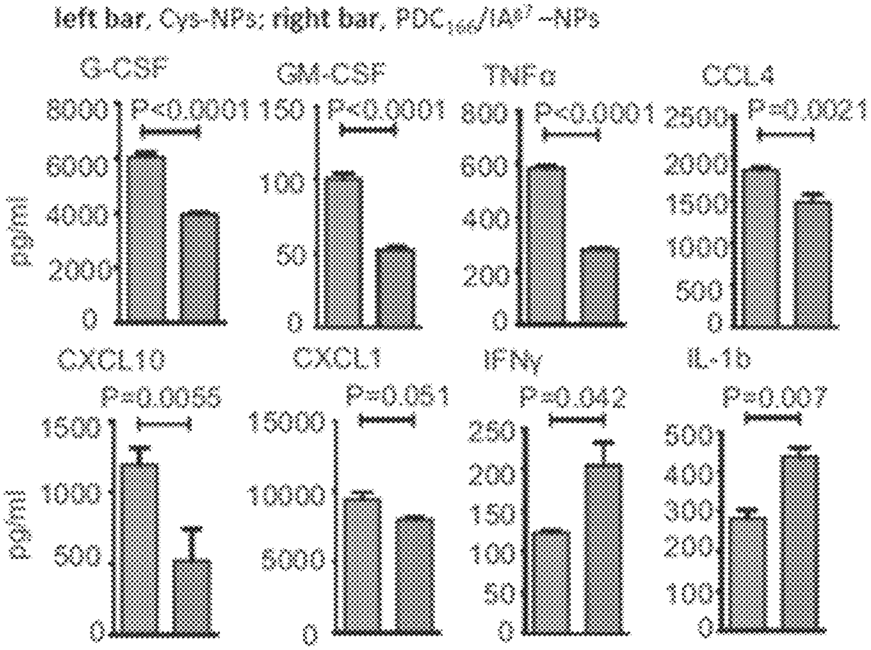

Example 6—Therapy-Induced Suppression of the Pro-Inflammatory Properties of Local and Proximal APCs To ascertain whether reversal of PBC by PDC-$E2_{166-181}$/$IA^{g7}$-NPs was associated with specific suppression of disease-fueling APCs, we compared the cytokine and chemokine profiles of portal (draining) vs. mesenteric (non-draining) lymph node CD11b+ cells and liver Kupffer cells isolated from PDC-$E2_{166-181}$/$IA^{g7}$-NP and control NP-treated animals. LPS-challenged CD11b+ cells from the portal lymph nodes of control NP-treated animals secreted significantly higher levels of a broad range of pro-inflammatory cytokines and chemokines than their mesenteric lymph node counterparts (FIG. 7G). Conversely, the portal lymph node CD11b+ cells of PDC-$E2_{166-181}$/$IA^{g7}$-NP-treated mice secreted significantly lower levels of such pro-inflammatory mediators than both their mesenteric lymph node counterparts and the CD11b+ cells isolated from control-NP-treated animals (FIG. 7G). Likewise, the Kupffer cells isolated from the livers of PDC-$E2_{166-181}$/$IA^{g7}$-NP-treated mice secreted significantly lower levels of some of these mediators (FIG. 7H). Thus, systemic expansion of PDC-E2-specific TR1 CD4+ cells in NOD.c3c4 mice by treatment with PBC-relevant pMHC class II-NPs is associated with dramatic inhibition of the pro-inflammatory properties of local and proximal APC types, likely owing to increased uptake of liver-derived PDC-E2 autoantigenic material.

Figure 7I:
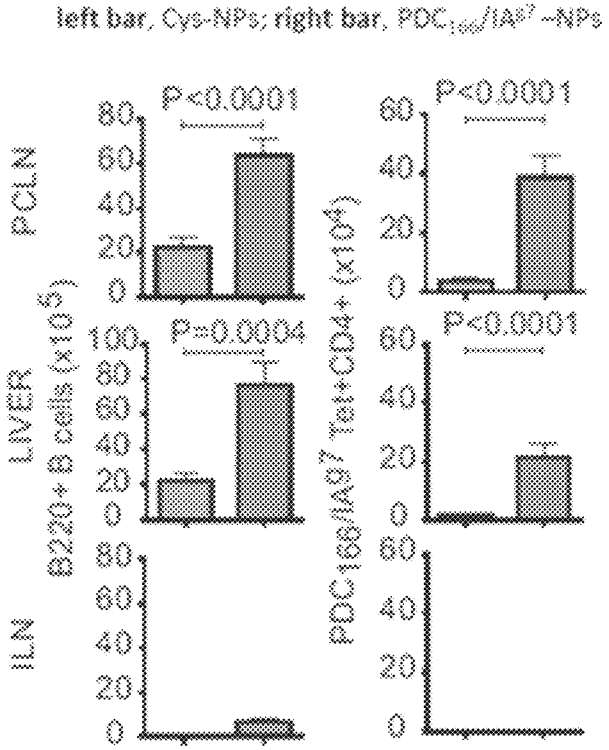
Figure 7J:
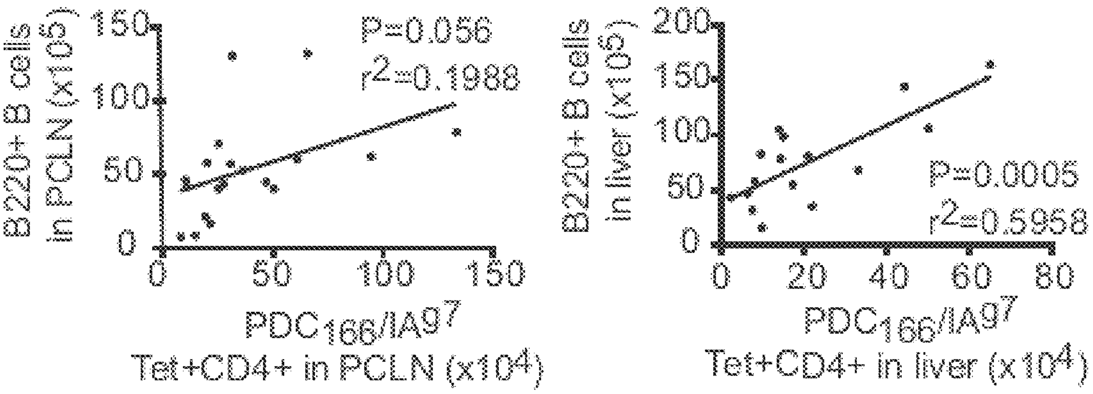

Example 7—PBC-Relevant Nanomedicines Promote Local Formation of Regulatory B Cells Pancreatic beta cell-specific TR1 CD4+ T-cells promote the recruitment of B-cells to the pancreas and its draining lymph nodes, as well as the local formation of anti-diabetogenic IL-10-producing Breg cells. To ascertain if this was also the case for PDC-E2-specific TR1 CD4+ T-cells in the context of PBC, we investigated if there were statistically significant correlations between the absolute numbers of B-cells and PDC-$E2_{166-181}$/$IA^{g7}$-specific TR1 cells in the liver, portal and mesenteric lymph nodes of PDC-$E2_{166-181}$/$IA^{g7}$-NP-treated mice. The livers and the portal, but not the mesenteric lymph nodes of PDC-$E2_{166-181}$/$IA^{g7}$-NP-treated mice harbored significantly higher numbers of PDC-$E2_{166-181}$/$IA^{g7}$-tetramer+ cells and B-cells than those from control-NP-treated animals (FIG. 7I). Furthermore, the tetramer+ and B-cell numbers in both liver and portal lymph nodes were statistically correlated; no such correlation was seen in the mesenteric lymph nodes of PDC-$E2_{166-181}$/$IA^{g7}$-NP-treated mice (FIG. 7J). Thus, enhanced recruitment of cognate TR1 cells to the liver and liver-draining lymph nodes of PDC-E2166-181/$IA^{g7}$-NP-treated mice promotes the local accumulation of B-cells.

Figure 7K:
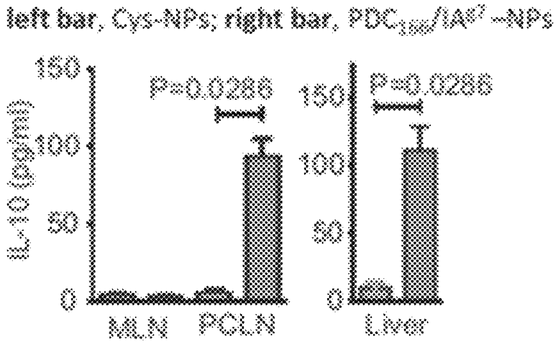

To ascertain whether the liver and portal lymph node B-cells of PDC-$E2_{166-181}$/$IA^{g7}$-NP-treated mice might be enriched for Breg cells, we compared the ability of the corresponding B-cells to produce IL-10 in response to LPS stimulation. The liver and portal, but not the mesenteric lymph node B-cells of PDC-$E2_{166-181}$/$IA^{g7}$-NP-treated mice produced significant levels of IL-10; neither the liver nor the portal lymph node B-cells of control NP-treated animals produced IL-10 (FIG. 7K). Thus, TR1 CD4+ T-cell-enhanced recruitment of B-cells to liver and draining lymph nodes is associated with local formation of IL-10-producing B-cells.

Figure 7L:
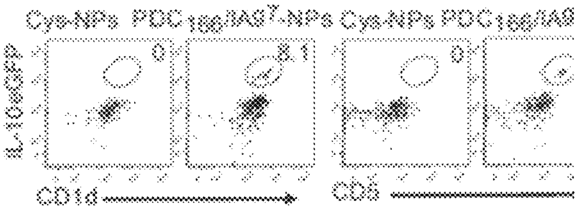
Figure 7M:
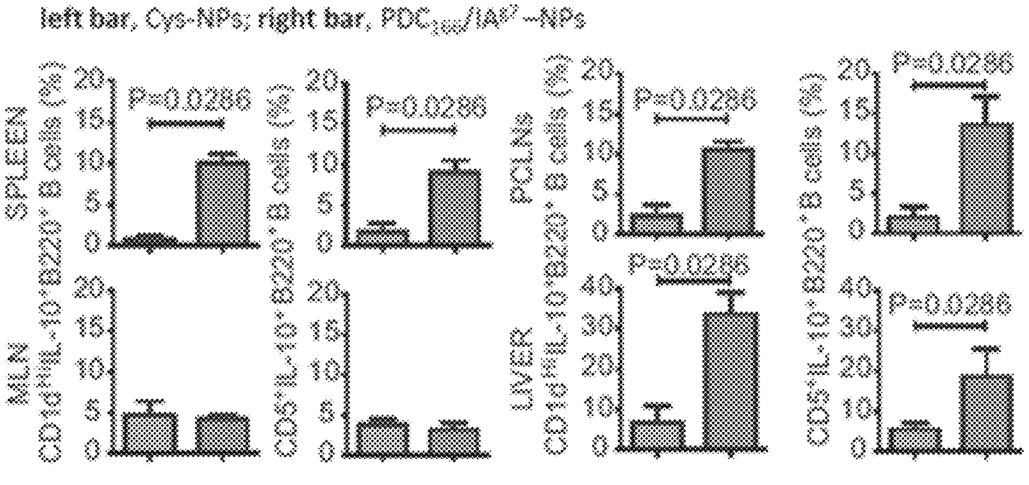
Figure 8A:
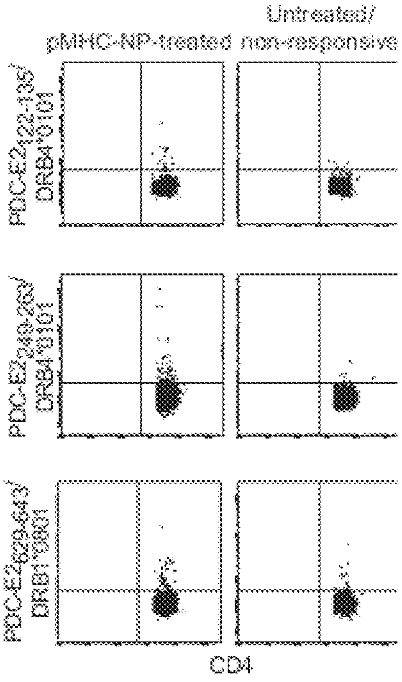
FIGS. 8A-C illustrate expansion of T regulatory cells by PBC-relevant pMHC-NPs in humanized mice.
Figure 8B:
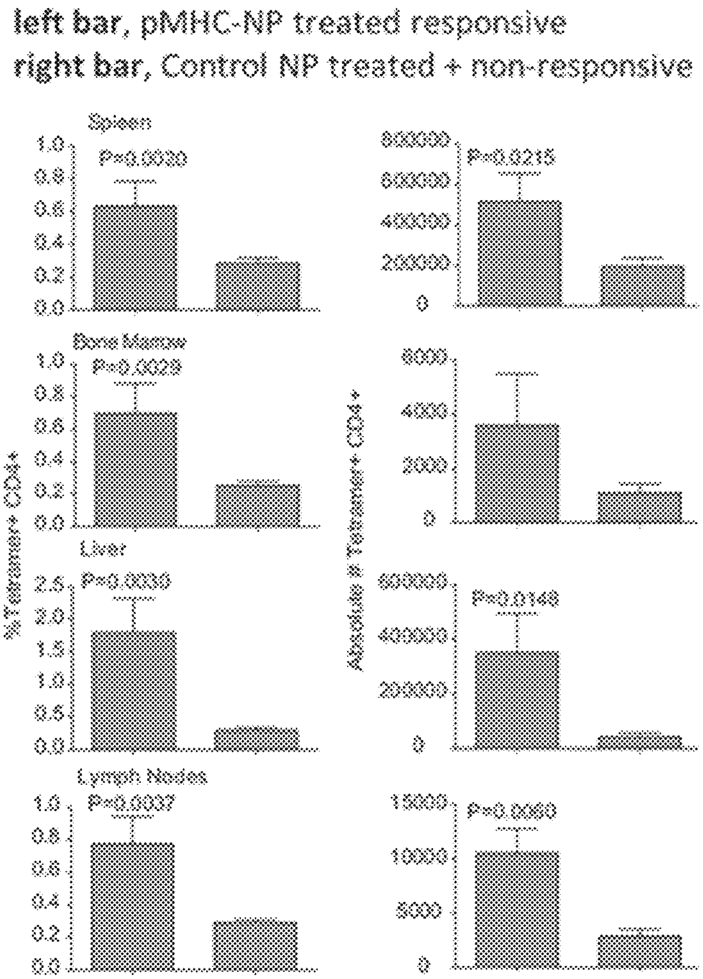
Figure 8C:
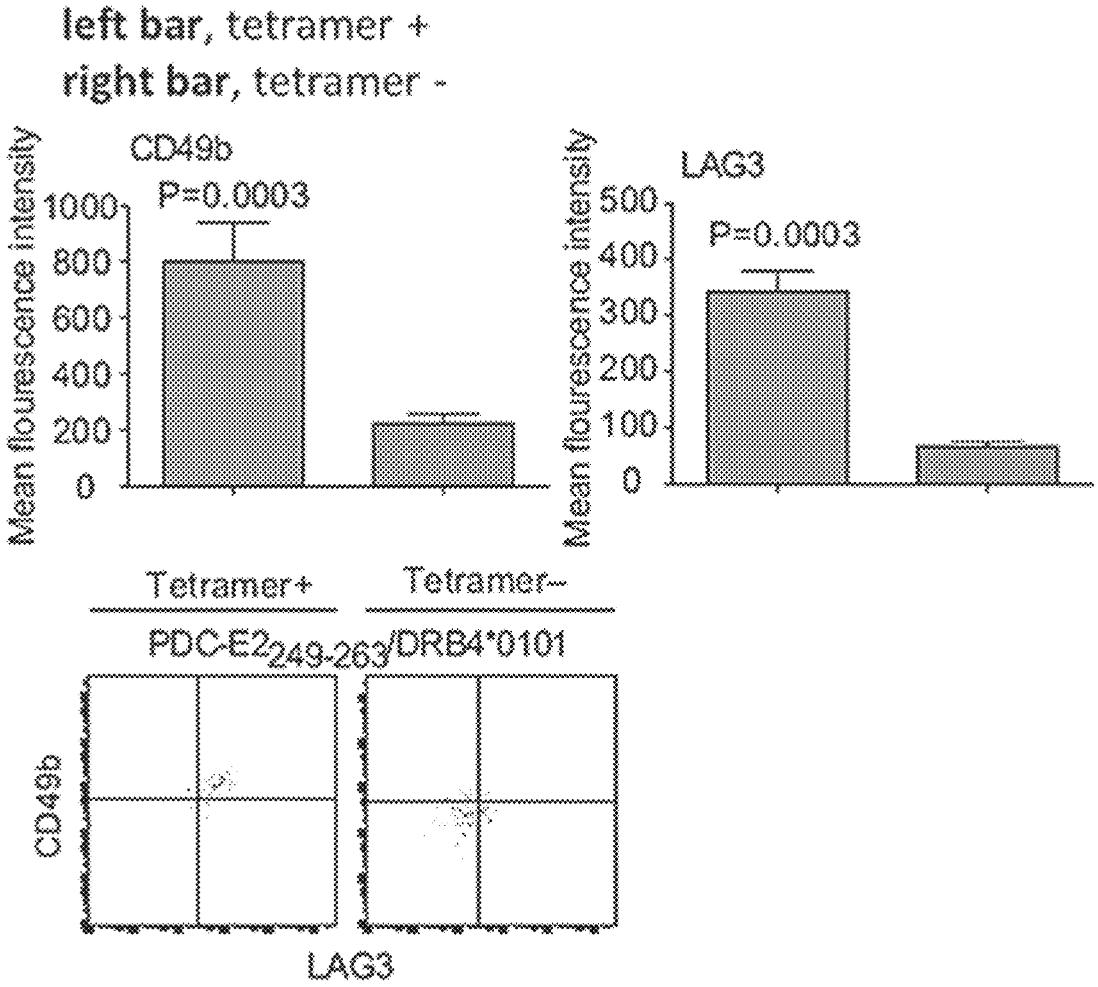

To further substantiate a direct relationship between TR1 cell recruitment and Breg cell formation, we ascertained the ability of PDC-$E2_{166-181}$/$IA^{g7}$-specific TR1 cells that accumulate in the spleen, liver and portal (but not mesenteric) lymph nodes of PDC-$E2_{166-181}$/$IA^{g7}$-treated mice to promote the differentiation of PDC-$E2_{166-181}$ peptide-pulsed conventional (IL-10/eGFP-) B-cells from NOD.I110-eGFP reporter mice into CD1dhigh/CD5+/eGFP+ progeny. As shown in FIGS. 7K-7M, there was a clear formation of Breg cells in spleen, liver and portal lymph nodes (containing cognate TR1 cells) but not in the mesenteric lymph nodes (lacking cognate TR1 cells). When taken together, these results indicate that PDC-E2-specific TR1 cells promote the recruitment and differentiation of conventional B-cells into Breg-like cells.

Example 8—Humanized Mice with PBC

DRB4*0101 and DRB1*0801 have been associated with PBC in some studies. To ascertain the HLA haplotypic diversity in PBC, we did high-resolution HLA-DRB1-typing of 154 patients with PBC from Spain. 40.3% of patients expressed DRB1*0701, 25% were DRB1*0101+ and 14% were DRB1*0801+. Since DRB1*0701+ and haplotypes carrying other DRB1 alleles carry the oligomorphic HLA- DRB4 locus, we also typed these patients for DRB4*0101. 61.7% of all PBC patients carried the DRB4*0101 allele.

Several T-cell epitopes from PDC-E2 binding to two of these HLA-DRB types (DRB4*0101 and DRB1*0801) have been described, including PDC-E2$_{249-262}$ (GDLLAEIETDKATI, SEQ ID NO: 9; DRB4*0101-binder), PDC-E2$_{122-135}$ (GDLIAEVETDKATV, SEQ ID NO: 8; also DRB4*0101-binder), PDC-E2$_{249-263}$ (GDLLAEIETDKATIG, SEQ ID NO: 10); DRB1*0801) and PDC-E2$_{629-643}$ (AQWLAEFRKYLEKPI, SEQ ID NO: 7; DRB1*0801). We therefore expressed and purified PDC-E2$_{122-135}$/DRB4*0101, PDC-E2$_{249-262}$/DRB4*0101, and PDC-E2$_{629-643}$/DRB1*080) 1 complexes and produced iron oxide nanoparticles displaying each of these complexes, as described.

Figure 9A:
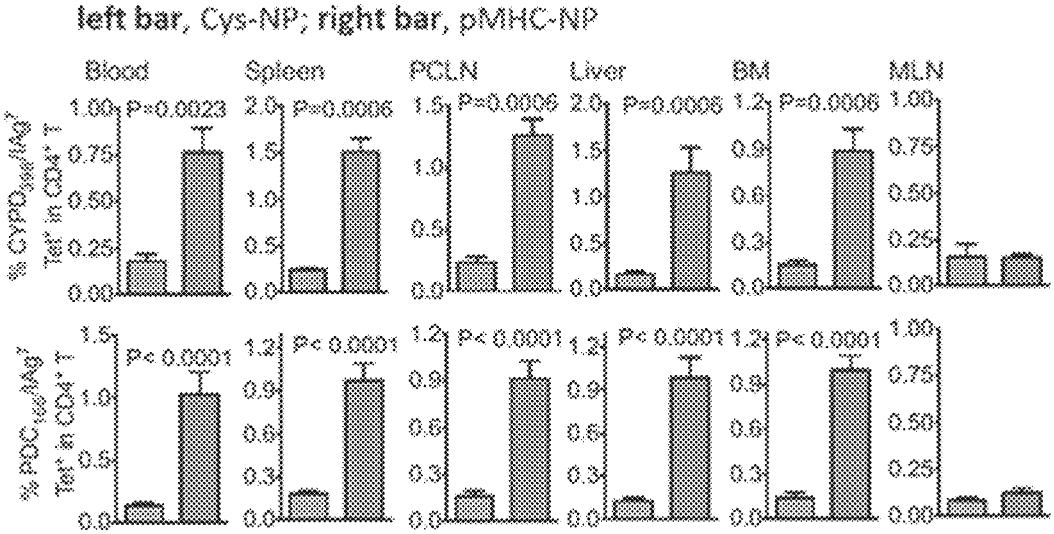
FIG. 9A-9E illustrate that PBC-relevant pMHC-NPs are able to treat disease in models of liver autoimmunity distinct from PBC, in particular, primary sclerosing cholangitis (PSC) and autoimmune hepatitis (AIH).
Figure 9B:
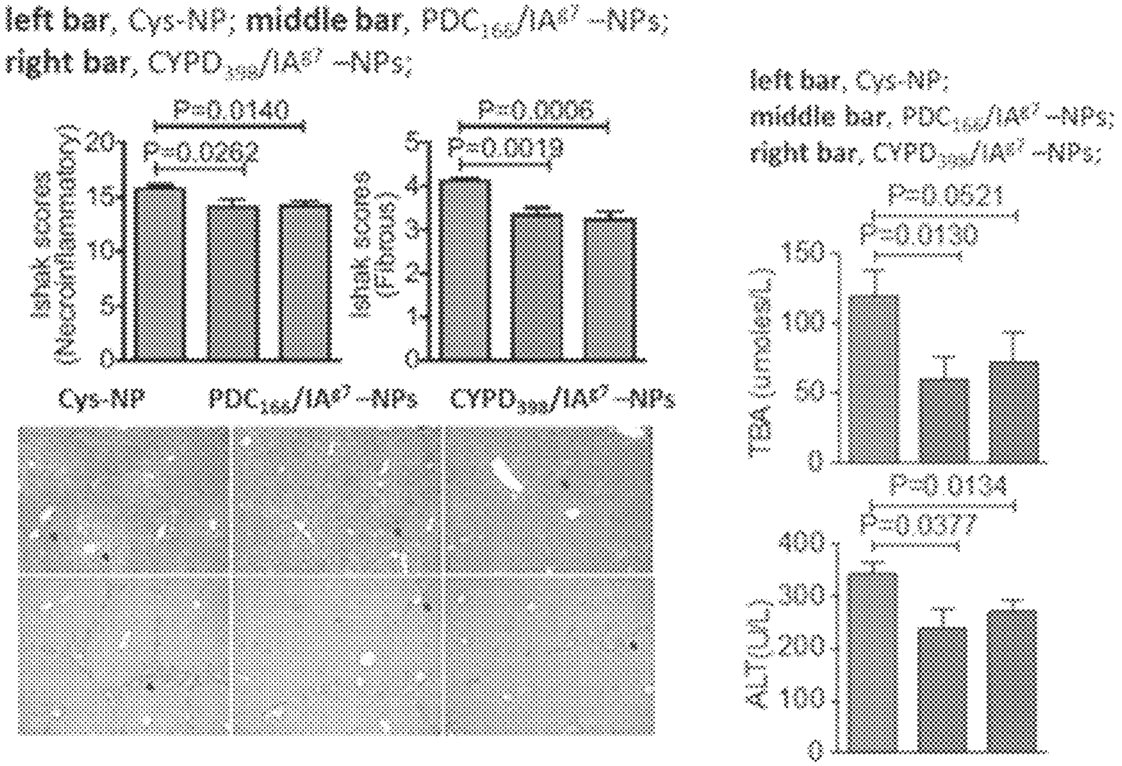
Figure 9C:
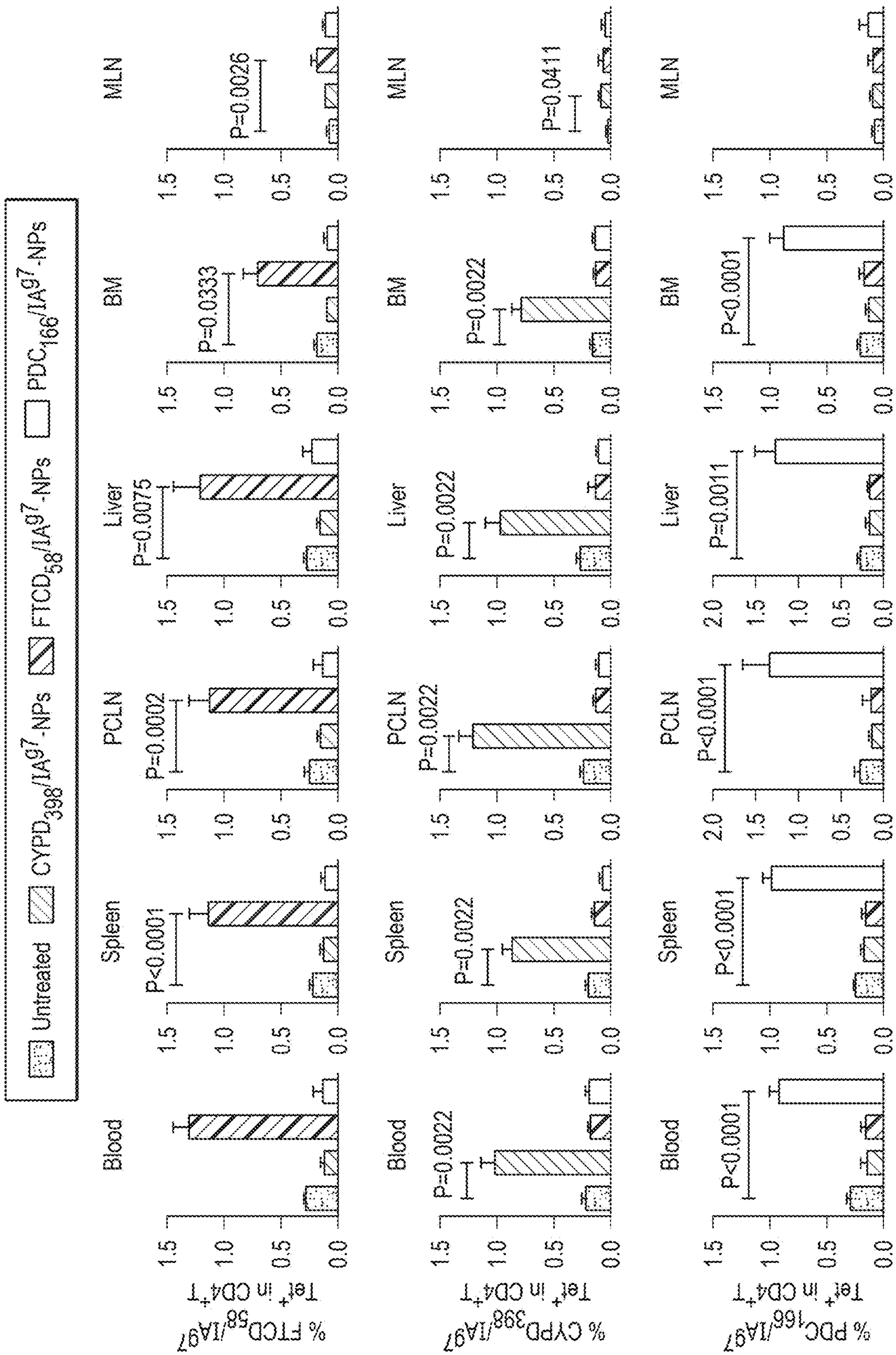
Figure 9D:
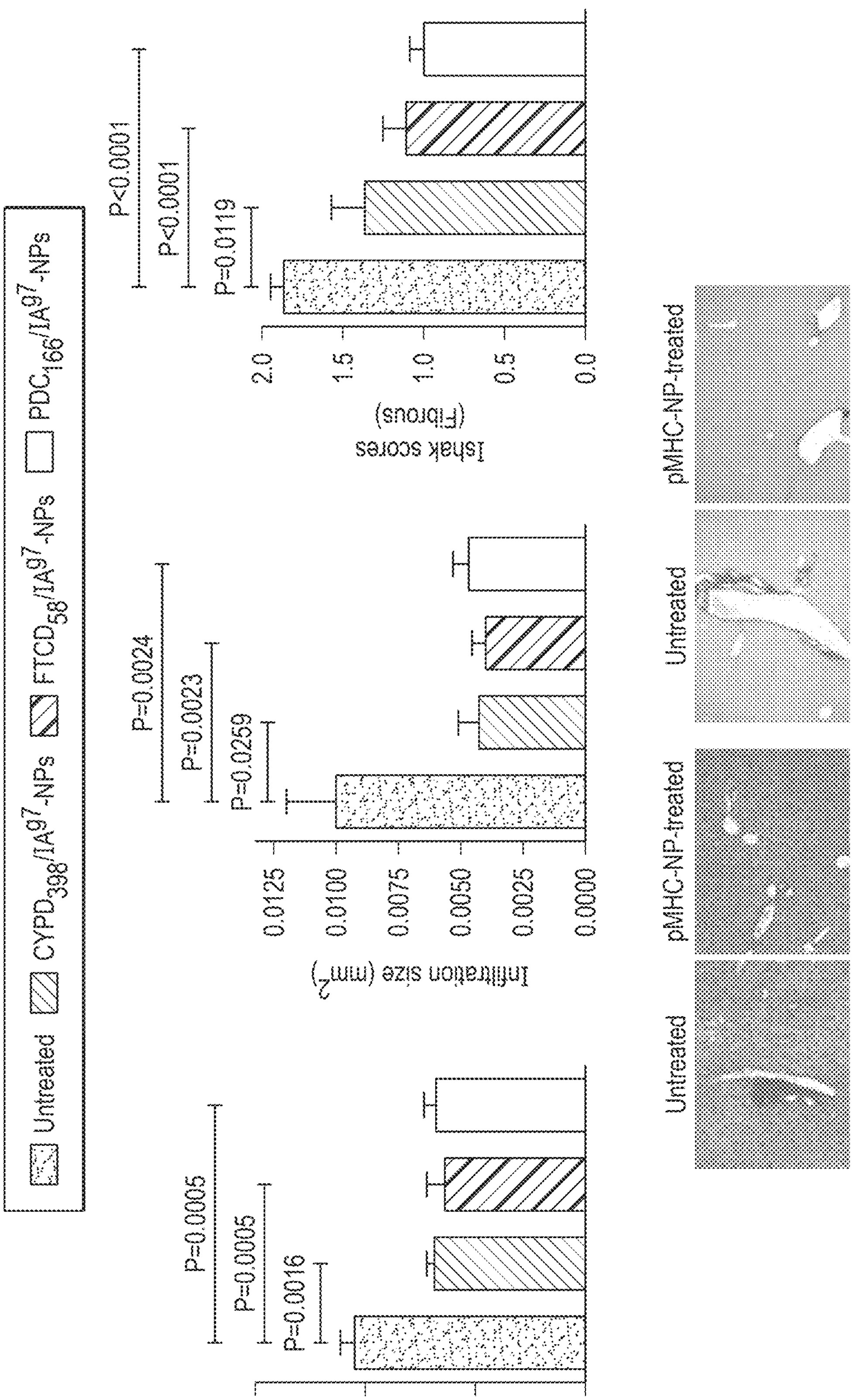
Figure 9E:
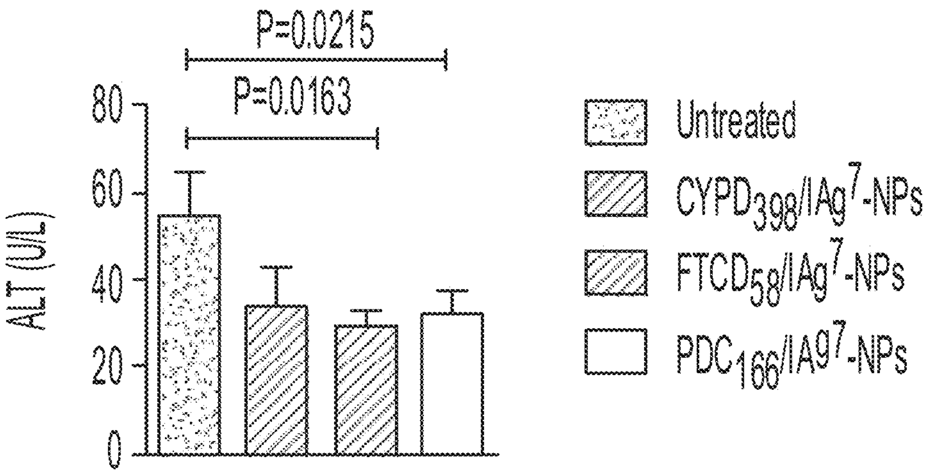
Figure 10A:
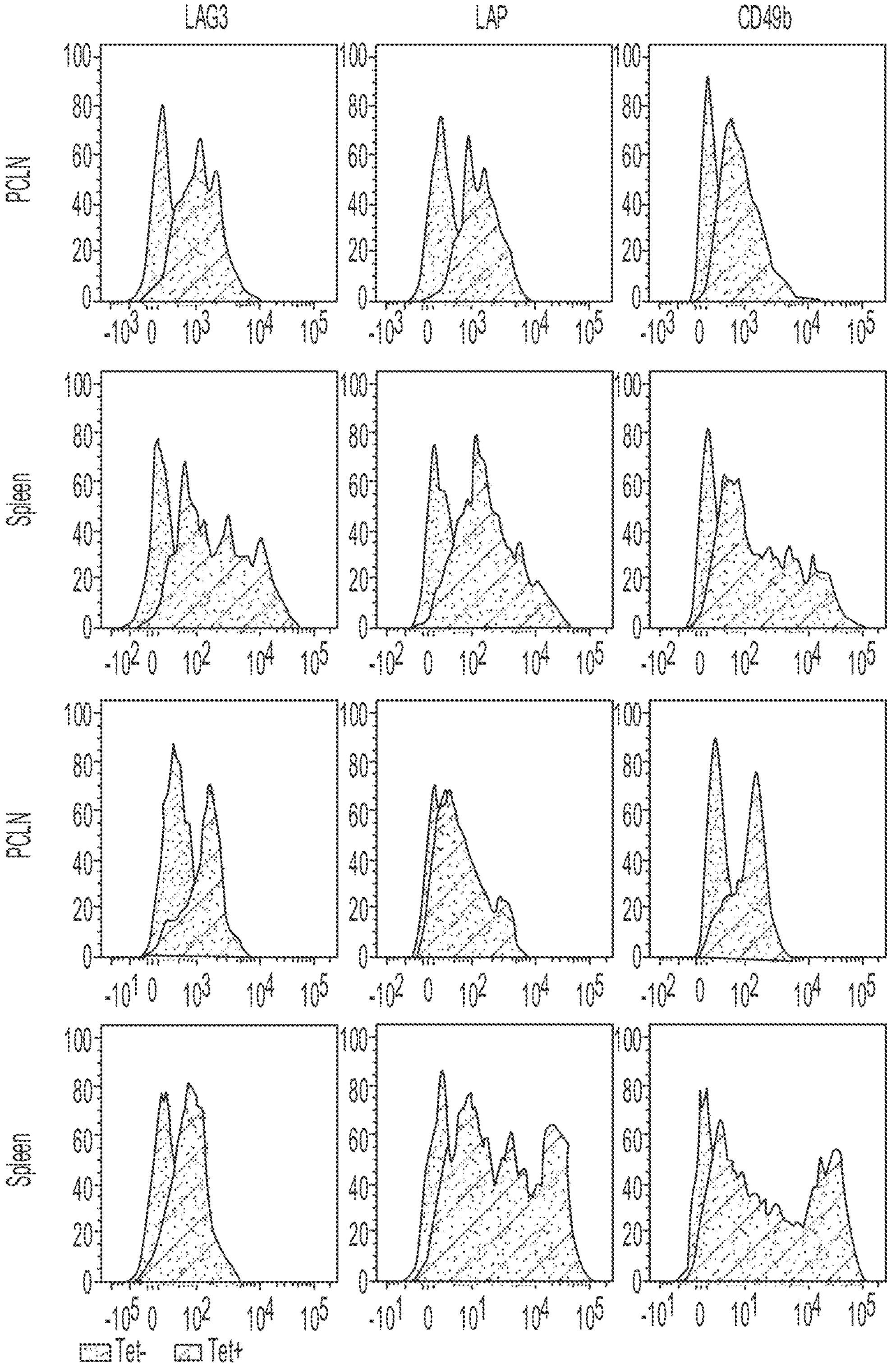
FIGS. 10A-10B illustrate that PBC and AIH-relevant pMHC-NPs expand T regulatory cells in a mouse model of PSC.
Figure 10B:
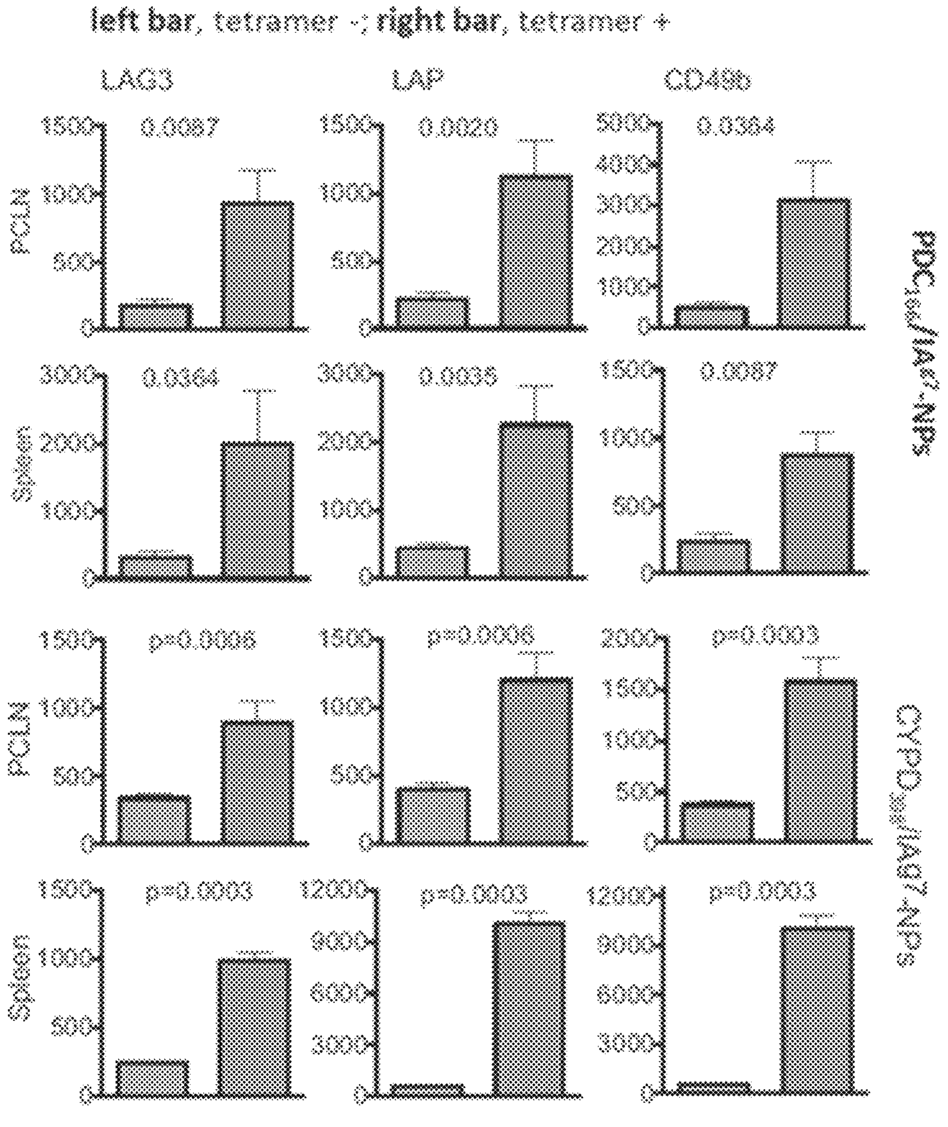
Figure 11A:
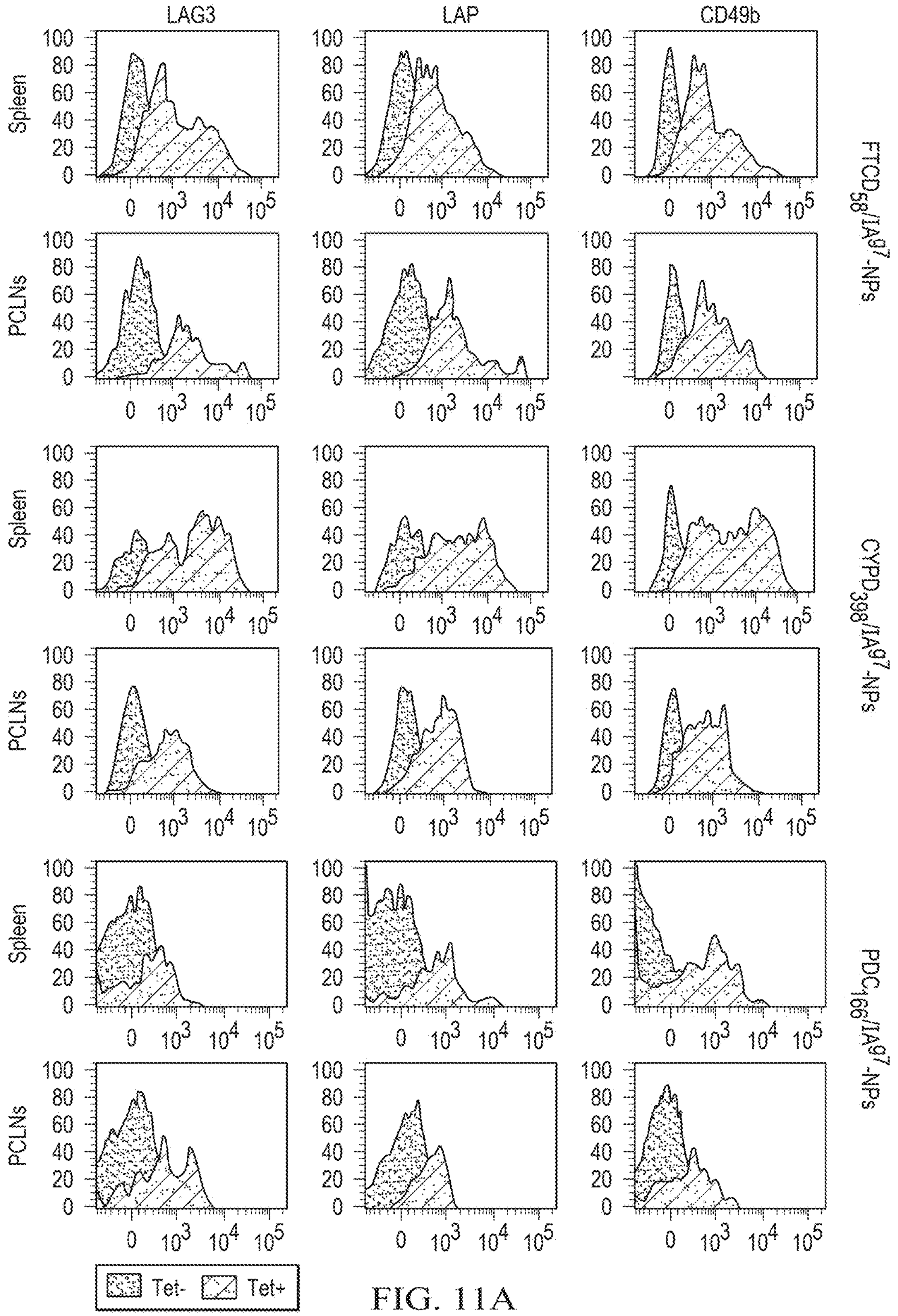
FIGS. 11A-11B illustrate that PBC relevant pMHC-NPs expand T regulatory cells in a mouse model of AIH.
Figure 11B:
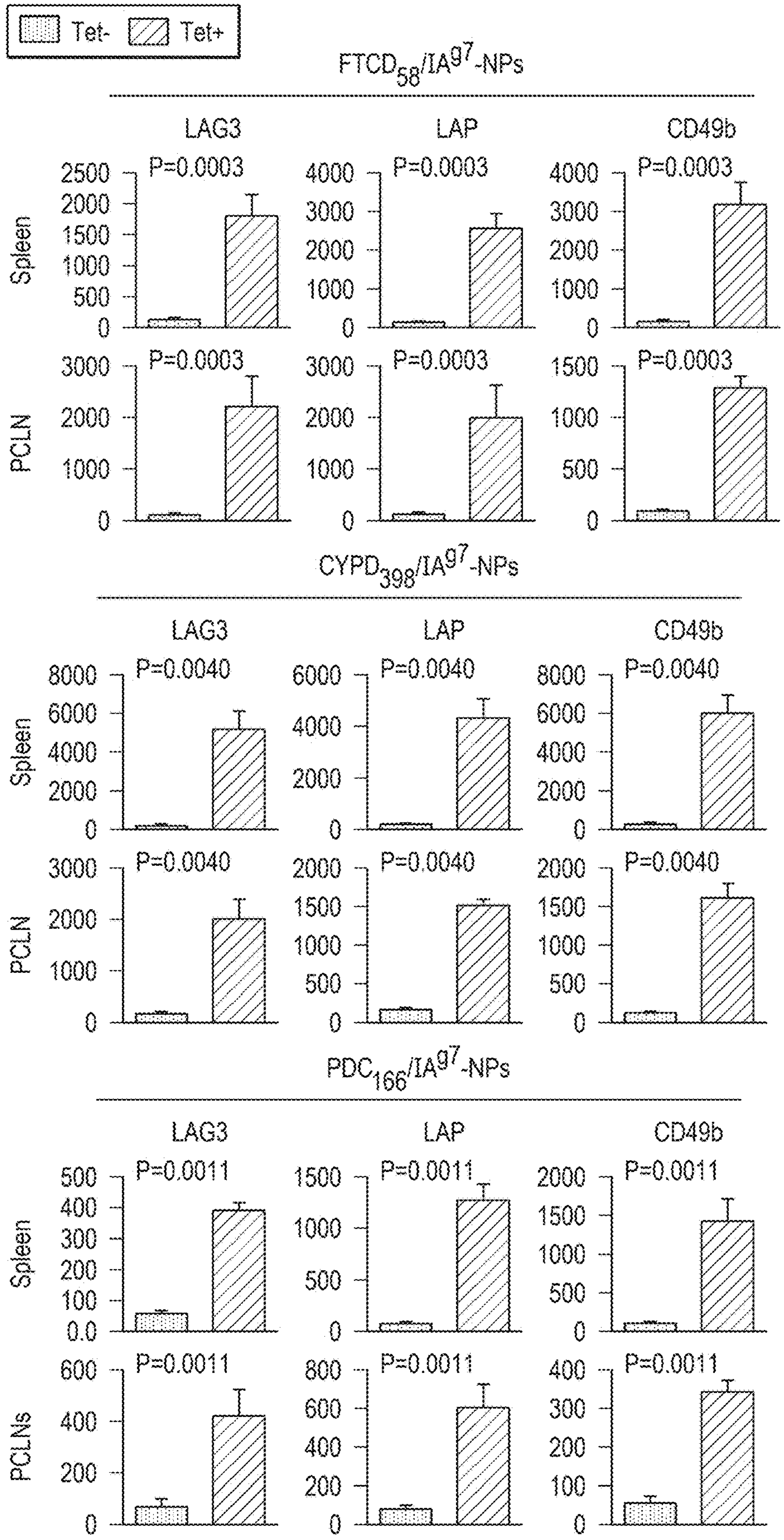

To investigate the translational significance of the above observations, we tested the ability of these three human PBC-relevant pMHC class II-NPs to expand cognate TR1-like CD4+ T-cells in NOD.scid/1/2rg−/−(NSG) hosts reconstituted with PBMCs from 11 DRB4*0101+ and 5 DRB1*0801+ PBC patients (PBL-NSG mice, Tables 2, 3 and 4). PBMC-transfused NSG hosts were then treated with 8-10 doses of 20 μg pMHC-NPs intravenous (twice/week for 5 weeks). One mouse did not engraft and three others died from GvHD prior to termination of treatment. As controls, we transfused a second mouse per donor and treated it with control (non-pMHC-coated NPs). Expansions of cognate CD4+ T-cells were analyzed in the spleens, liver, portal/celiac and axillary lymph nodes. We saw expansion of tetramer+CD49b+ LAG-3+CD4+ T-cells in the spleen and/or liver and LNs from all 6/6 PBL-NSG mice treated with PDC-E2$_{122-135}$/DRB4*0101-NPs, 5/6 PBL-NSG mice treated with PDC-E2$_{249-262}$/DRB4*0101-NPs and 4/5 PBL-NSG mice treated with PDC-E2$_{629-643}$/DRB1*0801-NPs vs. the untreated controls (Tables 2, 3, and 4). Treated responsive mice had significantly higher percentages and absolute numbers of tetramer+ cells in spleen, liver and lymph nodes (FIGS. 9A and 9B) than control NP-treated or unresponsive mice, and these cells expressed the TR1 markers CD49b and LAG-3 (FIG. 9C).

TABLE 2

Table 2 hPDC-E2(122-135)-DRB4-PFM-010616 (30 mcg/dose). DRB4*01:01 patients

| | | | | Spleen | | Liver | | LN | | |
|---|---|---|---|---|---|---|---|---|---|---|
| ID | Gender | Age (yr) | Anti-mitochondrial Abs | % hCD4 Treated # of cells | % hCD4 Untreated # of cells | % hCD4 Treated # of cells | % hCD4 Untreated # of cells | % hCD4 Treated # of cells | % hCD4 Untreated # of cells | Outcome |
| B013 | F | 79 | + | 0.055 | 0.303 | 2.288 | 0.302 | 0.863 | 0.274 | + |
| | | | | | | | | (A) | | |
| | | | | 63756 | 141561 | 300444 | 39069 | 23760 | 154 | |
| B009 | F | 76 | + | 1.253 | 0.291 | 0.199 | 0.307 | * | | + |
| | | | | | (249-NP) | | (249-NP) | | | |
| | | | | 732729 | 308949 | 7047 | 11853 | * | | |
| B005 | M | 74 | + | | | No engraftment | | | | |
| B001 | M | 59 | + | 0.319 | 0.296 | 1.625 | 0.296 | 1.082 | 0.312 | + |
| | | | | | | | | (A) | | |
| | | | | 186539 | 291863 | 256354 | 62871 | 28524 | 1874 | |
| B021 | F | 68 | + | 0.767 | 0.309 | 0.343 | 0.296 | 0.728 | 0.3 | + |
| | | | | | | | | (A) | | |
| | | | | 849816 | 509331 | 18691 | 28993 | 15072 | 5721 | |
| B011 | F | 71 | + | 0.169 | 0.304 | 0.091 | 0.294 | 0.425 | 0.291 | + |
| | | | | | | | | (L) | | |
| | | | | 202383 | 209370 | 6658 | 151772 | 120 | 755 | |
| B018 | F | 56 | + | | | Dead | | | | |
| B012 | F | 71 | + | 0.709 | 0.298 | | | 0.722 | 0.290 | + |
| | | | | | | | | (A) | (A) | |
| | | | | 341920 | 124050 | ND | | 5602 | 2101 | |

TABLE 3

Table 3 hPDC-E2(249-262)-DRB4-PFM-010616 (40 mcg/dose). DRB4*01:01 patients

| | | | | Spleen | | Liver | | LN | | |
|---|---|---|---|---|---|---|---|---|---|---|
| ID | Gender | Age (yr) | Anti-mitochondrial Abs | % hCD4 Treated # of cells | % hCD4 Untreated # of cells | % hCD4 Treated # of cells | % hCD4 Untreated # of cells | % hCD4 Treated # of cells | % hCD4 Untreated # of cells | Outcome |
| B013 | F | 79 | + | 0.078 | 0.31 | 4.925 | 0.295 | 0.621 | 0.245 | + |
| | | | | | | | | (L) | | |
| | | | | 105174 | 164589 | 1124257 | 35712 | 33121 | 275 | |
| B009 | F | 76 | + | 0.028 | 0.307 | 0.515 | 0.297 | * | | + |
| | | | | | (122-NP) | | (122-NP) | | | |
| | | | | 31807 | 192099 | 20215 | 10866 | * | | |
| B004 | F | 63 | + | 0.427 | 0.294 | 0.094 | 0.315 | 0.089 | 0.293 | + |
| | | | | | | | | (A) | | |
| | | | | 268565 | 228575 | 2990 | 299574 | 526 | 11251 | |

TABLE 3-continued

Table 3 hPDC-E2(249-262)-DRB4-PFM-010616 (40 mcg/dose). DRB4*01:01 patients

| | | | | Spleen | | Liver | | LN | | |
|---|---|---|---|---|---|---|---|---|---|---|
| ID | Gender | Age (yr) | Anti-mitochondrial Abs | % hCD4 Treated # of cells | % hCD4 Untreated # of cells | % hCD4 Treated # of cells | % hCD4 Untreated # of cells | % hCD4 Treated # of cells | % hCD4 Untreated # of cells | Outcome |
| B012 | F | 70 | + | 0.264 | 0.297 | 0.078 | 0.3 | 0.059 (L) | 0.313 | – |
| | | | | 41467 | 147568 | 1034 | 24584 | 1513 | 6160 | |
| B001 | M | 59 | + | | | | Dead | | | |
| B021 | F | 68 | + | 1.612 | 0.31 | 1.943 | 0.289 | 2.589 (L) | 0.32 | + |
| | | | | 1368420 | 514802 | 1174100 | 35690 | 9491 | 788 | |
| B019 | F | 73 | + | | | | Dead | | | |
| B014 | F | 72 | + | 0.709 | 0.295 | 0.588 | 0.305 | 1.096 (A) | 0.299 | + |
| | | | | 604820 | 162521 | 76559 | 30198 | 5557 | 1271 | |
| | | | | 416501 | 181855 | 4960 | 4517 | 3740 | 2232 | |

TABLE 4

Table 4 hPDC-E2(629-643)-DR8-PFM-010616 (30 mcg/dose). DRB1*08:01 patients

| | | | | Spleen | | Liver | | LN | | |
|---|---|---|---|---|---|---|---|---|---|---|
| ID | Gender | Age (yr) | Anti-mitochondrial Abs | % hCD4 Treated # of cells | % hCD4 Untreated # of cells | % hCD4 Treated # of cells | % hCD4 Untreated # of cells | % hCD4 Treated # of cells | % hCD4 Untreated # of cells | Outcome |
| B022 | F | 72 | + | 0.024 | 0.3 | 0.619 | 0.293 | No cells | 0.295 (L) | + |
| | | | | 662 | 48190 | 26 | 29984 | | 260 | |
| B021 | F | 68 | + | 0.725 | 0.317 | 3.185 | 0.3 | 1.103 (A) | 0.301 | + |
| | | | | 1095456 | 562089 | 455716 | 36134 | 22752 | 8080 | |
| B020 | F | 70 | + | 0.303 | 0.308 | 0.18 | 0.297 | No cells | | – |
| | | | | 38207 | 114160 | 19765 | 46701 | | | |
| B025 | F | 69 | + | 0.404 | 0.308 | 2.895 | 0.294 | 0.501 (A) | 0.319 (A) | + |
| | | | | 59552 | 49721 | 78551 | 8747 | 740 | 466 | |
| B023 | F | 75 | + | 0.745 | 0.292 | 0.283 | 0.292 | 0.371 (A) | 0.297 | + |

Example 9—Disease Versus Organ Specificity

Given the large autoantigenic load of an organ such as the liver as compared to smaller organs, like the endocrine pancreas, and the fact that PDC-E2 is an autoantigen expressed in virtually all cell types, our results begged the question of whether PBC-relevant nanomedicines (i.e. PDC-$E2_{166-181}/IA^{g7}$-NP) are disease (PBC)- or organ (liver)-specific, or also able to blunt liver-distal inflammation.

Primary sclerosing cholangitis (PSC) is a chronic cholestatic disease characterized by inflammation of intra- and extra-hepatic bile ducts leading to a fibro-obliterative cholangitis with periductal fibrosis around medium and large bile ducts and degenerative changes of the biliary epithelium, which progresses to portal and biliary cirrhosis and finally liver cirrhosis. Human PSC is frequently associated with inflammatory bowel disease and accompanied by a high prevalence of atypical perinuclear anti-neutrophil cytoplasmic (pANCA) but not anti-mitochondrial autoantibodies. See Fickert, P. et al. Characterization of animal models for primary sclerosing cholangitis (PSC). *J. Hepatol.* 60, 1290-1303. Abcb4 gene knockout mice spontaneously develop a form of sclerosing cholangitis that is remarkably similar to human PSC and is caused by damage of bile duct cells by impaired biliary phospholipid secretion. See Pollheimer, M. J. & Fickert, P. Animal models in primary biliary cirrhosis and primary sclerosing cholangitis. *Clin. Rev. Allergy Immunol.* 48, 207-217, doi: 10.1007/s12016-014-8442-y (2015).

Autoimmune Hepatitis (AIH) is characterized by a portal mononuclear cell infiltration of the liver parenchyma that is associated with presence of anti-nuclear and/or smooth muscle (AIH type 1) or anti-liver kidney microsomal or anti-liver cytosol type 1 autoantibodies, which specifically target the microsomal cytochrome P450IID6 (CYP2D6) or formiminotransferase cyclodeaminase (FTCD), respectively (AIH Type 2). See Longhi, M. S. et al. Aetiopathogenesis of autoimmune hepatitis. *J. Autoimmun.* 34, 7-14. Recently, it has been shown that infection of NOD mice with replication-defective adenoviruses encoding the human liver autoantigen formiminotransferase cyclodeaminase (Ad-FTCD) triggers a form of chronic autoimmune hepatitis that resembles AIH type 2. See Hardtke-Wolenski, M. et al. Genetic predisposition and environmental danger signals initiate chronic autoimmune hepatitis driven by CD4+ T cells. *Hepatology* 58, 718-728.

The large bile duct and parenchymal liver damage that underlie PSC and AIH may trigger the release of PDC-E2 and the priming of cognate autoreactive CD4+ T-cells capable of responding to PDC-$E2_{166-181}$/$IA^{g7}$-NP therapy. If so, therapy should trigger the expansion of TR1-like PDC-$E2_{166-181}$/$IA^{g7}$-specific CD4+ T-cells and suppression of local inflammation upon recognition of local and proximal PDC-E2-loaded APCs. Alternatively, the amount of PDC-E2 shed into the inflammatory milieu in PSC and/or AIH may be insufficient to generate PDC-$E2_{166-181}$/$IA^{g7}$-experienced CD4+ T-cells, hence an immunological and therapeutic response to PDC-$E2_{166-181}$/$IA^{g7}$-NPs.

To test these alternative possibilities, we first investigated the ability of PDC-$E2_{166}$-181/$IA^{g7}$-NPs to trigger the expansion of cognate TR1-like CD4+ T-cells and revert PSC in NOD.$Abcb4^{-/-}$ mice. Remarkably, PDC-$E2_{166-181}$/$IA^{g7}$-NP triggered the systemic expansion of cognate TR1-like CD4+ T-cells in these animals and reverted established disease, as compared to control NP-treated controls as shown in FIGS. 10A-10B and FIGS. 11A and 11B.

We next investigated whether this was also true in Ad-FTCD-induced AIH. We compared the pharmacodynamic and therapeutic activities of both $mFTCD_{58-72}$/$IA^{g7}$-NPs and $CYPD_{398-412}$/$IA^{g7}$-NPs (AIH-relevant) with those of PDC-$E2_{166-181}$/$IA^{g7}$-NPs (PBC-relevant) in NOD mice infected with Ad-FTCD. All three compounds triggered the formation and expansion of cognate TR1-like CD4+ T-cells in these animals to a similar extent (FIG. 10C and FIGS. 12A and 12B) as compared to untreated Ad-FTCD-infected animals, and this was accompanied by significant reductions in liver inflammation as shown in FIGS. 10C and 10D, and serum ALT levels as shown in FIG. 10E.

Figure 12A:
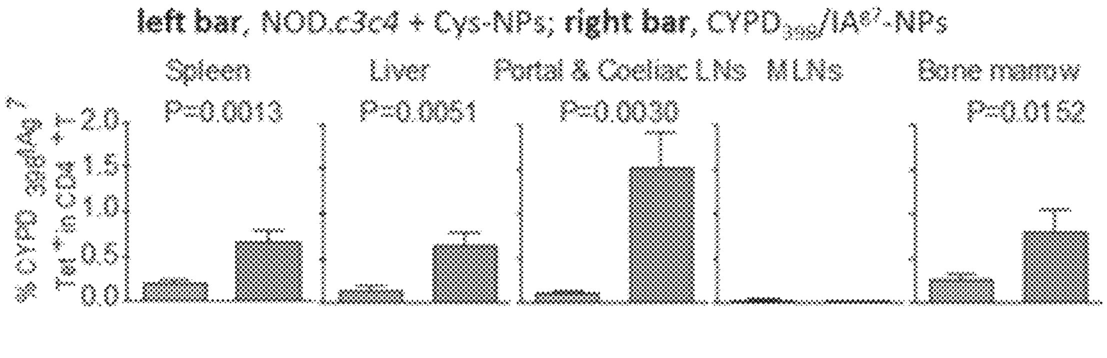
FIGS. 12A-12C illustrate the ability of ubiquitous autoantigen based pMHC-NPs to blunt liver inflammatory disease in an organ rather than disease-specific manner.
Figure 12B:
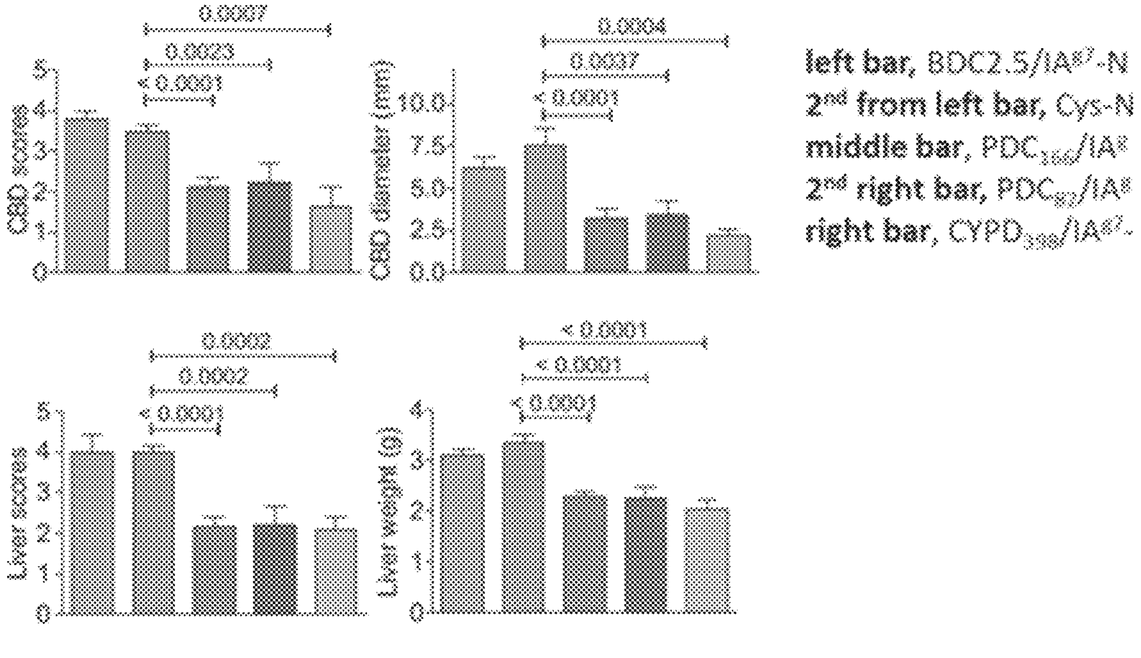
Figure 12C:
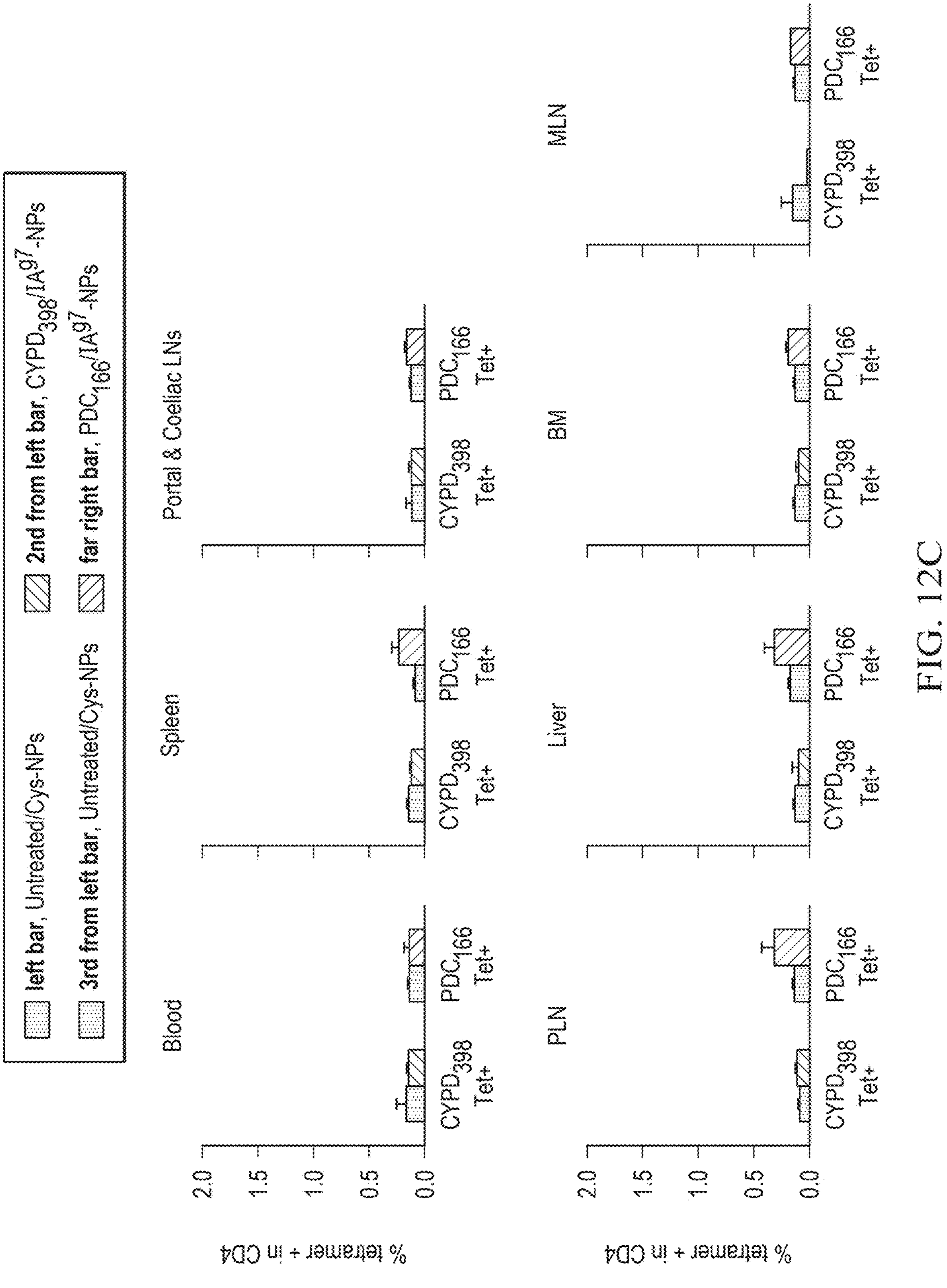

This ability of ubiquitous autoantigen-based pMHC-nanomedicines to blunt liver autoimmunity in an organ rather than disease-specific manner also occurred in NOD.c3c4 mice treated with $CYPD_{398-412}$/$IA^{g7}$-NPs (FIGS. 12A-12C). In fact, the latter were as efficient as PDC-$E2_{166-181}$/$IA^{g7}$-NPs at expanding cognate TR1 cells (FIG. 12A), and blunting PBC in 15 week-old mice (FIG. 12B). In contrast, neither PDC-$E2_{166-181}$/$IA^{g7}$-NPs nor $CYPD_{398-412}$/$IA^{g7}$-NPs triggered the expansion of cognate TR1 CD4+ T-cells in 10 week-old pre-diabetic NOD mice (FIG. 12C), unlike the case for beta cell-specific BDC2.5/$IA^{g7}$-, $IGRP_{4-22}$/$IA^{g7}$- or $IGRP_{128-145}$/$IA^{g7}$-NPs, presumably because the PDC-E2 and CYPD content in beta cells is insufficient to prime the activation of cognate CD4+ T-cells.

Collectively, these observations suggest that abundant levels of PDC-E2 (mitochondrial), $CYPD_2D6$ and FTCD antigens (Golgi-resident or cytoplasmic, respectively) are delivered to local and proximal APCs upon hepatocyte (AIH) or bile duct epithelial cell damage (PBC and PSC), enabling autoreactive CD4+ T-cell priming, cognate TR1 cell generation by pMHC-NPs and suppression of local and proximal autoantigen-loaded APCs.

Example 10—Therapeutic Effects in Another PBC Model

Figure 13A:
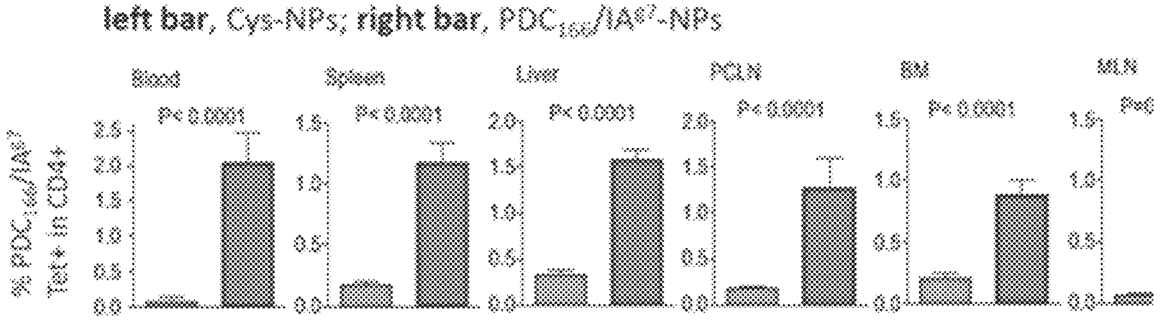
FIGS. 13A-13C illustrate therapeutic effects of PBC-relevant pMHCII-NPs in (NODxB6.Ifng-ARE-Del−/−) F1 mice.
Figure 13B:
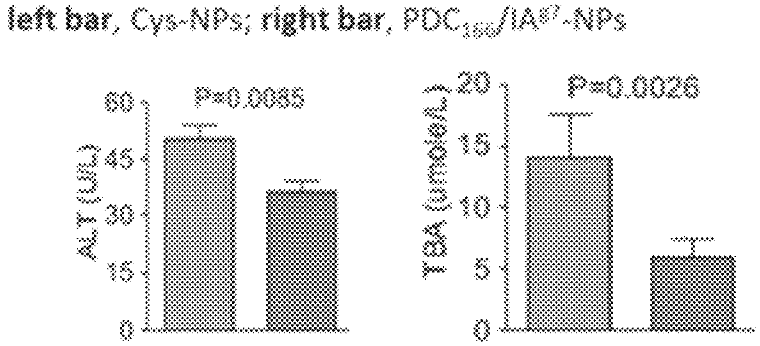
Figure 13C:
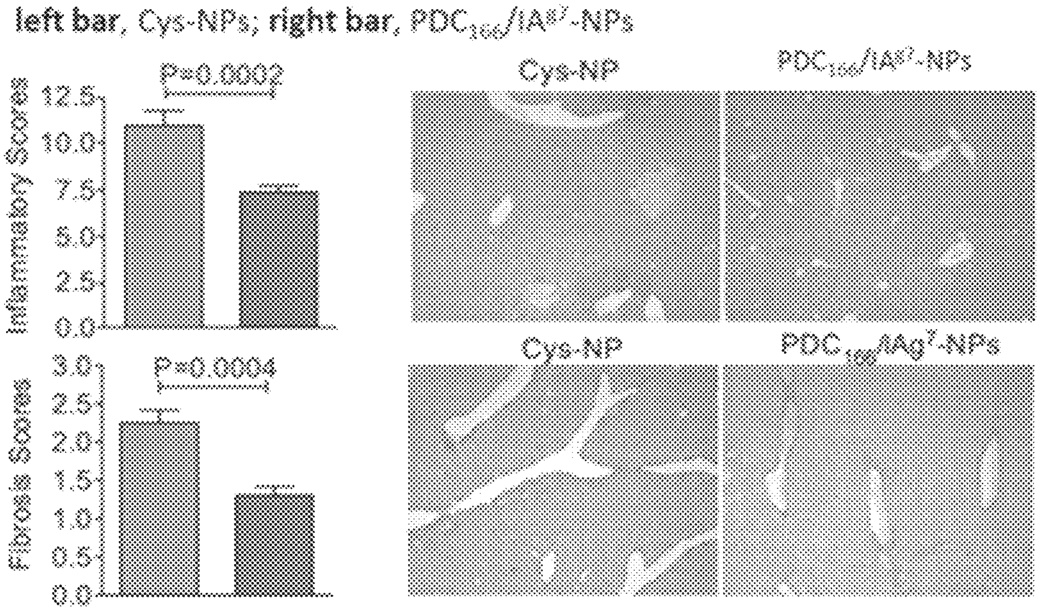

The NOD.c3c4 model does not fully recapitulate the immunopathology of human PBC, characterized by female prevalence, progression to liver fibrosis and absence of liver cyst formation. B6 mice carrying a deletion of the IFNγ 3'-untranslated region adenylate uridylate-rich element (ARE) (ARE-Del+/−) have a dysregulated Ifng locus, and develop a form of PBC that, like the human disease, primarily affects females and is associated with up-regulation of TBA, production of anti-PDC-E2 autoantibodies, portal duct and lobular liver inflammation, bile duct damage, granuloma formation and fibrosis. FIG. 13A-C show that treatment of (NODxB6.ARE-Del−/−) F1 mice with PDC-$E2_{166-181}$/$IA^{g7}$-NPs suppressed the upregulation of TBA and ALT levels, liver inflammation and fibrosis, as compared to mice treated with control NPs.

Example 11—Select Methods Utilized Herein

Mice

NOD/LtJ, BALB/c, C57BL/6, NOD.scid.Il2rg−/−(NSG), NOD.c3c4 and FVB/N.Abcb4−/−(Abcb4 or ATP-binding cassette transporter, sub-family B, member 4) mice were purchased from the Jackson Laboratory (Bar Harbor, ME). IFNγ ARE-Del−/−B6 mice were obtained from H. Young (NIH, Bethesda, MD). NOD.c3c4.scid mice were generated by backcrossing (NOD.c3c4×NOD.scid) F1 mice with NOD.c3c4 mice for five generations, followed by intercrossing of mice heterozygous for the scid mutation and homozygous for the B6 chromosome 3 and 4 intervals from NOD.c3c4 mice. NOD.Abcb4−/− mice were obtained by backcrossing the mutant Abcb4 allele from FVB/N-Abcb4−/− mice onto the NOD/Ltj background for six generations, followed by intercrossing. (NODxB6.IFNγ ARE-Del−/−) F1 mice were generated by intercrossing IFNγ ARE-Del−/− and NOD/LtJ mice. NOD. 1110tm1Flv (Tiger) mice were obtained by backcrossing the 1110tm1Flv allele from C57BL/6.1110tm1Flv mice (Jackson Lab) onto the NOD/Ltj background for 10 generations. RIP-DTR.NOD transgenic mice were generated by backcrossing an X-chromosome-linked rat-insulin promoter-driven human diphtheria toxin receptor (RIP-DTR) transgene from transgenic B6 mice into the NOD background for more than 10 generations.

Cell Lines, Pathogens, and Tumors

CHO-S, BSC-1, MDCK, 293T, B16/F10 and CT26 cell lines were purchased from the ATCC (Manassas, VA). *Listeria monocytogenes* was obtained from DMX Corporation (Philadelphia, PA).

Antibodies and Flow Cytometry

FITC, PE, APC, PerCP or biotin-conjugated mAbs against mouse CD4 (RM4-5), CD5 (53-7.3), CD19 (1D3), B220 (RA36B2) and CD49b (HMa2) and streptavidin-PerCP were purchased from BD Biosciences (San Diego, CA). Anti-murine LAG-3 mAb (C9B7W) was purchased from eBioscience (San Diego, CA). Anti-latent-associated-TGF-β (LAP) antibody (TW7-16B4) was from BioLegend (San Diego, CA). PE-conjugated pMHC class II tetramers were produced using biotinylated pMHC monomers. pMHC class II tetramer staining and phenotypic marker analysis were done essentially as described with minor modifications. Briefly, after avidin incubation (15 min at RT), blood leukocytes, and single cell suspensions from spleen, lymph node, liver mononuclear cells, and bone marrow cells were stained first with pMHC tetramer (5 μg $ml^{-1}$) in FACS buffer (0.05% sodium azide and 1% FBS in PBS) for 60 min at 37° C., and later with FITC-conjugated anti-mouse CD4 (5 μg $ml^{-1}$) and PerCP-conjugated anti-mouse B220 (2 μg $ml^{-1}$; as a 'dump' channel) for 30 min at 4° C. After washing, cells were fixed (1% paraformaldehyde in PBS) and analyzed with FACScan, FACSaria, or BD LSRII flow cytometers. For phenotypic analyses, the cells were incubated with anti-FcR Abs, and then stained with cell surface marker antibodies diluted 1:100 in FACS buffer (at 4° C. for anti-CD49b and anti-LAP Abs, and at 37° C. for anti-LAG-3 Abs) followed by pMHC tetramer, FITC-conjugated anti-mouse CD4 (5 μg $ml^{-1}$) and PerCP-conjugated anti-mouse B220. Upon staining, cells were washed, fixed, and analyzed by flow cytometry. FlowJo software was used for all analyses.

NSG-engrafted human T cells were analyzed using the following mAbs: FITC-conjugated anti-CD4 (OKT4, BioLegend), APC-conjugated anti-CD19 (HIB19, BD Biosciences, San Jose, CA), PerCP-conjugated polyclonal goat anti-LAG-3 IgG (R&D Systems, Minneapolis, MN), biotin-conjugated anti-CD49b (AK7, Pierce Antibodies, Thermo Fisher Scientific, Waltham, MA), and eFluor 450-conjugated streptavidin (eBioscience). Briefly, splenocytes and pancreatic lymph node cells were incubated with avidin (0.25 mg $ml^{-1}$ in FACS buffer) for 30 min at room temperature, washed and stained with tetramer (5 μg $ml^{-1}$) for 1 h at 37° C., washed, and incubated with FITC-conjugated anti-CD4 (2/100), APC-conjugated anti-CD19 (5/100; used as a 'dump' channel), PerCP-conjugated anti-LAG-3 (8/100) and biotin-conjugated anti-CD49b (4/100) at 4° C. for 45 min. After washing, the cells were incubated with eFluor 450-conjugated streptavidin for 30 min at 4° C., washed, fixed in 1% PFA in PBS and cells within the hCD4+/hCD19− gate analysed with a FACSCanto II (BD Bioscience).

pMHC Monomers and Peptides

Recombinant pMHC class II monomers were purified from supernatants of CHO-S cells transduced with lentiviruses encoding a monocistronic message in which the peptide-MHCb and MHCa chains of the complex were separated by the ribosome skipping P2A sequence. The peptide was tethered to the amino terminal end of the MHCb chain via a flexible GS linker and the MHCa chains were engineered encode a BirA site, a 6×His tag, a twin strep-tag and a free Cys at their carboxyterminal end. The secreted, self-assembled pMHC class II complexes were purified by sequential nickel and Strep-Tactin® chromatography and used for coating onto NPs or processed for biotinylation and tetramer formation as described above. The epitopes encoded in the murine monomeric constructs were selected based on predicted MHCII-binding capacity using RANKPEP (imed.med.ucm.es) using 7.54 as the threshold score. PDC-$E2_{166-181}$ had a score that fell below the threshold but was selected for experimentation because it is contained within one of the lipoyl-binding domains of PDC-E2, an antigenic target for AMAs. For CYPD and FTCD epitope prediction, we used a second online algorithm (GPS-MBA) (mba.biocuckoo.org) and peptides predicted by both RANKPEP and GPS-MBA were selected for experimentation. hPDC-$E2_{122-135}$, hPDC-E2249-262 (both contained within the lipoyl-binding domain of PDC-E2), and hPDC-$E2_{629-643}$ have been described previously. The sequences of the different epitopes are: PDC-$E2_{166-181}$/$IA^{g7}$ (LAEIETDKATIGFEVQ, SEQ ID NO: 106), PDC-$E2_{82-96}$/$IA^{g7}$ (EKPQDIEAFKNYTLD, SEQ ID NO: 107), $FTCD_{58-72}$/$IA^{g7}$ (VVEGALHAARTASQL, SEQ ID NO: 108), $CYPD_{398-412}$/$IA^{g7}$ (LITNLSSALKDETVW, SEQ ID NO: 109), 2.5 mi/$IA^{g7}$ (AHHPIWARMDA, SEQ ID NO: 110), hPDC-E2122-135/DRB4*0101 (GDLIAEVETDKATV, SEQ ID NO: 8), hPDC-E2249-262/DRB4*0101 (GDLLAEIETDKATI, SEQ ID NO: 9), and hPDC-E2629-643/DRB1*0801 (AQWLAEFRKYLEKPI, SEQ ID NO: 7). Synthetic PDC-$E2_{166-181}$, 2.5 mi, and $mMOG_{36-55}$ (EVGWYRSPESRVVHLYRNGK, SEQ ID NO: 111) peptides were purchased from Genscript (Piscataway, NJ). The amino acid residue numbers for each peptide correspond to those found in the mature form of the corresponding antigens.

Nanoparticles, pMHCII-NP Synthesis, and Purification pMHCs were coated onto pegylated iron oxide NPs (PFM-NPs), produced as described (2). Briefly, PFM-NPs were produced by thermal decomposition of Fe (acac); in the presence of 2 kD methoxy-PEG-maleimide. The NPs were purified using magnetic (MACS) columns (Miltenyi Biotec, Auburn, CA). Free Cysteines (controls) or pMHCs, carrying a free carboxyterminal Cys, were conjugated to the maleimide-functionalized PFMs in 40 mM phosphate buffer, pH 6.0, containing 2 mM EDTA, 150 mM NaCl overnight at room temperature. The pMHC-conjugated NPs were separated from free pMHC using magnetic columns, sterilized by filtration through 0.2 μm filters and stored in water or PBS at 4° C. Quality control was done using transmission electron microscopy, dynamic light scattering, and native and denaturing gel electrophoresis. pMHC content was measured using Bradford assay (Thermo Fisher Scientific) and SDS-PAGE.

Ursodeoxycholic Acid Treatment

Cohorts of 5-6 or 24 wk-old male and/or female NOD.c3c4 mice were left untreated, fed a diet supplemented with 0.5% UDCA (BOC Sciences, Upton, NY; TestDiet, Richmond, IN), or treated with pMHCII-NPs for 14 or 9 wk, respectively, and sacrificed for pMHCII tetramer staining, PBC scoring and biochemical testing.

pMHCII-NP Therapy in NOD.c3c4, (NOD×B6.IFNγ ARE-Del−/−) F1 and NOD/Ltj Mice

Cohorts of 15 wk-old male and/or female NOD.c3c4 mice with established PBC were left untreated or treated with 20 mg of pMHCII-NPs or Cys-NPs (i.v.) twice weekly for 9 wk unless indicated otherwise. Liver disease scoring involved macroscopic evaluation of cyst content (0-5), liver weight and CBD diameter (0-4), as well as microscopic evaluation of bile duct involvement (0-4), bile duct proliferation (0-4) and mononuclear cell infiltration (0-4), essentially as described (23). In other experiments, treatment was initiated at the peak of disease (24 wk of age) and given twice a week for 14-20 wk. Intermittent treatment involved treating mice twice a wk from 15 to 24 wk of age, then withdrawing treatment until the percentages of tetramer+ cells dropped to ~50% of the levels seen at treatment withdrawal (measurements in peripheral blood were done once every two wk), re-treating mice twice a wk until the percentages of tetramer+ cells reached original values, and repeating this cycle until 50 wk of age.

In in vivo cytokine blocking experiments, mAbs against HRPN (rIgG1), IL-10 (JES5-2A5) or TGF-β (1D11) (BioXcell, West Lebanon, NH) were given i.p. twice a week at 500 mg per dose for 2 wk, followed by 200 mg per dose for 7 additional wk. Mice were randomized into cytokine-neutralizing mAb-treatment (anti-IL-10 or -TGFβ) or HRPN rat-IgG1 groups.

In experiments involving (NOD×B6.IFNγ ARE-Del−/−) F1 mice, 10-wk-old male and female mice were treated for 5-6 wk. Histopathologic scoring in the liver was performed as described. Briefly, severity scores were obtained by scoring portal inflammation, lobular inflammation and granuloma formation from 0-4, and bile duct damage from 0-2. The extent of portal inflammation and bile duct damage were scored from 0-4 based on the ratio between affected vs unaffected area. The extent of lobular inflammation and granuloma formation were scored from 0-4 based on number of lesions per specimen. The severity of fibrosis was scored on a 0-6 scale.

Studies using NOD mice involved treating cohorts of 10-wk-old pre-diabetic female NOD/Ltj mice with 20 mg of pMHCII-NPs or Cys-NPs i.v. twice weekly for 5 wk.

pMHCII-NP Therapy for AIH in NOD Mice

AIH was induced by infecting 5-6 wk-old female NOD/Ltj mice with an adenovirus encoding human FTCD (Ad-hFTCD, 1010 plaque forming units (PFU) i.v.). Four wks later, cohorts of mice with established AIH were treated with 20 mg of pMHCII-NP s or Cys-NPs (i.v.) twice weekly for 5-6 wk. Histopathological scoring was done using the Ishak scale as above.

pMHCII-NP Therapy in Human PBMC-Reconstituted NSG Hosts

PBMCs from HLA-DRB4*0101+ PBC patients (recruited under informed consent approved by the Institutional Review Board at Hospital Clinic) were depleted of CD8+ T-cells using anti-CD8 mAb-coated magnetic beads (Miltenyi Biotech, Auburn, CA) and injected i.v. ($2\times10^7$) into 8-10 wk-old NSG hosts. Mice were treated with 30-40 mg pMHC-NPs starting on day 5 after PBMC transfusion, twice a wk for 5 consecutive wks, or left untreated. Therapy-induced expansion of cognate CD4+ T-cells was measured in liver, peripheral LNs, spleen and bone marrow (not shown). A mouse was considered a responder if the percentage of tetramer+ T-cells in at least two different organs were higher than the mean±10 standard deviation values seen in untreated hosts.

Cytokine Secretion Assays

Splenic and portal/celiac lymph node (PCLN) cell suspensions from pMHCII-NP-treated mice were enriched for CD4+ T-cells depleting CD19+ B-cells (EasySep™ Mouse CD19 Positive Selection Kit, Stem Cell Technologies, Vancouver, BC) and CD8+ T-cells (CD8 Magnetic Particles, BD Biosciences). Cells were stained with pMHCII tetramers and sorted by flow cytometry. The sorted cells ($2\text{-}3\times10^4$) were challenged with bone marrow-derived DCs ($2\times10^4$) pulsed with 2 μg $ml^{-1}$ peptide. Forty-eight hours later, supernatants were harvested for measurement of cytokine content via Luminex®.

To ascertain whether pMHCII-NP therapy promoted the recruitment/formation of Il-10-secreting B-cells, mesenteric LNs, PCLNs and liver cell suspensions were enriched for B-cells using a CD19 enrichment kit (Stem Cell Technologies). The cells (2-3×105 in 200 mL/well) were stimulated in duplicate with LPS (1 μg $ml^{-1}$, Sigma) for 24 h in RPMI-1640) media containing 10% FCS. The levels of IL-10 in the supernatants were measured via Luminex®.

Isolation and In Vitro Stimulation of Lymph Node CD11b+ Cells and Liver Kupffer Cells CD11b+ cells from LNs were obtained by digestion in collagenase D (1.25 μg $ml^{-1}$) and DNAse I (0.1 μg $mL^{-1}$) for 15 min at 37° C., washed, incubated with anti-FER Abs, and purified using anti-CD11b mAb-coated magnetic beads (BD Biosciences). The purified cells (2-3×105 in 200 mL/well) were stimulated with LPS (2 μg $ml^{-1}$) for 3 days, and the supernatants analyzed for cytokine content using a Luminex®) multiplex cytokine assay.

To isolate Kupffer cells (KCs), livers from treated and untreated mice were minced and digested in 15 ml of 0.05% collagenase solution in HBSS for 20-30 min at 37° C. The resulting cell suspension was filtered through a nylon mesh (0.7 μm) and centrifuged at 50×g for 3 min at 4° C., to remove tissue debris and hepatocytes. Cells in the supernatant were pelleted by centrifugation at 300×g for 5 min at 4° C. The cell pellet, mainly composed of non-parenchymal liver immune cells, KCs, sinusoidal endothelial cells and stellate cells, was re-suspended in 33% Percoll® solution and centrifuged at 350×g for 30 min to isolate mononuclear cells. The pellets were re-suspended in DMEM containing 10% FCS ($5\times10^6$ cells $ml^{-1}$) and plated in 6-well plate at $1\text{-}3\times10^7$ cells/well and incubated for 2-3 h in a 5% $CO_2$ atmosphere at 37° C. Non-adherent cells were removed by gentle washing with PBS. The adherent fraction (enriched for KCs) was harvested by trypsin digestion (5 min, 0.25% trypsin). The resulting cell suspension was plated in 96 well plates at 1-2×105/200 mL/well and stimulated with LPS (2 mg $ml^{-1}$) for 3d. The supernatants were analyzed for cytokine content using a Luminex® multiplex cytokine assay.

Adoptive Transfer of Suppression

Splenic CD4+ T-cells (107) from untreated mice or mice treated with 12 doses of PDC-$E2_{166\text{-}181}$/$IA^{g7}$-NPs were adoptively transferred (i.v.) into 10-14 wk-old, sex-matched NOD.c3c4.scid hosts. One day later, the recipients were adoptively transferred with 4×107 whole splenocytes from sex-matched NOD.c3c4 donor mice with established PBC (>35 wk-old). One of the cohorts of mice transfused with CD4+ T-cells from pMHCII-NP-treated donors was further treated with 12 doses of PDC-$E2_{166\text{-}181}$/$IA^{g7}$-NPs. The recipients were sacrificed 6 wk later for tetramer staining and PBC scoring.

In Vivo Breg Induction Assay

Splenic B-cells from NOD.$1110^{m1Flv}$ (Tiger) mice were enriched using an EasySep Mouse B-cell Isolation Kit (Stem Cell Technologies) and pulsed with BDC2.5 mi or $PDC_{166\text{-}181}$ peptides (10 μg $ml^{-1}$) for 2 h at 37° C. The peptide-pulsed B-cells were washed twice with PBS, labeled with PKH26 (Sigma) and transfused (3×106) into pMHC-NP-treated or untreated mice. The hosts were killed 7d later and their spleens, MLNs, PCLNs and liver mononuclear cells were labeled with anti-B220-APC and biotinylated anti-CD1d or anti-CD5 mAbs followed by Streptavidin-PerCP. PKH26+ B-cells were analyzed for presence of eGFP+/CD1 dhigh and eGFP+/CD5+ cells by flow cytometry.

Histology and Immunohistochemistry

Livers were fixed in 10% formalin for 2d, embedded in paraffin, cut into 5 μm sections and stained with H&E or Picrosirius Red. For immunohistochemistry, liver tissues were embedded in Tissue-Tek OCT, sectioned into 30 μm cryosections and stored on slides at −80° C. Slides were fixed in chilled acetone, washed with PBS, treated with a 1:10 dilution of 30% $H_2O_2$ in PBS, washed with PBS, blocked with 10% normal goat serum in PBS, washed again, and stained with anti-mouse CD4 (GK1.5) or CD8 (Lyt-2) antibodies (1.5 h, 4° C.). After washing, the slides were stained with a biotinylated goat anti-rat secondary antibody (1:200 dilution), incubated with Horseradish Peroxidase (HRP)-conjugated streptavidin, followed by 3,3-diaminobenzidine (DAB) substrate. Slides were counterstained with hematoxylin before mounting.

ALT and TBA Assays

Alanine aminotransferase (ALT) levels in serum were determined using a kit from Thermo Fisher Scientific following the manufacturer's protocol. Briefly, serum samples were mixed with pre-warmed (37° C.') Infinity™ ALT (GPT) Liquid Stable Reagent at 1:10 ratio and OD readings were taken for 3 min at lmin intervals in a nanodrop at a 340 nm wavelength, 37° C. The slope was calculated by plotting absorbance vs. time using linear regression and multiplied with a factor to obtain ALT levels in serum (U/L) as described in the kit. Serum total bile acid (TBA) levels were analyzed using a TBA Enzymatic Cycling Assay Kit (Diazyme, Poway, CA) following a modified manufacturer's protocol as described.

Anti-Nuclear and Anti-Mitochondrial Autoantibody Measurements

Presence of anti-nuclear autoantibodies (ANAs) in serum was ascertained using NOVA Lite® HEp-2 Slides kit (Inova Diagnostics, San Diego, CA). A semi-quantitative approach was followed to measure ANA titers. Briefly, serum samples were serially diluted in PBS (at 1:160, 1:320, 1:640, 1:1280 and 1:2560) and then added to pre-fixed Hep-2 substrate slides, washed, stained with FITC-conjugated goat anti-mouse IgG in PBS containing 5% normal donkey serum (1:200 dilution), washed, mounted and read under a fluorescent microscope.

Serum levels of anti-mitochondrial PDC-E2 antibodies were determined via ELISA. Briefly, ELISA plates were coated with PDC-E2 protein (5 μg $ml^{-1}$, 100 mL) (SurModics Inc., Eden Prairie, MN) overnight at RT. Plates were washed, blocked using 3% dry skim milk in PBS (pH 7.4, 150 ml), and incubated with serially-diluted serum samples (100 ml, at 1:250) dilutions prepared using reagent diluent) for 2 h at RT. Wells were washed and incubated with 100 mL of HRP-conjugated anti-mouse IgG (1:2000 in reagent diluent) for 2 h at RT, and washed. Finally, wells were incubated in the dark with 100 ml of DAB substrate for 20 min at RT. Upon stopping the enzymatic reaction with 50 ml. 2N $H_2SO_4$, the absorption was measured at a 450 nm wavelength using an ELISA plate reader. The Positive Antibody Activity (PAA) levels were calculated by calculating the mean OD+2 SD of the control NOD serum samples (positive index) and by dividing the OD values corresponding to NOD.c3c4 serum samples by the positive index, whereby values >1.0 correspond to PAA.

Statistical Analyses

Unless specified, sample size values mentioned in the figure legends correspond to the total number of mice examined, pooled from different experiments. Data were compared in GraphPad Prism 6 using Mann-Whitney U-test, Chi-Square, Log-Rank (Mantel-Cox), Pearson correlation, two-way ANOVA or multiple t test analyses using the Holm-Sidak correction. P values <0.05 were considered statistically significant. Only statistically significant P values are displayed on Figures.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

TABLE 5

Additional Ubiquitous Autoantigens

| Cellular location | Uniprot Code | | Description |
|---|---|---|---|
| Cytoplasm | P14152 | Mdh1 | Malate dehydrogenase, cytoplasmic (EC 1.1.1.37) (Cytosolic malate dehydrogenase) |
| Cytoplasm | P63260 | Actg1 | Actin, cytoplasmic 2 (Gamma-actin) [Cleaved into: Actin, cytoplasmic 2, N-terminally processed] |
| Cytoplasm | P20152 | Vim | Vimentin |
| Cytoplasm | P06151 | Ldha | L-lactate dehydrogenase A chain (LDH-A) (EC 1.1.1.27) (LDH muscle subunit) (LDH-M) |
| Cytoplasm | P16858 | Gapdh | Glyceraldehyde-3-phosphate dehydrogenase (GAPDH) (EC 1.2.1.12) (Peptidyl-cysteine S-nitrosylase GAPDH) (EC 2.6.99.—) |
| Cytoplasm | P63101 | Ywhaz | 14-3-3 protein zeta/delta (Protein kinase C inhibitor protein 1) (KCIP-1) (SEZ-2) |
| Cytoplasm | P11404 | Fabp3 | Fatty acid-binding protein, heart (Fatty acid-binding protein 3) (Heart-type fatty acid-binding protein) (H-FABP) (Mammary-derived growth inhibitor) (MDGI) |
| Cytoplasm | O08997 | Atox1 | Copper transport protein ATOX1 (Metal transport protein ATX1) |
| Cytoplasm | P35700 | Prdx1 | Peroxiredoxin-1 (EC 1.11.1.15) (Macrophage 23 kDa stress protein) (Osteoblast-specific factor 3) (OSF-3) (Thioredoxin peroxidase 2) (Thioredoxin-dependent peroxide reductase 2) |
| Cytoplasm | Q9CQM5 | Txndc17 | Thioredoxin domain-containing protein 17 (14 kDa thioredoxin-related protein) (TRP14) (Protein 42-9-9) (Thioredoxin-like protein 5) |
| Nucleus | P09405 | Ncl | Nucleolin (Protein C23) |
| Nucleus | Q9Z2X1 | Hnrnpf | Heterogeneous nuclear ribonucleoprotein F (hnRNP F) [Cleaved into: Heterogeneous nuclear ribonucleoprotein F, N-terminally processed] |
| Nucleus | Q3U898 | Cops9 | COP9 signalosome complex subunit 9 |

TABLE 5-continued

| Additional Ubiquitous Autoantigens | | | |
|---|---|---|---|
| Cellular location | Uniprot Code | | Description |
| Nucleus | P62322 | Lsm5 | U6 snRNA-associated Sm-like protein LSm5 |
| Nucleus | P17918 | Pcna | Proliferating cell nuclear antigen (PCNA) (Cyclin) |
| Nucleus | O88569 | Hnrnpa2b1 | Heterogeneous nuclear ribonucleoproteins A2/B1 (hnRNP A2/B1) |
| Nucleus | P40142 | Tkt | Transketolase (TK) (EC 2.2.1.1) (P68) |
| Nucleus | Q60972 | Rbbp4 | Histone-binding protein RBBP4 (Chromatin assembly factor 1 subunit C) (CAF-1 subunit C) (Chromatin assembly factor I p48 subunit) (CAF-I 48 kDa subunit) (CAF-I p48) (Nucleosome-remodeling factor subunit RBAP48) (Retinoblastoma-binding protein 4) (RBBP-4) (Retinoblastoma-binding protein p48) |
| Nucleus | Q60973 | Rbbp7 | Histone-binding protein RBBP7 (Histone acetyltransferase type B subunit 2) (Nucleosome-remodeling factor subunit RBAP46) (Retinoblastoma-binding protein 7) (RBBP-7) (Retinoblastoma-binding protein p46) |
| Nucleus | P15532 | Nme1 | Nucleoside diphosphate kinase A (NDK A) (NDP kinase A) (EC 2.7.4.6) (Metastasis inhibition factor NM23) (NDPK-A) (Tumor metastatic process-associated protein) (nm23-M1) |
| Plasma Membrane | More Abundant | | |
| Plasma Membrane | P68040 | Rack1 | Receptor of activated protein C kinase 1 (12-3) (Guanine nucleotide-binding protein subunit beta-2-like 1) (Receptor for activated C kinase) (Receptor of activated protein kinase C 1) (p205) [Cleaved into: Receptor of activated protein C kinase 1, N-terminally processed (Guanine nucleotide-binding protein subunit beta-2-like 1, N-terminally processed)] |
| Plasma Membrane | Q62351 | Tfrc | Transferrin receptor protein 1 (TR) (TfR) (TfR1) (Trfr) (CD antigen CD71) |
| Plasma Membrane | Q9QYY0 | Gab1 | GRB2-associated-binding protein 1 (GRB2-associated binder 1) (Growth factor receptor bound protein 2-associated protein 1) |
| Plasma Membrane | P42703 | Lifr | Leukemia inhibitory factor receptor (LIF receptor) (LIF-R) (D-factor/LIF receptor) (CD antigen CD118) |
| Plasma Membrane | Q01279 | Egfr | Epidermal growth factor receptor (EC 2.7.10.1) |
| Plasma Membrane | Q62351 | Tfrc | Transferrin receptor protein 1 (TR) (TfR) (TfR1) (Trfr) (CD antigen CD71) |
| Plasma Membrane | P14069 | S100a6 | Protein S100-A6 (5B10) (Calcyclin) (Prolactin receptor-associated protein) (S100 calcium-binding protein A6) |
| Plasma Membrane | Q61160 | Fadd | FAS-associated death domain protein (FAS-associating death domain-containing protein) (Mediator of receptor induced toxicity) (Protein FADD) |
| Plasma Membrane | Q5M8N0 | Cnrip1 | CB1 cannabinoid receptor-interacting protein 1 (CRIP-1) |
| Plasma Membrane | Q60902 | Eps1511 | Epidermal growth factor receptor substrate 15-like 1 (Epidermal growth factor receptor pathway substrate 15-related sequence) (Eps15-rs) (Eps15-related protein) (Eps15R) |

TABLE 5-continued

| Additional Ubiquitous Autoantigens | | | |
|---|---|---|---|
| Cellular location | Uniprot Code | | Description |
| Plasma Membrane | P97300 | Nptp | Nuroplastin |
| Mitochondria | Q64433 | Hspe1 | 10 kDa heat shock protein, mitochondrial (Hsp10) (10 kDa chaperonin) (Chaperonin 10) (CPN10) |
| Mitochondria | Q07813 | Bax | Apoptosis regulator BAX |
| Mitochondria | P38647 | Hspa9 | Stress-70 protein, mitochondrial (75 kDa glucose-regulated protein) (GRP-75) (Heat shock 70 kDa protein 9) (Mortalin) (Peptide-binding protein 74) (PBP74) (p66 MOT) |
| Mitochondria | P19157 | Gstp1 | Glutathione S-transferase P 1 (Gst P1) (EC 2.5.1.18) (GST YF-YF) (GST class-pi) (GST-piB) (Preadipocyte growth factor) |
| Mitochondria | Q9CR21 | Ndufab1 | Acyl carrier protein, mitochondrial (ACP) (CI-SDAP) (NADH-ubiquinone oxidoreductase 9.6 kDa subunit) |
| Mitochondria | P08249 | Mdh2 | Malate dehydrogenase, mitochondrial (EC 1.1.1.37) |
| Mitochondria | P63038 | Hspd1 | 60 kDa heat shock protein, mitochondrial (EC 3.6.4.9) (60 kDa chaperonin) (Chaperonin 60) (CPN60) (HSP-65) (Heat shock protein 60) (HSP-60) (Hsp60) (Mitochondrial matrix protein P1) |
| Mitochondria | Q03265 | Atp5f1a | ATP synthase subunit alpha, mitochondrial (ATP synthase F1 subunit alpha) |
| Mitochondria | P63038 | Hspd1 | 60 kDa heat shock protein, mitochondrial (EC 3.6.4.9) (60 kDa chaperonin) (Chaperonin 60) (CPN60) (HSP-65) (Heat shock protein 60) (HSP-60) (Hsp60) (Mitochondrial matrix protein P1) |
| Mitochondria | P56382 | Atp5f1e | ATP synthase subunit epsilon, mitochondrial (ATPase subunit epsilon) (ATP synthase F1 subunit epsilon) |
| Golgi | More Abundant | | |
| Golgi | P61205 | Arf3 | ADP-ribosylation factor 3 |
| Golgi | P61750 | Arf4 | ADP-ribosylation factor 4 |
| Golgi | P84084 | Arf5 | ADP-ribosylation factor 5 |
| Golgi | Q99LT0 | Dpy30 | Protein dpy-30 homolog (Dpy-30-like protein) (Dpy-30L) |
| Golgi | P53811 | Pitpnb | Phosphatidylinositol transfer protein beta isoform (PI-TP-beta) (PtdIns transfer protein beta) (PtdInsTP beta) |
| Golgi | O35643 | Ap1b1 | AP-1 complex subunit beta-1 (Adaptor protein complex AP-1 subunit beta-1) (Adaptor-related protein complex 1 subunit beta-1) (Beta-1-adaptin) (Beta-adaptin 1) (Clathrin assembly protein complex 1 beta large chain) (Golgi adaptor HA1/AP1 adaptin beta subunit) |
| Golgi | P61211 | Arl1 | ADP-ribosylation factor-like protein 1 |
| Golgi | Q3UPH1 | Prrc1 | Protein PRRC1 (Proline-rich and coiled-coil-containing protein 1) |
| Golgi | P61924 | Copz1 | Coatomer subunit zeta-1 (Zeta-1-coat protein) (Zeta-1 COP) |
| Golgi | Q9CQC9 | Sar1b | GTP-binding protein SAR1b |
| ER | O55022 | Pgrmc1 | Membrane-associated progesterone receptor component 1 (mPR) |
| ER | P33267 | Cyp2f2 | Cytochrome P450 2F2 (EC 1.14.14.—) (CYPIIF2) (Cytochrome P450-NAH-2) (Naphthalene dehydrogenase) (Naphthalene hydroxylase) |
| ER | O55143 | Atp2a2 | Sarcoplasmic/endoplasmic reticulum calcium ATPase 2 (SERCA2) (SR Ca(2+)-ATPase 2) (EC 3.6.3.8) (Calcium pump 2) (Calcium-transporting ATPase sarcoplasmic reticulum type, slow twitch skeletal muscle isoform) (Endoplasmic reticulum class 1/2 Ca(2+) ATPase) |
| ER | P45878 | Fkbp2 | Peptidyl-prolyl cis-trans isomerase FKBP2 (PPIase FKBP2) (EC 5.2.1.8) (13 kDa FK506-binding protein) (13 kDa FKBP) (FKBP-13) (FK506-binding protein 2) (FKBP-2) (Immunophilin FKBP13) (Rotamase) |

TABLE 5-continued

| Additional Ubiquitous Autoantigens | | | |
|---|---|---|---|
| Cellular location | Uniprot Code | | Description |
| ER | P56395 | Cyb5a | Cytochrome b5 |
| ER | Q9D1Q6 | Erp44 | Endoplasmic reticulum resident protein 44 (ER protein 44) (ERp44) (Thioredoxin domain-containing protein 4) |
| ER | P35564 | Canx | Calnexin |
| ER | P08113 | Hsp90b1 | Endoplasmin (94 kDa glucose-regulated protein) (GRP-94) (Endoplasmic reticulum resident protein 99) (ERp99) (Heat shock protein 90 kDa beta member 1) (Polymorphic tumor rejection antigen 1) (Tumor rejection antigen gp96) |
| ER | Q01853 | Vcp | Transitional endoplasmic reticulum ATPase (TER ATPase) (EC 3.6.4.6) (15S Mg(2+)-ATPase p97 subunit) (Valosin-containing protein) (VCP) |
| | Q9D0F3 | Lman1 | Protein ERGIC-53 (ER-Golgi intermediate compartment 53 kDa protein) (Lectin mannose-binding 1) (p58) |

Also contemplated are the human proteins or human homologues disclosed in this table

TABLE 6

| Sequences Disclosed | | | | |
|---|---|---|---|---|
| HLA Allele bound | Position in protein start | end | Amino Acid Sequence PDC-E2 derived peptides | SEQ ID NO: |
| DRB3*0202 | 353 | 367 | GRVFVSPLAKKLAVE | 1 |
| DRB3*0202 | 72 | 86 | RLLLQLLGSPGRRYY | 2 |
| DRB3*0202 | 422 | 436 | DIPISNIRRVIAQRL | 3 |
| DRB5*0101 | 353 | 367 | GRVFVSPLAKKLAVE | 4 |
| DRB5*0101 | 80 | 94 | SPGRRYYSLPPHQKV | 5 |
| DRB5*0101 | 535 | 549 | ETIANDVVSLATKAR | 6 |
| DRB4*0101 | 629 | 643 | AQWLAEFRKYLEKPI | 7 |
| DRB4*0101 | 122 | 135 | GDLIAEVETDKATV | 8 |
| DRB4*0101 | 249 | 262 | GDLLAEIETDKATI | 9 |
| DRB1*0801 | 249 | 263 | GDLLAEIETDKATIG | 10 |
| DRB3*0202 | 422 | 436 | DIPISNIRRVIAQRL | 11 |
| DRB5*0101 | 80 | 94 | SPGRRYYSLPPHQKV | 12 |
| CYP2D6 derived peptides | | | | |
| DRB3*01:01 | 284 | 298 | GNPESSFNDENLRIV | 13 |
| DRB3*01:01 | 289 | 303 | SFNDENLRIVVADLF | 14 |
| DRB3*01:01 | 318 | 332 | LLLMILHPDVQRRVQ | 15 |
| DRB1*03:01 | 313 | 332 | TLAWGLLLMILHPDV QRRVQ | 16 |
| DRB1*03:01 | 393 | 412 | TTLITNLSSVLKDEA VWEKP | 17 |
| DRB1*03:01 | 192 | 206 | GRRFEYDDPRFLRLL | 18 |

TABLE 6-continued

| Sequences Disclosed | | | | |
|---|---|---|---|---|
| HLA Allele bound | Position in protein start | end | Amino Acid Sequence PDC-E2 derived peptides | SEQ ID NO: |
| DRB1*03:01 | 5 | 19 | ALVPLAVIVAIFLLL | 19 |
| DRB1*03:01 | 293 | 307 | ENLRIVVADLFSAGM | 20 |
| DRB3*0202 | 219 | 233 | FLREVLNAVPVLLHI | 21 |
| DRB3*0202 | 237 | 251 | AGKVLRFQKAFLTQL | 22 |
| DRB3*0202 | 15 | 29 | IFLLLVDLMHRRQRW | 23 |
| DRB4*0101 | 235 | 249 | ALAGKVLRFQKAFLT | 24 |
| DRB4*0101 | 317 | 331 | GLLLMILHPDVQRRV | 25 |
| DRB4*0101 | 293 | 307 | ENLRIVVADLFSAGM | 26 |
| DRB5*0101 | 428 | 442 | VKPEAFLPFSAGRRA | 27 |
| DRB5*0101 | 237 | 251 | AGKVLRFQKAFLTQL | 28 |
| DRB5*0101 | 14 | 28 | AIFLLLVDLMHRRQR | 29 |
| DRB1*04:01 | 199 | 213 | DPRFLRLLDLAQEGL | 30 |
| DRB1*04:01 | 450 | 464 | RMELFLFFTSLLQHF | 31 |
| DRB1*04:01 | 301 | 315 | DLFSAGMVTTSTTLA | 32 |
| DRB1*07:01 | 452 | 466 | ELFLFFTSLLQHFSF | 33 |
| DRB1*07:01 | 59 | 73 | DQLRRRFGDVFSLQL | 34 |
| DRB1*07:01 | 130 | 144 | EQRRFSVSTLRNLGL | 35 |
| DRB1*07:01 | 193 | 212 | RRFEYDDPRFLRLLD LAQEG | 36 |
| DRB1*07:01 | 305 | 324 | AGMVTTSTTLAWGLL LMILH | 37 |

TABLE 6-continued

Sequences Disclosed

| HLA Allele bound | Position in protein start | Position in protein end | Amino Acid Sequence PDC-E2 derived peptides | SEQ ID NO: |
|---|---|---|---|---|
| ACTB derived peptides | | | | |
| DRB1*0301 | 202 | 216 | TTAEREIVRDIKEKL | 38 |
| DRB1*0301 | 170 | 184 | ALPHAILRLDLAGRD | 39 |
| DRB1*0301 | 245 | 259 | SGRTTGIVMDSGDGV | 40 |
| DRB3*02:02 | 187 | 201 | DYLMKILTERGYSFT | 41 |
| DRB3*02:02 | 172 | 186 | PHAILRLDLAGRDLT | 42 |
| DRB3*02:02 | 131 | 145 | AMYVAIQAVLSLYAS | 43 |
| DRB4*0101 | 131 | 145 | AMYVAIQAVLSLYAS | 44 |
| DRB4*0101 | 171 | 185 | LPHAILRLDLAGRDL | 45 |
| DRB4*0101 | 129 | 143 | TPAMYVAIQAVLSLY | 46 |
| DRB5*0101 | 164 | 178 | PIYEGYALPHAILRL | 47 |
| DRB5*0101 | 25 | 39 | DAPRAVFPSIVGRPR | 48 |
| DRB5*0101 | 323 | 337 | STMKIKIIAPPERKY | 49 |
| DRB3*0101 | 146 | 160 | GRTTGIVMDSGDGVT | 50 |
| DRB3*0101 | 18 | 32 | KAGFAGDDAPRAVFP | 51 |
| DRB4*0101 | 171 | 185 | LPHAILRLDLAGRDL | 52 |
| SLA derived peptides | | | | |
| DRB1*0301 | 334 | 348 | YKKLLKERKEMFSYL | 53 |
| DRB1*0301 | 196 | 210 | DELRTDLKAVEAKVQ | 54 |
| DRB1*0301 | 115 | 129 | NKITNSLVLDIIKLA | 55 |
| DRB1*0301 | 373 | 386 | NRLDRCLKAVRKER | 56 |
| DRB1*0301 | 186 | 197 | LIQQGARVGRID | 57 |
| DRB3*0202 | 342 | 356 | KEMFSYLSNQIKKLS | 58 |
| DRB3*0202 | 110 | 124 | GSSLLNKITNSLVLD | 59 |
| DRB3*0202 | 299 | 313 | NDSFIQEISKMYPGR | 60 |
| DRB4*0101 | 49 | 63 | STLELFLHELAIMDS | 61 |
| DRB4*0101 | 260 | 274 | SKCMHLIQQGARVGR | 62 |
| DRB4*0101 | 119 | 133 | NSLVLDIIKLAGVHT | 63 |
| DRB5*0101 | 86 | 100 | RRHYRFIHGIGRSGD | 64 |
| DRB5*0101 | 26 | 40 | RSHEHLIRLLLEKGK | 65 |
| DRB5*0101 | 331 | 345 | SNGYKKLLKERKEMF | 66 |
| DRB1*0401 | 317 | 331 | SPSLDVLITLLSLGS | 67 |
| DRB1*0401 | 171 | 185 | DQKSCFKSMITAGFE | 68 |
| DRB1*0401 | 417 | 431 | YTFRGFMSHTNNYPC | 69 |
| DRB1*0701 | 359 | 373 | YNERLLHTPHNPISL | 70 |
| DRB1*0701 | 215 | 229 | DCILCIHSTTSCFAP | 71 |
| DRB1*0701 | 111 | 125 | SSLLNKITNSLVLDI | 72 |
| FTCD derived peptides | | | | |
| DRB3*0202 | 439 | 453 | ALQEGLRRAVSVPLT | 73 |
| DRB3*0202 | 381 | 395 | RRQFQSLDTTMRRLI | 74 |
| DRB3*0202 | 297 | 311 | EQRIRLVVSRLGLDS | 75 |
| DRB1*0301 | 525 | 539 | AKTQAALVLDCLETR | 76 |
| DRB1*0301 | 218 | 232 | KVQGIGWYLDEKNLA | 77 |
| DRB1*0301 | 495 | 509 | YFNVLINLRDITDEA | 78 |
| DRB4*0101 | 262 | 276 | LPVVGSQLVGLVPLK | 79 |
| DRB4*0101 | 300 | 314 | IRLVVSRLGLDSLCP | 80 |
| DRB4*0101 | 259 | 273 | ELSLPVVGSQLVGLV | 81 |
| DRB5*0101 | 490 | 504 | GVFGAYFNVLINLRD | 82 |
| DRB5*0101 | 389 | 403 | TTMRRLIPPFREASA | 83 |
| DRB5*0101 | 295 | 309 | EEEQRIRLVVSRLGL | 84 |
| DRB3*0101 | 271 | 285 | GLVPLKALLDAAAFY | 85 |
| DRB3*0101 | 498 | 512 | VLINLRDITDEAFKD | 86 |
| DRB3*0101 | 301 | 315 | RLVVSRLGLDSLCPF | 87 |
| MPO derived peptides | | | | |
| DRB3*0202 | 322 | 336 | SNITIRNQINALTSF | 88 |
| DRB3*0202 | 714 | 728 | KNNIFMSNSYPRDFV | 89 |
| DRB3*0202 | 617 | 631 | LGTVLRNLKLARKLM | 90 |
| DRB1*0301 | 504 | 518 | LIQPFMFRLDNRYQP | 91 |
| DRB1*0301 | 462 | 476 | YLPLVLGPTAMRKYL | 92 |
| DRB1*0301 | 617 | 631 | LGTVLRNLKLARKLM | 93 |
| DRB4*0101 | 444 | 458 | QEARKIVGAMVQIIT | 94 |
| DRB4*0101 | 689 | 703 | QQRQALAQISLPRII | 95 |
| DRB4*0101 | 248 | 262 | RSLMFMQWGQLLDHD | 96 |
| DRB5*0101 | 511 | 525 | RLDNRYQPMEPNPRV | 97 |
| DRB5*0101 | 97 | 111 | ELLSYFKQPVAATRT | 98 |
| DRB5*0101 | 616 | 630 | QLGTVLRNLKLARKL | 99 |

Any of the peptides described herein may encompass a naturally occurring variant that does not affect binding to an MHC class II molecule or recognition by a T cell receptor. Such variants are contemplated herein and included with reference to the sequence.

| SEQ ID NO: | |
|---|---|
| 100 | MAIIYLILLFTAVRGIKEEH<br>VIIQAEFYLNPDQSGEFMFD<br>FDGDEIFHVDMAKKETVWRL<br>EEFGRFASFEAQGALANIAV<br>DKANLEIMTKRSNYTPITNV<br>PPEVTVLTNSPVELREPNVL<br>ICFIDKFTPPVVNVTWLRNG<br>KPVTTGVSETVFLPREDHLF<br>RKFHYLPFLPSTEDVYDCRV<br>EHWGLDEPLLKHWEFDAPSP<br>LPETTESGGGGGDKTHTCPP<br>CPAPEAAGGPSVFLFPPKPK<br>DTLMISRTPEVTCVVVDVSH<br>EDPEVKFNWYVDGVEVHNAK<br>TKPREEQYNSTYRVVSVLTV<br>LHQDWLNGKEYKCKVSNKAL<br>PAPIEKTISKAKGQPREPQV<br>YTLPPCRDELTKNQVSLWCL<br>VKGFYPSDIAVEWESNGQPE<br>NNYKTTPPVLDSDGSFFLYS<br>KLTVDKSRWQQGNVFSCSVM<br>HEALHNHYTQKSLSLSPGKG<br>SGSGSGSC |
| 101 | MGSLQPLATLYLLGMLVASS<br>LGGDLIAEVETDKATVGGGG<br>GSGGGSGGSGDTQPRFLEQA<br>KCECHFLNGTERVWNLIRYT<br>YNQEEYARYNSDLGEYQAVT<br>ELGRPDAEYWNSQKDLLERR<br>RAEVDTYCRYNYGVVESFTV<br>QRRVQPKVTVYPSKTQPLQH<br>HNLLVCSVNGFYPGSIEVRW<br>FRNSQEEKAGVVSTGLIQNG<br>DWTFQTLVMLETVPRSGEVY<br>TCQVEHPSMMSPLTVQWSAR<br>SESAQSKSGGGGGDKTHTCP<br>PCPAPEAAGGPSVFLFPPKP<br>KDTLMISRTPEVTCVVVDVS<br>HEDPEVKFNWYVDGVEVHNA<br>KTKPREEQYNSTYRVVSVLT<br>VLHQDWLNGKEYKCKVSNKA<br>LPAPIEKTISKAKGQPREPQ |

-continued

| SEQ ID NO: | |
|---|---|
| | VCTLPPSRDELTKNQVSLSC<br>AVKGFYPSDIAVEWESNGQP<br>ENNYKTTPPVLDSDGSFFLV<br>SKLVDKSRWQQGNVFSCSVM<br>HEALHNHYTQKSLSLSPGK |
| 102 | IKEEHVIIQAEFYLNPDQSG<br>EFMFDFDGDEIFHVDMAKKE<br>TVWRLEEFGRFASFEAQGAL<br>ANIAVDKANLEIMTKRSNYT<br>PITNVPPEVTVLTNSPVELR<br>EPNVLICFIDKFTPPVVNVT<br>WLRNGKPVTTGVSETVFLPR<br>EDHLFRKFHYLPFLPSTEDV<br>YDCRVEHWGLDEPLLKHWEF<br>DAPSPLPETTE |
| 103 | GDTQPRFLEQAKCECHFLNG<br>TERVWNLIRYIYNQEEYARY<br>NSDLGEYQAVTELGRPDAEY<br>WNSQKDLLERRRAEVDTYCR<br>YNYGVVESFTVQRRVQPKVT<br>VYPSKTQPLQHHNLLVCSVN<br>GFYPGSIEVRWFRNSQEEKA<br>GVVSTGLIQNGDWTFQTLVM<br>LETVPRSGEVYTCQVEHPSM<br>MSPLTVQWSARSESAQSK |
| 104 | GQPREPQVCTLPPSRDELTK<br>NQVSLSCAVKGFYPSDIAVE<br>WESNGQPENNYKTTPPVLDS<br>DGSFFLVSKLVDKSRWQQGN<br>VFSCSVMHEALHNHYTQKSL<br>SLSPGK |
| 105 | GQPREPQVCTLPPSRDELTK<br>NQVSLSCAVKGFYPSDIAVE<br>WESNGQPENNYKTTPPVLDS<br>DGSFFLVSKLVDKSRWQQGN<br>VFSCSVMHEALHNHYTQKSL<br>SLSPGK |

What is claimed is:

1. A method of treating non-alcoholic fatty liver disease (NAFLD) and/or non-alcoholic steatohepatitis (NASH) in an individual comprising administering to the individual a composition comprising:

a plurality of antigen-major histocompatibility class II complexes (antigen-MHC-II complexes), wherein each antigen-MHC-II complex is coupled to a nanoparticle core, wherein the nanoparticle core has a diameter of between 1 and about 100 nanometers, and wherein each antigen-MHC-II complex comprises SEQ ID NO:100 and SEQ ID NO: 101.

2. The method of claim 1, wherein the nanoparticle core comprises a metal or metal oxide.

3. The method of claim 2, wherein the metal oxide is iron oxide.

4. The method of claim 1, wherein the diameter of the nanoparticle core is between about 5 nanometers and about 50 nanometers.

5. The method of claim 1, wherein the plurality of antigen-MHC-II complexes is coupled to the nanoparticle core at an antigen-MHC-II complex to nanoparticle core ratio of at least 10:1 and no more than about 150:1.

6. The method of claim 5, wherein the plurality of antigen-MHC-II complexes is coupled to the nanoparticle core at a density from about 0.4 to about 13 antigen-MHC-II complexes per 100 $nm^2$ of nanoparticle core surface area.

7. The method of claim 6, wherein the plurality of antigen-MHC-II complexes is covalently coupled to the nanoparticle core by a dextran linker and/or a polyethylene glycol (PEG), and wherein the linker has a mass of less than about 5 kilodaltons.

8. The method of claim 7, wherein the nanoparticle core further comprises a biocompatible coating.

9. The method of claim 1, wherein the composition further comprises a pharmaceutically acceptable stabilizer, excipient, diluent, or any combination thereof.

10. The method of claim 1, wherein the composition is formulated for intravenous administration.

* * * * *

SEQUENCE LISTING

<160> NUMBER OF SEQ ID NOS: 111

<210> SEQ ID NO 1
<211> LENGTH: 15
<212> TYPE: PRT
<213> ORGANISM: Homo sapiens

<400> SEQUENCE: 1

```
Gly Arg Val Phe Val Ser Pro Leu Ala Lys Lys Leu Ala Val Glu
1               5                   10                  15
```

<210> SEQ ID NO 2
<211> LENGTH: 15
<212> TYPE: PRT
<213> ORGANISM: Homo sapiens

<400> SEQUENCE: 2

```
Arg Leu Leu Leu Gln Leu Leu Gly Ser Pro Gly Arg Arg Tyr Tyr
1               5                   10                  15
```

<210> SEQ ID NO 3
<211> LENGTH: 15
<212> TYPE: PRT
<213> ORGANISM: Homo sapiens

```
<400> SEQUENCE: 3

Asp Ile Pro Ile Ser Asn Ile Arg Arg Val Ile Ala Gln Arg Leu
1               5                   10                  15


<210> SEQ ID NO 4
<211> LENGTH: 15
<212> TYPE: PRT
<213> ORGANISM: Homo sapiens

<400> SEQUENCE: 4

Gly Arg Val Phe Val Ser Pro Leu Ala Lys Lys Leu Ala Val Glu
1               5                   10                  15


<210> SEQ ID NO 5
<211> LENGTH: 15
<212> TYPE: PRT
<213> ORGANISM: Homo sapiens

<400> SEQUENCE: 5

Ser Pro Gly Arg Arg Tyr Tyr Ser Leu Pro Pro His Gln Lys Val
1               5                   10                  15


<210> SEQ ID NO 6
<211> LENGTH: 15
<212> TYPE: PRT
<213> ORGANISM: Homo sapiens

<400> SEQUENCE: 6

Glu Thr Ile Ala Asn Asp Val Val Ser Leu Ala Thr Lys Ala Arg
1               5                   10                  15


<210> SEQ ID NO 7
<211> LENGTH: 15
<212> TYPE: PRT
<213> ORGANISM: Homo sapiens

<400> SEQUENCE: 7

Ala Gln Trp Leu Ala Glu Phe Arg Lys Tyr Leu Glu Lys Pro Ile
1               5                   10                  15


<210> SEQ ID NO 8
<211> LENGTH: 14
<212> TYPE: PRT
<213> ORGANISM: Homo sapiens

<400> SEQUENCE: 8

Gly Asp Leu Ile Ala Glu Val Glu Thr Asp Lys Ala Thr Val
1               5                   10


<210> SEQ ID NO 9
<211> LENGTH: 14
<212> TYPE: PRT
<213> ORGANISM: Homo sapiens

<400> SEQUENCE: 9

Gly Asp Leu Leu Ala Glu Ile Glu Thr Asp Lys Ala Thr Ile
1               5                   10


<210> SEQ ID NO 10
<211> LENGTH: 15
<212> TYPE: PRT
<213> ORGANISM: Homo sapiens

<400> SEQUENCE: 10
```

Gly Asp Leu Leu Ala Glu Ile Glu Thr Asp Lys Ala Thr Ile Gly
1 5 10 15

<210> SEQ ID NO 11
<211> LENGTH: 15
<212> TYPE: PRT
<213> ORGANISM: Homo sapiens

<400> SEQUENCE: 11

Asp Ile Pro Ile Ser Asn Ile Arg Arg Val Ile Ala Gln Arg Leu
1 5 10 15

<210> SEQ ID NO 12
<211> LENGTH: 15
<212> TYPE: PRT
<213> ORGANISM: Homo sapiens

<400> SEQUENCE: 12

Ser Pro Gly Arg Arg Tyr Tyr Ser Leu Pro Pro His Gln Lys Val
1 5 10 15

<210> SEQ ID NO 13
<211> LENGTH: 15
<212> TYPE: PRT
<213> ORGANISM: Homo sapiens

<400> SEQUENCE: 13

Gly Asn Pro Glu Ser Ser Phe Asn Asp Glu Asn Leu Arg Ile Val
1 5 10 15

<210> SEQ ID NO 14
<211> LENGTH: 15
<212> TYPE: PRT
<213> ORGANISM: Homo sapiens

<400> SEQUENCE: 14

Ser Phe Asn Asp Glu Asn Leu Arg Ile Val Val Ala Asp Leu Phe
1 5 10 15

<210> SEQ ID NO 15
<211> LENGTH: 15
<212> TYPE: PRT
<213> ORGANISM: Homo sapiens

<400> SEQUENCE: 15

Leu Leu Leu Met Ile Leu His Pro Asp Val Gln Arg Arg Val Gln
1 5 10 15

<210> SEQ ID NO 16
<211> LENGTH: 20
<212> TYPE: PRT
<213> ORGANISM: Homo sapiens

<400> SEQUENCE: 16

Thr Leu Ala Trp Gly Leu Leu Leu Met Ile Leu His Pro Asp Val Gln
1 5 10 15

Arg Arg Val Gln
20

<210> SEQ ID NO 17
<211> LENGTH: 20
<212> TYPE: PRT
<213> ORGANISM: Homo sapiens

<400> SEQUENCE: 17

Thr Thr Leu Ile Thr Asn Leu Ser Ser Val Leu Lys Asp Glu Ala Val
1 5 10 15

Trp Glu Lys Pro
20

<210> SEQ ID NO 18
<211> LENGTH: 15
<212> TYPE: PRT
<213> ORGANISM: Homo sapiens

<400> SEQUENCE: 18

Gly Arg Arg Phe Glu Tyr Asp Asp Pro Arg Phe Leu Arg Leu Leu
1 5 10 15

<210> SEQ ID NO 19
<211> LENGTH: 15
<212> TYPE: PRT
<213> ORGANISM: Homo sapiens

<400> SEQUENCE: 19

Ala Leu Val Pro Leu Ala Val Ile Val Ala Ile Phe Leu Leu Leu
1 5 10 15

<210> SEQ ID NO 20
<211> LENGTH: 15
<212> TYPE: PRT
<213> ORGANISM: Homo sapiens

<400> SEQUENCE: 20

Glu Asn Leu Arg Ile Val Val Ala Asp Leu Phe Ser Ala Gly Met
1 5 10 15

<210> SEQ ID NO 21
<211> LENGTH: 15
<212> TYPE: PRT
<213> ORGANISM: Homo sapiens

<400> SEQUENCE: 21

Phe Leu Arg Glu Val Leu Asn Ala Val Pro Val Leu Leu His Ile
1 5 10 15

<210> SEQ ID NO 22
<211> LENGTH: 15
<212> TYPE: PRT
<213> ORGANISM: Homo sapiens

<400> SEQUENCE: 22

Ala Gly Lys Val Leu Arg Phe Gln Lys Ala Phe Leu Thr Gln Leu
1 5 10 15

<210> SEQ ID NO 23
<211> LENGTH: 15
<212> TYPE: PRT
<213> ORGANISM: Homo sapiens

<400> SEQUENCE: 23

Ile Phe Leu Leu Leu Val Asp Leu Met His Arg Arg Gln Arg Trp
1 5 10 15

<210> SEQ ID NO 24
<211> LENGTH: 15
<212> TYPE: PRT
<213> ORGANISM: Homo sapiens

<400> SEQUENCE: 24

Ala Leu Ala Gly Lys Val Leu Arg Phe Gln Lys Ala Phe Leu Thr
1               5                   10                  15

<210> SEQ ID NO 25
<211> LENGTH: 15
<212> TYPE: PRT
<213> ORGANISM: Homo sapiens

<400> SEQUENCE: 25

Gly Leu Leu Leu Met Ile Leu His Pro Asp Val Gln Arg Arg Val
1               5                   10                  15

<210> SEQ ID NO 26
<211> LENGTH: 15
<212> TYPE: PRT
<213> ORGANISM: Homo sapiens

<400> SEQUENCE: 26

Glu Asn Leu Arg Ile Val Val Ala Asp Leu Phe Ser Ala Gly Met
1               5                   10                  15

<210> SEQ ID NO 27
<211> LENGTH: 15
<212> TYPE: PRT
<213> ORGANISM: Homo sapiens

<400> SEQUENCE: 27

Val Lys Pro Glu Ala Phe Leu Pro Phe Ser Ala Gly Arg Arg Ala
1               5                   10                  15

<210> SEQ ID NO 28
<211> LENGTH: 15
<212> TYPE: PRT
<213> ORGANISM: Homo sapiens

<400> SEQUENCE: 28

Ala Gly Lys Val Leu Arg Phe Gln Lys Ala Phe Leu Thr Gln Leu
1               5                   10                  15

<210> SEQ ID NO 29
<211> LENGTH: 15
<212> TYPE: PRT
<213> ORGANISM: Homo sapiens

<400> SEQUENCE: 29

Ala Ile Phe Leu Leu Leu Val Asp Leu Met His Arg Arg Gln Arg
1               5                   10                  15

<210> SEQ ID NO 30
<211> LENGTH: 15
<212> TYPE: PRT
<213> ORGANISM: Homo sapiens

<400> SEQUENCE: 30

Asp Pro Arg Phe Leu Arg Leu Leu Asp Leu Ala Gln Glu Gly Leu
1               5                   10                  15

<210> SEQ ID NO 31
<211> LENGTH: 15
<212> TYPE: PRT
<213> ORGANISM: Homo sapiens

<400> SEQUENCE: 31

Arg Met Glu Leu Phe Leu Phe Phe Thr Ser Leu Leu Gln His Phe
1 5 10 15

<210> SEQ ID NO 32
<211> LENGTH: 15
<212> TYPE: PRT
<213> ORGANISM: Homo sapiens

<400> SEQUENCE: 32

Asp Leu Phe Ser Ala Gly Met Val Thr Thr Ser Thr Thr Leu Ala
1 5 10 15

<210> SEQ ID NO 33
<211> LENGTH: 15
<212> TYPE: PRT
<213> ORGANISM: Homo sapiens

<400> SEQUENCE: 33

Glu Leu Phe Leu Phe Phe Thr Ser Leu Leu Gln His Phe Ser Phe
1 5 10 15

<210> SEQ ID NO 34
<211> LENGTH: 15
<212> TYPE: PRT
<213> ORGANISM: Homo sapiens

<400> SEQUENCE: 34

Asp Gln Leu Arg Arg Arg Phe Gly Asp Val Phe Ser Leu Gln Leu
1 5 10 15

<210> SEQ ID NO 35
<211> LENGTH: 15
<212> TYPE: PRT
<213> ORGANISM: Homo sapiens

<400> SEQUENCE: 35

Glu Gln Arg Arg Phe Ser Val Ser Thr Leu Arg Asn Leu Gly Leu
1 5 10 15

<210> SEQ ID NO 36
<211> LENGTH: 20
<212> TYPE: PRT
<213> ORGANISM: Homo sapiens

<400> SEQUENCE: 36

Arg Arg Phe Glu Tyr Asp Asp Pro Arg Phe Leu Arg Leu Leu Asp Leu
1 5 10 15

Ala Gln Glu Gly
20

<210> SEQ ID NO 37
<211> LENGTH: 20
<212> TYPE: PRT
<213> ORGANISM: Homo sapiens

<400> SEQUENCE: 37

Ala Gly Met Val Thr Thr Ser Thr Thr Leu Ala Trp Gly Leu Leu Leu
1 5 10 15

Met Ile Leu His
20

<210> SEQ ID NO 38
<211> LENGTH: 15

-continued

<212> TYPE: PRT
<213> ORGANISM: Homo sapiens

<400> SEQUENCE: 38

Thr Thr Ala Glu Arg Glu Ile Val Arg Asp Ile Lys Glu Lys Leu
1 5 10 15

<210> SEQ ID NO 39
<211> LENGTH: 15
<212> TYPE: PRT
<213> ORGANISM: Homo sapiens

<400> SEQUENCE: 39

Ala Leu Pro His Ala Ile Leu Arg Leu Asp Leu Ala Gly Arg Asp
1 5 10 15

<210> SEQ ID NO 40
<211> LENGTH: 15
<212> TYPE: PRT
<213> ORGANISM: Homo sapiens

<400> SEQUENCE: 40

Ser Gly Arg Thr Thr Gly Ile Val Met Asp Ser Gly Asp Gly Val
1 5 10 15

<210> SEQ ID NO 41
<211> LENGTH: 15
<212> TYPE: PRT
<213> ORGANISM: Homo sapiens

<400> SEQUENCE: 41

Asp Tyr Leu Met Lys Ile Leu Thr Glu Arg Gly Tyr Ser Phe Thr
1 5 10 15

<210> SEQ ID NO 42
<211> LENGTH: 15
<212> TYPE: PRT
<213> ORGANISM: Homo sapiens

<400> SEQUENCE: 42

Pro His Ala Ile Leu Arg Leu Asp Leu Ala Gly Arg Asp Leu Thr
1 5 10 15

<210> SEQ ID NO 43
<211> LENGTH: 15
<212> TYPE: PRT
<213> ORGANISM: Homo sapiens

<400> SEQUENCE: 43

Ala Met Tyr Val Ala Ile Gln Ala Val Leu Ser Leu Tyr Ala Ser
1 5 10 15

<210> SEQ ID NO 44
<211> LENGTH: 15
<212> TYPE: PRT
<213> ORGANISM: Homo sapiens

<400> SEQUENCE: 44

Ala Met Tyr Val Ala Ile Gln Ala Val Leu Ser Leu Tyr Ala Ser
1 5 10 15

<210> SEQ ID NO 45
<211> LENGTH: 15
<212> TYPE: PRT
<213> ORGANISM: Homo sapiens

<400> SEQUENCE: 45

Leu Pro His Ala Ile Leu Arg Leu Asp Leu Ala Gly Arg Asp Leu
1 5 10 15

<210> SEQ ID NO 46
<211> LENGTH: 15
<212> TYPE: PRT
<213> ORGANISM: Homo sapiens

<400> SEQUENCE: 46

Thr Pro Ala Met Tyr Val Ala Ile Gln Ala Val Leu Ser Leu Tyr
1 5 10 15

<210> SEQ ID NO 47
<211> LENGTH: 15
<212> TYPE: PRT
<213> ORGANISM: Homo sapiens

<400> SEQUENCE: 47

Pro Ile Tyr Glu Gly Tyr Ala Leu Pro His Ala Ile Leu Arg Leu
1 5 10 15

<210> SEQ ID NO 48
<211> LENGTH: 15
<212> TYPE: PRT
<213> ORGANISM: Homo sapiens

<400> SEQUENCE: 48

Asp Ala Pro Arg Ala Val Phe Pro Ser Ile Val Gly Arg Pro Arg
1 5 10 15

<210> SEQ ID NO 49
<211> LENGTH: 15
<212> TYPE: PRT
<213> ORGANISM: Homo sapiens

<400> SEQUENCE: 49

Ser Thr Met Lys Ile Lys Ile Ile Ala Pro Pro Glu Arg Lys Tyr
1 5 10 15

<210> SEQ ID NO 50
<211> LENGTH: 15
<212> TYPE: PRT
<213> ORGANISM: Homo sapiens

<400> SEQUENCE: 50

Gly Arg Thr Thr Gly Ile Val Met Asp Ser Gly Asp Gly Val Thr
1 5 10 15

<210> SEQ ID NO 51
<211> LENGTH: 15
<212> TYPE: PRT
<213> ORGANISM: Homo sapiens

<400> SEQUENCE: 51

Lys Ala Gly Phe Ala Gly Asp Asp Ala Pro Arg Ala Val Phe Pro
1 5 10 15

<210> SEQ ID NO 52
<211> LENGTH: 15
<212> TYPE: PRT
<213> ORGANISM: Homo sapiens

<400> SEQUENCE: 52

Leu Pro His Ala Ile Leu Arg Leu Asp Leu Ala Gly Arg Asp Leu
1 5 10 15

<210> SEQ ID NO 53
<211> LENGTH: 15
<212> TYPE: PRT
<213> ORGANISM: Homo sapiens

<400> SEQUENCE: 53

Tyr Lys Lys Leu Leu Lys Glu Arg Lys Glu Met Phe Ser Tyr Leu
1 5 10 15

<210> SEQ ID NO 54
<211> LENGTH: 15
<212> TYPE: PRT
<213> ORGANISM: Homo sapiens

<400> SEQUENCE: 54

Asp Glu Leu Arg Thr Asp Leu Lys Ala Val Glu Ala Lys Val Gln
1 5 10 15

<210> SEQ ID NO 55
<211> LENGTH: 15
<212> TYPE: PRT
<213> ORGANISM: Homo sapiens

<400> SEQUENCE: 55

Asn Lys Ile Thr Asn Ser Leu Val Leu Asp Ile Ile Lys Leu Ala
1 5 10 15

<210> SEQ ID NO 56
<211> LENGTH: 14
<212> TYPE: PRT
<213> ORGANISM: Homo sapiens

<400> SEQUENCE: 56

Asn Arg Leu Asp Arg Cys Leu Lys Ala Val Arg Lys Glu Arg
1 5 10

<210> SEQ ID NO 57
<211> LENGTH: 12
<212> TYPE: PRT
<213> ORGANISM: Homo sapiens

<400> SEQUENCE: 57

Leu Ile Gln Gln Gly Ala Arg Val Gly Arg Ile Asp
1 5 10

<210> SEQ ID NO 58
<211> LENGTH: 15
<212> TYPE: PRT
<213> ORGANISM: Homo sapiens

<400> SEQUENCE: 58

Lys Glu Met Phe Ser Tyr Leu Ser Asn Gln Ile Lys Lys Leu Ser
1 5 10 15

<210> SEQ ID NO 59
<211> LENGTH: 15
<212> TYPE: PRT
<213> ORGANISM: Homo sapiens

<400> SEQUENCE: 59

Gly Ser Ser Leu Leu Asn Lys Ile Thr Asn Ser Leu Val Leu Asp 1 5 10 15

<210> SEQ ID NO 60
<211> LENGTH: 15
<212> TYPE: PRT
<213> ORGANISM: Homo sapiens

<400> SEQUENCE: 60

Asn Asp Ser Phe Ile Gln Glu Ile Ser Lys Met Tyr Pro Gly Arg
1 5 10 15

<210> SEQ ID NO 61
<211> LENGTH: 15
<212> TYPE: PRT
<213> ORGANISM: Homo sapiens

<400> SEQUENCE: 61

Ser Thr Leu Glu Leu Phe Leu His Glu Leu Ala Ile Met Asp Ser
1 5 10 15

<210> SEQ ID NO 62
<211> LENGTH: 15
<212> TYPE: PRT
<213> ORGANISM: Homo sapiens

<400> SEQUENCE: 62

Ser Lys Cys Met His Leu Ile Gln Gln Gly Ala Arg Val Gly Arg
1 5 10 15

<210> SEQ ID NO 63
<211> LENGTH: 15
<212> TYPE: PRT
<213> ORGANISM: Homo sapiens

<400> SEQUENCE: 63

Asn Ser Leu Val Leu Asp Ile Ile Lys Leu Ala Gly Val His Thr
1 5 10 15

<210> SEQ ID NO 64
<211> LENGTH: 15
<212> TYPE: PRT
<213> ORGANISM: Homo sapiens

<400> SEQUENCE: 64

Arg Arg His Tyr Arg Phe Ile His Gly Ile Gly Arg Ser Gly Asp
1 5 10 15

<210> SEQ ID NO 65
<211> LENGTH: 15
<212> TYPE: PRT
<213> ORGANISM: Homo sapiens

<400> SEQUENCE: 65

Arg Ser His Glu His Leu Ile Arg Leu Leu Leu Glu Lys Gly Lys
1 5 10 15

<210> SEQ ID NO 66
<211> LENGTH: 15
<212> TYPE: PRT
<213> ORGANISM: Homo sapiens

<400> SEQUENCE: 66

Ser Asn Gly Tyr Lys Lys Leu Leu Lys Glu Arg Lys Glu Met Phe
1 5 10 15

-continued

<210> SEQ ID NO 67
<211> LENGTH: 15
<212> TYPE: PRT
<213> ORGANISM: Homo sapiens

<400> SEQUENCE: 67

Ser Pro Ser Leu Asp Val Leu Ile Thr Leu Leu Ser Leu Gly Ser
1 5 10 15

<210> SEQ ID NO 68
<211> LENGTH: 15
<212> TYPE: PRT
<213> ORGANISM: Homo sapiens

<400> SEQUENCE: 68

Asp Gln Lys Ser Cys Phe Lys Ser Met Ile Thr Ala Gly Phe Glu
1 5 10 15

<210> SEQ ID NO 69
<211> LENGTH: 15
<212> TYPE: PRT
<213> ORGANISM: Homo sapiens

<400> SEQUENCE: 69

Tyr Thr Phe Arg Gly Phe Met Ser His Thr Asn Asn Tyr Pro Cys
1 5 10 15

<210> SEQ ID NO 70
<211> LENGTH: 15
<212> TYPE: PRT
<213> ORGANISM: Homo sapiens

<400> SEQUENCE: 70

Tyr Asn Glu Arg Leu Leu His Thr Pro His Asn Pro Ile Ser Leu
1 5 10 15

<210> SEQ ID NO 71
<211> LENGTH: 15
<212> TYPE: PRT
<213> ORGANISM: Homo sapiens

<400> SEQUENCE: 71

Asp Cys Ile Leu Cys Ile His Ser Thr Thr Ser Cys Phe Ala Pro
1 5 10 15

<210> SEQ ID NO 72
<211> LENGTH: 15
<212> TYPE: PRT
<213> ORGANISM: Homo sapiens

<400> SEQUENCE: 72

Ser Ser Leu Leu Asn Lys Ile Thr Asn Ser Leu Val Leu Asp Ile
1 5 10 15

<210> SEQ ID NO 73
<211> LENGTH: 15
<212> TYPE: PRT
<213> ORGANISM: Homo sapiens

<400> SEQUENCE: 73

Ala Leu Gln Glu Gly Leu Arg Arg Ala Val Ser Val Pro Leu Thr
1 5 10 15

<210> SEQ ID NO 74

<211> LENGTH: 15
<212> TYPE: PRT
<213> ORGANISM: Homo sapiens

<400> SEQUENCE: 74

Arg Arg Gln Phe Gln Ser Leu Asp Thr Thr Met Arg Arg Leu Ile
1 5 10 15

<210> SEQ ID NO 75
<211> LENGTH: 15
<212> TYPE: PRT
<213> ORGANISM: Homo sapiens

<400> SEQUENCE: 75

Glu Gln Arg Ile Arg Leu Val Val Ser Arg Leu Gly Leu Asp Ser
1 5 10 15

<210> SEQ ID NO 76
<211> LENGTH: 15
<212> TYPE: PRT
<213> ORGANISM: Homo sapiens

<400> SEQUENCE: 76

Ala Lys Thr Gln Ala Ala Leu Val Leu Asp Cys Leu Glu Thr Arg
1 5 10 15

<210> SEQ ID NO 77
<211> LENGTH: 15
<212> TYPE: PRT
<213> ORGANISM: Homo sapiens

<400> SEQUENCE: 77

Lys Val Gln Gly Ile Gly Trp Tyr Leu Asp Glu Lys Asn Leu Ala
1 5 10 15

<210> SEQ ID NO 78
<211> LENGTH: 15
<212> TYPE: PRT
<213> ORGANISM: Homo sapiens

<400> SEQUENCE: 78

Tyr Phe Asn Val Leu Ile Asn Leu Arg Asp Ile Thr Asp Glu Ala
1 5 10 15

<210> SEQ ID NO 79
<211> LENGTH: 15
<212> TYPE: PRT
<213> ORGANISM: Homo sapiens

<400> SEQUENCE: 79

Leu Pro Val Val Gly Ser Gln Leu Val Gly Leu Val Pro Leu Lys
1 5 10 15

<210> SEQ ID NO 80
<211> LENGTH: 15
<212> TYPE: PRT
<213> ORGANISM: Homo sapiens

<400> SEQUENCE: 80

Ile Arg Leu Val Val Ser Arg Leu Gly Leu Asp Ser Leu Cys Pro
1 5 10 15

<210> SEQ ID NO 81
<211> LENGTH: 15
<212> TYPE: PRT

<213> ORGANISM: Homo sapiens

<400> SEQUENCE: 81

Glu Leu Ser Leu Pro Val Val Gly Ser Gln Leu Val Gly Leu Val
1 5 10 15

<210> SEQ ID NO 82
<211> LENGTH: 15
<212> TYPE: PRT
<213> ORGANISM: Homo sapiens

<400> SEQUENCE: 82

Gly Val Phe Gly Ala Tyr Phe Asn Val Leu Ile Asn Leu Arg Asp
1 5 10 15

<210> SEQ ID NO 83
<211> LENGTH: 15
<212> TYPE: PRT
<213> ORGANISM: Homo sapiens

<400> SEQUENCE: 83

Thr Thr Met Arg Arg Leu Ile Pro Pro Phe Arg Glu Ala Ser Ala
1 5 10 15

<210> SEQ ID NO 84
<211> LENGTH: 15
<212> TYPE: PRT
<213> ORGANISM: Homo sapiens

<400> SEQUENCE: 84

Glu Glu Glu Gln Arg Ile Arg Leu Val Val Ser Arg Leu Gly Leu
1 5 10 15

<210> SEQ ID NO 85
<211> LENGTH: 15
<212> TYPE: PRT
<213> ORGANISM: Homo sapiens

<400> SEQUENCE: 85

Gly Leu Val Pro Leu Lys Ala Leu Leu Asp Ala Ala Ala Phe Tyr
1 5 10 15

<210> SEQ ID NO 86
<211> LENGTH: 15
<212> TYPE: PRT
<213> ORGANISM: Homo sapiens

<400> SEQUENCE: 86

Val Leu Ile Asn Leu Arg Asp Ile Thr Asp Glu Ala Phe Lys Asp
1 5 10 15

<210> SEQ ID NO 87
<211> LENGTH: 15
<212> TYPE: PRT
<213> ORGANISM: Homo sapiens

<400> SEQUENCE: 87

Arg Leu Val Val Ser Arg Leu Gly Leu Asp Ser Leu Cys Pro Phe
1 5 10 15

<210> SEQ ID NO 88
<211> LENGTH: 15
<212> TYPE: PRT
<213> ORGANISM: Homo sapiens

<400> SEQUENCE: 88

Ser Asn Ile Thr Ile Arg Asn Gln Ile Asn Ala Leu Thr Ser Phe
1 5 10 15

<210> SEQ ID NO 89
<211> LENGTH: 15
<212> TYPE: PRT
<213> ORGANISM: Homo sapiens

<400> SEQUENCE: 89

Lys Asn Asn Ile Phe Met Ser Asn Ser Tyr Pro Arg Asp Phe Val
1 5 10 15

<210> SEQ ID NO 90
<211> LENGTH: 15
<212> TYPE: PRT
<213> ORGANISM: Homo sapiens

<400> SEQUENCE: 90

Leu Gly Thr Val Leu Arg Asn Leu Lys Leu Ala Arg Lys Leu Met
1 5 10 15

<210> SEQ ID NO 91
<211> LENGTH: 15
<212> TYPE: PRT
<213> ORGANISM: Homo sapiens

<400> SEQUENCE: 91

Leu Ile Gln Pro Phe Met Phe Arg Leu Asp Asn Arg Tyr Gln Pro
1 5 10 15

<210> SEQ ID NO 92
<211> LENGTH: 15
<212> TYPE: PRT
<213> ORGANISM: Homo sapiens

<400> SEQUENCE: 92

Tyr Leu Pro Leu Val Leu Gly Pro Thr Ala Met Arg Lys Tyr Leu
1 5 10 15

<210> SEQ ID NO 93
<211> LENGTH: 15
<212> TYPE: PRT
<213> ORGANISM: Homo sapiens

<400> SEQUENCE: 93

Leu Gly Thr Val Leu Arg Asn Leu Lys Leu Ala Arg Lys Leu Met
1 5 10 15

<210> SEQ ID NO 94
<211> LENGTH: 15
<212> TYPE: PRT
<213> ORGANISM: Homo sapiens

<400> SEQUENCE: 94

Gln Glu Ala Arg Lys Ile Val Gly Ala Met Val Gln Ile Ile Thr
1 5 10 15

<210> SEQ ID NO 95
<211> LENGTH: 15
<212> TYPE: PRT
<213> ORGANISM: Homo sapiens

<400> SEQUENCE: 95

Gln Gln Arg Gln Ala Leu Ala Gln Ile Ser Leu Pro Arg Ile Ile
1 5 10 15

<210> SEQ ID NO 96
<211> LENGTH: 15
<212> TYPE: PRT
<213> ORGANISM: Homo sapiens

<400> SEQUENCE: 96

Arg Ser Leu Met Phe Met Gln Trp Gly Gln Leu Leu Asp His Asp
1 5 10 15

<210> SEQ ID NO 97
<211> LENGTH: 15
<212> TYPE: PRT
<213> ORGANISM: Homo sapiens

<400> SEQUENCE: 97

Arg Leu Asp Asn Arg Tyr Gln Pro Met Glu Pro Asn Pro Arg Val
1 5 10 15

<210> SEQ ID NO 98
<211> LENGTH: 15
<212> TYPE: PRT
<213> ORGANISM: Homo sapiens

<400> SEQUENCE: 98

Glu Leu Leu Ser Tyr Phe Lys Gln Pro Val Ala Ala Thr Arg Thr
1 5 10 15

<210> SEQ ID NO 99
<211> LENGTH: 15
<212> TYPE: PRT
<213> ORGANISM: Homo sapiens

<400> SEQUENCE: 99

Gln Leu Gly Thr Val Leu Arg Asn Leu Lys Leu Ala Arg Lys Leu
1 5 10 15

<210> SEQ ID NO 100
<211> LENGTH: 448
<212> TYPE: PRT
<213> ORGANISM: Homo sapiens

<400> SEQUENCE: 100

Met Ala Ile Ile Tyr Leu Ile Leu Leu Phe Thr Ala Val Arg Gly Ile
1 5 10 15

Lys Glu Glu His Val Ile Ile Gln Ala Glu Phe Tyr Leu Asn Pro Asp
20 25 30

Gln Ser Gly Glu Phe Met Phe Asp Phe Asp Gly Asp Glu Ile Phe His
35 40 45

Val Asp Met Ala Lys Lys Glu Thr Val Trp Arg Leu Glu Glu Phe Gly
50 55 60

Arg Phe Ala Ser Phe Glu Ala Gln Gly Ala Leu Ala Asn Ile Ala Val
65 70 75 80

Asp Lys Ala Asn Leu Glu Ile Met Thr Lys Arg Ser Asn Tyr Thr Pro
85 90 95

Ile Thr Asn Val Pro Pro Glu Val Thr Val Leu Thr Asn Ser Pro Val
100 105 110

Glu Leu Arg Glu Pro Asn Val Leu Ile Cys Phe Ile Asp Lys Phe Thr
115 120 125

```
Pro Pro Val Val Asn Val Thr Trp Leu Arg Asn Gly Lys Pro Val Thr
    130                 135                 140

Thr Gly Val Ser Glu Thr Val Phe Leu Pro Arg Glu Asp His Leu Phe
145                 150                 155                 160

Arg Lys Phe His Tyr Leu Pro Phe Leu Pro Ser Thr Glu Asp Val Tyr
                165                 170                 175

Asp Cys Arg Val Glu His Trp Gly Leu Asp Glu Pro Leu Leu Lys His
            180                 185                 190

Trp Glu Phe Asp Ala Pro Ser Pro Leu Pro Glu Thr Thr Glu Ser Gly
        195                 200                 205

Gly Gly Gly Gly Asp Lys Thr His Thr Cys Pro Pro Cys Pro Ala Pro
    210                 215                 220

Glu Ala Ala Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser His Glu Asp Pro Glu Val Lys Phe Asn Trp Tyr Val Asp
            260                 265                 270

Gly Val Glu Val His Asn Ala Lys Thr Lys Pro Arg Glu Glu Gln Tyr
        275                 280                 285

Asn Ser Thr Tyr Arg Val Val Ser Val Leu Thr Val Leu His Gln Asp
    290                 295                 300

Trp Leu Asn Gly Lys Glu Tyr Lys Cys Lys Val Ser Asn Lys Ala Leu
305                 310                 315                 320

Pro Ala Pro Ile Glu Lys Thr Ile Ser Lys Ala Lys Gly Gln Pro Arg
                325                 330                 335

Glu Pro Gln Val Tyr Thr Leu Pro Pro Cys Arg Asp Glu Leu Thr Lys
            340                 345                 350

Asn Gln Val Ser Leu Trp Cys Leu Val Lys Gly Phe Tyr Pro Ser Asp
        355                 360                 365

Ile Ala Val Glu Trp Glu Ser Asn Gly Gln Pro Glu Asn Asn Tyr Lys
    370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Asn His Tyr Thr Gln Lys Ser
            420                 425                 430

Leu Ser Leu Ser Pro Gly Lys Gly Ser Gly Ser Gly Ser Gly Ser Cys
        435                 440                 445
```

<210> SEQ ID NO 101
<211> LENGTH: 479
<212> TYPE: PRT
<213> ORGANISM: Homo sapiens

<400> SEQUENCE: 101

```
Met Gly Ser Leu Gln Pro Leu Ala Thr Leu Tyr Leu Leu Gly Met Leu
1               5                   10                  15

Val Ala Ser Ser Leu Gly Gly Asp Leu Ile Ala Glu Val Glu Thr Asp
            20                  25                  30

Lys Ala Thr Val Gly Gly Gly Gly Gly Ser Gly Gly Gly Ser Gly Gly
        35                  40                  45

Ser Gly Asp Thr Gln Pro Arg Phe Leu Glu Gln Ala Lys Cys Glu Cys
    50                  55                  60
```

-continued

```
His Phe Leu Asn Gly Thr Glu Arg Val Trp Asn Leu Ile Arg Tyr Ile
65                  70                  75                  80

Tyr Asn Gln Glu Glu Tyr Ala Arg Tyr Asn Ser Asp Leu Gly Glu Tyr
                85                  90                  95

Gln Ala Val Thr Glu Leu Gly Arg Pro Asp Ala Glu Tyr Trp Asn Ser
            100                 105                 110

Gln Lys Asp Leu Leu Glu Arg Arg Arg Ala Glu Val Asp Thr Tyr Cys
        115                 120                 125

Arg Tyr Asn Tyr Gly Val Val Glu Ser Phe Thr Val Gln Arg Arg Val
    130                 135                 140

Gln Pro Lys Val Thr Val Tyr Pro Ser Lys Thr Gln Pro Leu Gln His
145                 150                 155                 160

His Asn Leu Leu Val Cys Ser Val Asn Gly Phe Tyr Pro Gly Ser Ile
                165                 170                 175

Glu Val Arg Trp Phe Arg Asn Ser Gln Glu Glu Lys Ala Gly Val Val
            180                 185                 190

Ser Thr Gly Leu Ile Gln Asn Gly Asp Trp Thr Phe Gln Thr Leu Val
        195                 200                 205

Met Leu Glu Thr Val Pro Arg Ser Gly Glu Val Tyr Thr Cys Gln Val
    210                 215                 220

Glu His Pro Ser Met Met Ser Pro Leu Thr Val Gln Trp Ser Ala Arg
225                 230                 235                 240

Ser Glu Ser Ala Gln Ser Lys Ser Gly Gly Gly Gly Gly Asp Lys Thr
                245                 250                 255

His Thr Cys Pro Pro Cys Pro Ala Pro Glu Ala Ala Gly Gly Pro Ser
            260                 265                 270

Val Phe Leu Phe Pro Pro Lys Pro Lys Asp Thr Leu Met Ile Ser Arg
        275                 280                 285

Thr Pro Glu Val Thr Cys Val Val Val Asp Val Ser His Glu Asp Pro
    290                 295                 300

Glu Val Lys Phe Asn Trp Tyr Val Asp Gly Val Glu Val His Asn Ala
305                 310                 315                 320

Lys Thr Lys Pro Arg Glu Glu Gln Tyr Asn Ser Thr Tyr Arg Val Val
                325                 330                 335

Ser Val Leu Thr Val Leu His Gln Asp Trp Leu Asn Gly Lys Glu Tyr
            340                 345                 350

Lys Cys Lys Val Ser Asn Lys Ala Leu Pro Ala Pro Ile Glu Lys Thr
        355                 360                 365

Ile Ser Lys Ala Lys Gly Gln Pro Arg Glu Pro Gln Val Cys Thr Leu
    370                 375                 380

Pro Pro Ser Arg Asp Glu Leu Thr Lys Asn Gln Val Ser Leu Ser Cys
385                 390                 395                 400

Ala Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
            420                 425                 430

Ser Asp Gly Ser Phe Phe Leu Val Ser Lys Leu Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys
465                 470                 475
```

<210> SEQ ID NO 102
<211> LENGTH: 191
<212> TYPE: PRT
<213> ORGANISM: Homo sapiens

<400> SEQUENCE: 102

Ile Lys Glu Glu His Val Ile Ile Gln Ala Glu Phe Tyr Leu Asn Pro
1               5                   10                  15

Asp Gln Ser Gly Glu Phe Met Phe Asp Phe Asp Gly Asp Glu Ile Phe
            20                  25                  30

His Val Asp Met Ala Lys Lys Glu Thr Val Trp Arg Leu Glu Glu Phe
        35                  40                  45

Gly Arg Phe Ala Ser Phe Glu Ala Gln Gly Ala Leu Ala Asn Ile Ala
    50                  55                  60

Val Asp Lys Ala Asn Leu Glu Ile Met Thr Lys Arg Ser Asn Tyr Thr
65                  70                  75                  80

Pro Ile Thr Asn Val Pro Pro Glu Val Thr Val Leu Thr Asn Ser Pro
                85                  90                  95

Val Glu Leu Arg Glu Pro Asn Val Leu Ile Cys Phe Ile Asp Lys Phe
            100                 105                 110

Thr Pro Pro Val Val Asn Val Thr Trp Leu Arg Asn Gly Lys Pro Val
        115                 120                 125

Thr Thr Gly Val Ser Glu Thr Val Phe Leu Pro Arg Glu Asp His Leu
    130                 135                 140

Phe Arg Lys Phe His Tyr Leu Pro Phe Leu Pro Ser Thr Glu Asp Val
145                 150                 155                 160

Tyr Asp Cys Arg Val Glu His Trp Gly Leu Asp Glu Pro Leu Leu Lys
                165                 170                 175

His Trp Glu Phe Asp Ala Pro Ser Pro Leu Pro Glu Thr Thr Glu
            180                 185                 190

<210> SEQ ID NO 103
<211> LENGTH: 198
<212> TYPE: PRT
<213> ORGANISM: Homo sapiens

<400> SEQUENCE: 103

Gly Asp Thr Gln Pro Arg Phe Leu Glu Gln Ala Lys Cys Glu Cys His
1               5                   10                  15

Phe Leu Asn Gly Thr Glu Arg Val Trp Asn Leu Ile Arg Tyr Ile Tyr
            20                  25                  30

Asn Gln Glu Glu Tyr Ala Arg Tyr Asn Ser Asp Leu Gly Glu Tyr Gln
        35                  40                  45

Ala Val Thr Glu Leu Gly Arg Pro Asp Ala Glu Tyr Trp Asn Ser Gln
    50                  55                  60

Lys Asp Leu Leu Glu Arg Arg Arg Ala Glu Val Asp Thr Tyr Cys Arg
65                  70                  75                  80

Tyr Asn Tyr Gly Val Val Glu Ser Phe Thr Val Gln Arg Arg Val Gln
                85                  90                  95

Pro Lys Val Thr Val Tyr Pro Ser Lys Thr Gln Pro Leu Gln His His
            100                 105                 110

Asn Leu Leu Val Cys Ser Val Asn Gly Phe Tyr Pro Gly Ser Ile Glu
        115                 120                 125

Val Arg Trp Phe Arg Asn Ser Gln Glu Glu Lys Ala Gly Val Val Ser
    130                 135                 140

```
Thr Gly Leu Ile Gln Asn Gly Asp Trp Thr Phe Gln Thr Leu Val Met
145                 150                 155                 160

Leu Glu Thr Val Pro Arg Ser Gly Glu Val Tyr Thr Cys Gln Val Glu
                165                 170                 175

His Pro Ser Met Met Ser Pro Leu Thr Val Gln Trp Ser Ala Arg Ser
            180                 185                 190

Glu Ser Ala Gln Ser Lys
        195


<210> SEQ ID NO 104
<211> LENGTH: 106
<212> TYPE: PRT
<213> ORGANISM: Homo sapiens

<400> SEQUENCE: 104

Gly Gln Pro Arg Glu Pro Gln Val Cys Thr Leu Pro Pro Ser Arg Asp
1               5                   10                  15

Glu Leu Thr Lys Asn Gln Val Ser Leu Ser Cys Ala Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Val Ser Lys Leu Val Asp Lys Ser Arg Trp Gln Gln Gly Asn
65                  70                  75                  80

Val Phe Ser Cys Ser Val Met His Glu Ala Leu His Asn His Tyr Thr
                85                  90                  95

Gln Lys Ser Leu Ser Leu Ser Pro Gly Lys
            100                 105


<210> SEQ ID NO 105
<211> LENGTH: 106
<212> TYPE: PRT
<213> ORGANISM: Homo sapiens

<400> SEQUENCE: 105

Gly Gln Pro Arg Glu Pro Gln Val Cys Thr Leu Pro Pro Ser Arg Asp
1               5                   10                  15

Glu Leu Thr Lys Asn Gln Val Ser Leu Ser Cys Ala Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Val Ser Lys Leu Val Asp Lys Ser Arg Trp Gln Gln Gly Asn
65                  70                  75                  80

Val Phe Ser Cys Ser Val Met His Glu Ala Leu His Asn His Tyr Thr
                85                  90                  95

Gln Lys Ser Leu Ser Leu Ser Pro Gly Lys
            100                 105


<210> SEQ ID NO 106
<211> LENGTH: 16
<212> TYPE: PRT
<213> ORGANISM: Homo sapiens

<400> SEQUENCE: 106

Leu Ala Glu Ile Glu Thr Asp Lys Ala Thr Ile Gly Phe Glu Val Gln
```

-continued

```
1               5                   10                  15


<210> SEQ ID NO 107
<211> LENGTH: 15
<212> TYPE: PRT
<213> ORGANISM: Homo sapiens

<400> SEQUENCE: 107

Glu Lys Pro Gln Asp Ile Glu Ala Phe Lys Asn Tyr Thr Leu Asp
1               5                   10                  15


<210> SEQ ID NO 108
<211> LENGTH: 15
<212> TYPE: PRT
<213> ORGANISM: Homo sapiens

<400> SEQUENCE: 108

Val Val Glu Gly Ala Leu His Ala Ala Arg Thr Ala Ser Gln Leu
1               5                   10                  15


<210> SEQ ID NO 109
<211> LENGTH: 15
<212> TYPE: PRT
<213> ORGANISM: Homo sapiens

<400> SEQUENCE: 109

Leu Ile Thr Asn Leu Ser Ser Ala Leu Lys Asp Glu Thr Val Trp
1               5                   10                  15


<210> SEQ ID NO 110
<211> LENGTH: 11
<212> TYPE: PRT
<213> ORGANISM: Homo sapiens

<400> SEQUENCE: 110

Ala His His Pro Ile Trp Ala Arg Met Asp Ala
1               5                   10


<210> SEQ ID NO 111
<211> LENGTH: 20
<212> TYPE: PRT
<213> ORGANISM: Homo sapiens

<400> SEQUENCE: 111

Glu Val Gly Trp Tyr Arg Ser Pro Phe Ser Arg Val Val His Leu Tyr
1               5                   10                  15

Arg Asn Gly Lys
            20
```